(12) United States Patent
Fares et al.

(10) Patent No.: US 9,884,901 B2
(45) Date of Patent: Feb. 6, 2018

(54) LONG-ACTING POLYPEPTIDES AND METHODS OF PRODUCING AND ADMINISTERING SAME

(71) Applicant: OPKO Biologics Ltd., Nes Ziona (IL)

(72) Inventors: Fuad Fares, Hourfish Village (IL); Udi Eyal Fima, Beer-Sheva (IL)

(73) Assignee: OPKO Biologics Ltd., Kiryat Gat (IL)

( * ) Notice: Subject to any disclaimer, the term of this patent is extended or adjusted under 35 U.S.C. 154(b) by 0 days.

(21) Appl. No.: 14/566,681

(22) Filed: Dec. 10, 2014

(65) Prior Publication Data

US 2015/0126445 A1 May 7, 2015

Related U.S. Application Data

(63) Continuation of application No. 14/309,496, filed on Jun. 19, 2014, now abandoned, which is a continuation-in-part of application No. 14/059,134, filed on Oct. 21, 2013, now abandoned, which is a continuation-in-part of application No. 13/804,354, filed on Mar. 14, 2013, now Pat. No. 8,946,155, which is a continuation-in-part of application No. 13/192,542, filed on Jul. 28, 2011, now Pat. No. 8,465,948, which is a continuation of application No. 12/401,755, filed on Mar. 11, 2009, now Pat. No. 8,114,836, which is a continuation of application No. 11/702,156, filed on Feb. 5, 2007, now abandoned, said application No. 14/309,496 is a continuation-in-part of application No. 13/195,931, filed on Aug. 2, 2011, now Pat. No. 8,450,269, which is a continuation-in-part of application No. 12/509,188, filed on Jul. 24, 2009, now Pat. No. 8,304,386, which is a continuation-in-part of application No. 12/476,916, filed on Jun. 2, 2009, now Pat. No. 8,048,849, which is a continuation-in-part of application No. 12/401,746, filed on Mar. 11, 2009, now Pat. No. 8,097,435, which is a continuation of application No. 11/700,911, filed on Feb. 1, 2007, now Pat. No. 7,553,940.

(60) Provisional application No. 60/764,761, filed on Feb. 3, 2006.

(51) Int. Cl.
*A61K 38/18* (2006.01)
*C07K 14/505* (2006.01)
*C07K 14/61* (2006.01)
*C07K 14/555* (2006.01)
*C07K 14/59* (2006.01)

(52) U.S. Cl.
CPC .......... *C07K 14/505* (2013.01); *C07K 14/555* (2013.01); *C07K 14/59* (2013.01); *C07K 14/61* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | MacConnel |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,880,634 A | 11/1989 | Speiser |
| 4,911,691 A | 3/1990 | Aniuk et al. |
| 5,011,771 A | 4/1991 | Bellet et al. |

(Continued)

FOREIGN PATENT DOCUMENTS

| | | |
|---|---|---|
| CN | 1528787 A | 9/2004 |
| CN | 1528894 A | 3/2006 |

(Continued)

OTHER PUBLICATIONS

McNeil. No Rest for Fatigue Researchers. Journal of National Cancer Institute vol. 100/:1129-1131 (2008).*
Minton et al. A Systematic Review and Meta-Analysis of the Pharmacological Treatment of Cancer-related Fatigue. Journal of National Cancer Institute vol. 100:1155-1166 (2008).*
Pouliot et al. A murine model for cancer treatment-related fatigue.. Abstract. Molecular Cancer Therapeutics, vol. 8, No. 12, Supp. SUPPL.1. Abstract Number: A28 (Dec 2009).*
Baron et al. Recombinant Human Erythropoietin Therapy Is Very Effective after an Autologous Peripheral Blood Stem Cell Transplant When Started Soon after Engraftment. Clinical Cancer Research, vol. 9, 5566-5572 (2003).*
Volberding. Consensus Statement: Anemia in HIV Infection—Current Trends, Treatment Options, and Practice Strategies. Clinical Therapeutics vol. 22, No. 9:1004-1020 (2000).*

(Continued)

*Primary Examiner* — Elizabeth C Kemmerer
*Assistant Examiner* — Regina M DeBerry
(74) *Attorney, Agent, or Firm* — Mark S. Cohen; Pearl Cohen; Zedek Latzer Baratz LLP

(57) ABSTRACT

A polypeptide and polynucleotides comprising at least two carboxy-terminal peptides (CTP) of chorionic gonadotrophin attached to a non-human peptide-of-interest are disclosed. Pharmaceutical compositions comprising the non-human polypeptides and polynucleotides of the invention and methods of using both human and non-human polypeptides and polynucleotides are also disclosed.

10 Claims, 10 Drawing Sheets

(56) References Cited

U.S. PATENT DOCUMENTS

| | | |
|---|---|---|
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,919,455 A | 7/1999 | Greenwald et al. |
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,585,837 B2 | 9/2009 | Shechter et al. |
| 7,649,084 B2 | 1/2010 | Lehmann et al. |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 8,476,234 B2 | 7/2013 | Fima et al. |
| 9,458,444 B2 | 10/2016 | Fima et al. |
| 2001/0007757 A1 | 7/2001 | Boime et al. |
| 2001/0028895 A1 | 10/2001 | Bisgaier et al. |
| 2002/0127652 A1 | 9/2002 | Schambye et al. |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1 | 8/2008 | Minev |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152182 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0048878 A1 | 3/2012 | Burger et al. |
| 2012/0114651 A1 | 5/2012 | De Wildt et al. |
| 2012/0208759 A1 | 8/2012 | Fima et al. |
| 2013/0184207 A1 | 7/2013 | Fares et al. |
| 2013/0243747 A1 | 9/2013 | Fima et al. |
| 2014/0113860 A1 | 4/2014 | Fima et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0072924 A1 | 3/2015 | Fima et al. |
| 2015/0133636 A1 | 5/2015 | Xenopoulos et al. |
| 2015/0158926 A1 | 6/2015 | Fares et al. |

FOREIGN PATENT DOCUMENTS

| | | |
|---|---|---|
| EP | 0264166 | 4/1988 |
| EP | 0374257 A1 | 6/1990 |
| JP | 2002226365 A | 8/2002 |
| JP | 2002255857 A | 9/2002 |
| JP | 2004269516 A | 9/2004 |
| KR | 20030037598 A | 5/2003 |
| KR | 20050021502 A | 5/2003 |
| WO | WO 1993/006844 | 4/1993 |
| WO | WO 1994/024148 A1 | 10/1994 |
| WO | WO 2000/023472 A2 | 4/2000 |
| WO | WO 2002/036169 A2 | 5/2002 |
| WO | WO 2002/048194 A1 | 6/2002 |
| WO | WO 2003 038100 A1 | 5/2003 |
| WO | WO 2003/046013 A1 | 6/2003 |
| WO | WO 2002/085311 A2 | 10/2003 |
| WO | WO 2004/006756 | 1/2004 |
| WO | WO 2004/089280 | 10/2004 |
| WO | WO 2005/035761 | 4/2005 |
| WO | WO 2005/080544 | 9/2005 |
| WO | WO 2006/051288 A2 | 5/2006 |
| WO | WO 2006/134340 | 12/2006 |
| WO | WO 2007/094985 | 8/2007 |
| WO | WO 2007/149406 A2 | 12/2007 |
| WO | WO 2010/007622 | 1/2010 |
| WO | WO 2011/004361 | 1/2011 |
| WO | WO 2011/087672 | 7/2011 |

(56) References Cited

FOREIGN PATENT DOCUMENTS

| WO | WO 2012/011752 | | 5/2012 |
|---|---|---|---|
| WO | WO 2012/167251 | | 12/2012 |
| WO | WO 2012/173422 | | 12/2012 |
| WO | WO 2003/048210 | A1 | 6/2013 |
| WO | WO 2013/157002 | | 10/2013 |
| WO | WO 2013/183052 | | 12/2013 |
| WO | WO 2014/080401 | | 5/2014 |

OTHER PUBLICATIONS

Carles-Bonnet et al. "H-Lys-Arg-Asn-Lys-Asn-Asn-OH is the minimal active structure of oxyntomodulin." Peptides 17.3 (1996): 557-561.
Edmunds et al. "Plasma erythropoietin levels and acquired cystic disease of the kidney in patients receiving regular haemodialysis treatment" Br J Haematol. Jun. 1991:78(2):275-7.
European Search Report for European Application No. 16187710.5 dated Oct. 14, 2016.
Jarrousse et al. "Oxyntomodulin (glucagon-37) and its C-terminal octapeptide inhibit gastric acid secretion", FEBS Lett. Aug. 19, 1985; 188(1): 81-4.
Krantz et al. "Specific binding of erythropoietin to spleen cells infected with the anemia strain of Friend virus" Proc Natl Acad Sci U S A. Dec. 1984;81(23):7574-8.
Littlewoord, T.J. "Erythropoietin for the treatment of anemia associated with hematological malignancy" Hematol Oncol. Mar. 2001;19(1):19-30.
Musto "The role of recombinant erythropoietin for the treatment of anemia in multiple myeloma" Leuk Lymphoma. Apr. 1998;29(3-4):283-91.
Stuart et al. "Polycythemia vera" Am Fam Physician, May 1, 2004;69(9):2139-44.
Tharakan et al. "Emerging therapies in the treatment of 'diabesity': beyond GLP-1" Trends Pharmacol Sci. Jan. 2011;32(1 ):8-15.
Verhoef et al. "Recombinant human erythropoietin for the treatment of anemia in the myelodysplastic syndromes: a clinical and erythrokinetic assessment" Ann Hematol. Jan. 1992,64(1):16-21.
Ameredes et al. "Growth Hormone Improves Body Mass Recovery with Refeeding after Chronic Undernutrition-Induced Muscle Atrophy in Aging Male Rats" Journal of Nutrition. 129: 2264-2270 (1999).
Amirizahdeh et al. "Expression of biologically active recombinant B-domain-deleted human VIII in mammalian cells" Journal of Science, Islamic Republic of Iran. Abstract. 16(2): 103-112 (2005).
Anson et al. "The gene structure of human anti-haemophilic factor IX", The EMBO Journal (1984) 3(5): 1053-1060.
Askoy et al., "A study of the intracellular and secreted forms of the MUC2 mucin from the PC/AA intestinal cell line." Glycobiology 9.7: 739-746 (1999).
Banerji et al. "A lymphocyte-specific cellular enhancer is located downstream of the joining region in immunoglobulin heavy chain genes" Cell 33: 729-740 (1983).
Barker et al. "An immunomagnetic-based method for the purification of ovarian cancer cells from patient-derived ascites." Gynecologic oncology 82.1 (2001): 57-63.
Beeley. Glycoprotein and proteoglycan techniques. vol. 16. Elsevier: 69-72 (1985).
Bengtsson et al. "Treatment of adults with growth hormone (GH) deficiency with recombinant human GH." The Journal of Clinical Endocrinology & Metabolism 76.2 (1993): 309-317.
Berntorp et al. "The pharmacokinetics of clotting factor therapy"; Haemophilia (2003) 9:353-359.
Biller et al. "Effects of once-weekly sustained-release growth hormone: a double-blind, placebo-controlled study in adult growth hormone deficiency." The Journal of Clinical Endocrinology & Metabolism 96.6 (2011): 1718-1726.
Bitter et al. "[33] Expression and secretion vectors for yeast." Methods in enzymology 153 (1987): 516-544.

Bjorkman et al. Pharmacokinetics of Coagulation Factors Clinical Relevance for Patients with Haemophilia. Clin Pharmacokinet vol. 40 (11): 815-832 (2001).
Bohl et al. "Improvement of erythropoiesis in b-thalassemic mice by continuous erythropoietin delivery from muscle" Blood 95.9 (2000): 2793-2798.
Boissel et al. "Erythropoietin structure-function relationships" The Journal of Biological Chemistry 268(21):15983-15993 (1993).
Booth et al. "The use of a 'universal' yeast expression vector to produce an antigenic protein of *Mycobacterium leprae*" Immunol. Lett. 19: 65-70 (1988).
Bouloux, P. M. G., et al. "First human exposure to FSH-CTP in hypogonadotrophic hypogonadal males." Human Reproduction 16.8 (2001): 1592-1597.
Brisson et al. "Expression of a bacterial gene in plants by using a viral vector" Nature, 310: 511-514 (1984).
Broglie et al. "Light-Regulated Expression of a Pea Ribulose-1,5-Bisphosphat Carboxylase Small Subunit Gene in Transformed Plant Cells" Science 224.4648 (1984): 838-843.
Brunetti-Pierri et al. "Bioengineered factor IX molecules with increased catalytic activity improve the therapeutic index of gene therapy vectors for hemophilia B." Human Gene Therapy 20.5 (2009): 479-485.
Buchwald et al. "Long-term, continuous intravenous heparin administration by an implantable infusion pump in ambulatory patients with recurrent venous thrombosis" Surgery 88.4 (1980): 507-516.
Butler et al., "The beta-subunit of human chorionic gonadotrophin exists as a homodimer." Journal of Molecular Endocrinology 22.2: 185-192 (1999).
Byrne et al. "Multiplex gene regulation: A two-tiered approach to transgene regulation in transgenic mice" Proc. Natl. Acad. Sci USA 86:5473-5477 (1989).
Calame et al. "Transcriptional Controlling Elements in the Immunoglobulin and T Cell Receptor Loci" Adv. Immunol 43: 235-275 (1988).
Cawley et al. "Developing long-acting growth hormone formulations." Clinical endocrinology 79.3 (2013): 305-309.
Chan et al. "Plasma Insulin-Like Growth Factor-I and Prostate Cancer Risk: A Prospective Study", Science vol. 279: 563-566, Jan. 1998.
Chen et al. "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).
Chen et al., "Glycoengineering Approach to Half-Life Extension of Recombinant Biotherapeutics." Bioconjugate Chemistry 23.8: 1524-1533 (2012).
Chen et al., "Modulating antibody pharmacokinetics using hydrophilic polymers." Expert Opinion on Drug Delivery 8.9: 1221-1236 (2011).
Chihara, K. "Clinical aspect of growth hormone deficiency in adults." Nihon Naika Gakkai zasshi. The Journal of the Japanese Society of Internal Medicine 89.9 (2000): 2010-2018; with English Abstract.
Claxton et al., "A systematic review of the associations between dose regimens and medication compliance." Clinical Therapeutics 23.8: 1296-1310 (2001).
Coleman, Craig I., et al. "Dosing frequency and medication adherence in chronic disease." Journal of Managed Care Pharmacy 18.7 (2012): 527-539.
Coruzzi et al. "Tissue-specific and light-regulated expression of a pea nuclear gene encoding the small subunit of ribulose-1,5-bisphosphate carboxylase" The EMBO Journal 3.8 (1984): 1671-1680.
Cutfield et al., "Non-compliance with growth hormone treatment in children is common and impairs linear growth." PLoS One 6.1 (2011): e16223.
Dalton, Annamarie C., and William A. Barton. "Over-expression of secreted proteins from mammalian cell lines." Protein Science 23.5 (2014): 517-525.

(56) References Cited

OTHER PUBLICATIONS

Database Geneseq [Online] Apr. 7, 2005, "Human interferon beta (without signal peptide)." XP002664024 retrieved from EBI accession No. GSP: ADW02285, Database accession No. ADW02285.
Database Geneseq [Online] Mar. 24, 2005; "Epogen signal peptide", XP002685292, retrieved from EBI accession No. GSP:ADS64918, Database accession No. ADW649.
Davis CG et al. "Deletion of clustered O-linked carbohydrates does not impair function of low density lipoprotein receptor in transfected fibroblasts" J. Biol. Chem. 26.6 (1986): 2828-2838.
Diederichs et al., "Liposome in kosmetika und arzneimitteln." Pharmazeutische Industrie 56.3 (1994): 267-275.
Diness, et al. Lund-Hansen, and U. Hedner. "Effect of recombinant human FVIIA on warfarin-induced bleeding in rats." Thrombosis research 59.6 (1990): 921-929.
Dong et al. "The prolonged half-lives of new erythropoietin derivatives via peptide addition" Biochemical Research Communications, 339.1 (2006): 380-385.
Drake, William M., et al. "Optimizing GH therapy in adults and children." Endocrine Reviews 22.4 (2001): 425-450.
Edlund, Thomas, et al. "Cell-specific expression of the rat insulin gene: evidence for role of two distinct 5'flanking elements." Science 230.4728 (1985): 912-916.
Eschbach, Joseph W., et al. "Correction of the anemia of end-stage renal disease with recombinant human erythropoietin." New England Journal of Medicine 316.2 (1987): 73-78.
European Search Report Application No. EP 10796803 dated Feb 28, 2013.
European Search Report for Application No. 12150722.2 dated Jun. 4, 2012.
European Search Report for Application No. 07749922 dated Oct. 8, 2009.
European Search Report for Application No. 14196333.0 dated Mar. 2, 2015.
European Search Report for Application No. 14197286.9 dated Mar. 2, 2015.
European Search Report for European Patent Application No. 10796803.4 dated Feb. 28, 2013.
European Search Report for European Patent Application No. 12179805 dated Nov. 9, 2012.
European Search Report for European Patent Application No. 12179821 dated Nov 12, 2012.
Fares "The role of O-linked and N-linked oligosaccharides on the structure—function of glycoprotein hormones: Development of agonists and antagonists", Biochimica et Biophysica Acta (BBA)—General Subjects 1760.4: 560-567 (2006).
Fares et al. "Design of a long-acting follitropin agonist by fusing the C-terminal sequence of the chorionic gonadotropin beta subunit to the follitropin beta subunit" Proc Natl Acad Sci U S A., 89.10: 4304-4308 (May 15, 1992).
Fares et al. "Designing a long-acting human growth hormone (hGH) by fusing the carboxy-terminal peptide of human chorionic gonadotropin B-subunit to the coding sequence of hGH" Endocrinology 15.9: 4410-4417 (2010).
Fares et al. "Growth hormone (GH) retardation of muscle damage due to immobilization in old rats. Possible intervention with a new long-acting recombinant GH" Ann N Y Acad Sci. 786: 430-43 (Jun 15, 1996).
Fares et al. "Designing a Long Acting Erythropoietin by Fusing Three Carboxyl-Terminal Peptides of Human Chorionic Gondotropin [beta] Subunit to the N-Terminal and C-Terminal Coding Sequence", International Journal of Cell Biology, vol. 9, No. 11, pp. 2021-2027 (Jan. 1, 2011).
Fares et al., "Development of a long-acting erythropoietin by fusing the carboxyl-terminal peptide of human chorionic gonadotropin β-subunit to the coding sequence of human erythropoietin." Endocrinology 148.10: 5081-5087 (2007).

Fayad et al. "Update of the MD Anderson Cancer Center experience with hyper-CVAD and rituximab for the treatment of mantle cell and Burkitt-type lymphomas." Clinical Lymphoma and Myeloma 8 (2007): S57-S62.
Fingl et al., "General Principles." The Pharmacological Basis of Therapeutics (ed. Goodman, LS & Gilman, A): 1-46 (1975).
Fogarty, Patrick F. "Biological rationale for new drugs in the bleeding disorders pipeline." ASH Education Program Book 2011.1 (2011): 397-404.
Freshney "Culture of animal cells: a manual of basic technique" (Culture of Animal Cells, A Manual of Basic Technique, Alan R. Liss, Inc., 1983, New York, pp. 1-4).
Fuentes-Prior, Pablo, et al. "Structural basis for the anticoagulant activity of the thrombin-thrombomodulin complex." Nature 404.6777 (2000): 518-525.
Furuhashi et al. "Fusing the carboxy-terminal peptide of the chorionic gonadotropin (CG)-subunit to the common alpha-submit: Retention of O-linked glycosylation and enhanced in vivo bioactivity of chimeric human CG" Molecular Endocrinology 9.1:54-63 (1995).
Furuhashi et al. "Processing of O-linked glycosylation in the chimera consisting of alpha-subunit and carboxyl-terminal peptide of the human chorionic gonadotropin beta-subunit is affected by dimer formation with follicle-stimulating hormone beta-subunit" Endocrine Journal 51.1: 53-59 (2004).
Gao et al., "Erythropoietin gene therapy leads to autoimmune anemia in macaques" Blood 103.9: 3300-3302 (2004).
Garcia-Campayo et al. "Unmasking a new recognition signal for O-linked glycosylation in the chorionic gonadotropin β subunit." Molecular and cellular endocrinology 194.1 (2002): 63-70.
Gardella et al. "Expression of Human Parathyroid Hormone-( I-84) in *Escherichia coli* as a Factor X-cleavable Fusion Protein" Journal of Biological Chemistry 265.26:15854-15859 (1990).
Gellerfors et al. "Characterisation of a secreted form of recombinant derived human growth hormone, expressed in *Escherichia coli* cells", Journal of pharmaceutical and biomedical analysis 7.2: 173-83 (1989).
Ghosh et al., "Activity and regulation of factor VIIa analogs with increased potency at the endothelial cell surface." Journal of Thrombosis and Haemostasis 5.2: 336-346 (2007).
Gilboa et al., "Transfer and Expression of Cloned Genes Using Retroviral Vectors", Biotechniques, vol. 4.6: 504-512 (1986).
Goodson, in "Medical Applications of Controlled Release, vol. II, Applications Evaluation (Langer, RS, et al., Eds.)." (1984): 115-138.
Guitton et al., "Influence of in vitro non-enzymatic glycosylation on the physicochemical parameters of type I collagen." Collagen and Related Research 4.4: 253-264 (1984).
Gurley et al. "Upstream Sequences Required for Efficient Expression of a Soybean Heat Shock Gene" Molecular and cellular biology 6.2 (1986): 559-565.
Hacke et al. "Intravenous thrombolysis with recombinant tissue plasminogen activator for acute hemispheric stroke: the European Cooperative Acute Stroke Study (ECASS)." Jama 274.13 (1995): 1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14.11: 1455-1469 (1996).
Heffernan et al., "Effects of oral administration of a synthetic fragment of human growth hormone on lipid metabolism." American Journal of Physiology—Endocrinology and Metabolism 279.3: E501-E507 (2000).
Houdebine, L., "The methods to generate transgenic animals and to control transgene expression" Journal of Biotechnology 98.2: 145-160 (2002).
Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.
International Search Report and Written Opinion for PCT Application No. PCT/IL09/00700 dated Feb. 4, 2010.

(56) References Cited

OTHER PUBLICATIONS

International Search Report and Written Opinion for PCT Application No. PCT/IL10/00532 dated Apr. 11, 2011.
International Search Report and Written Opinion for PCT Application No. PCT/IL13/50107 dated Jul. 10, 2013.
International Search Report and Written Opinion for PCT Application No. PCT/US07/02767 dated Feb. 15, 2008.
International Search Report and Written Opinion for PCT Application No. PCT/US07/03014 dated Sep. 22, 2008.
International Search Report for Application No. PCTIL2014050910 dated Jan. 25, 2015.
International Search Report for PCT Application No. PCT/IL 12/50288 dated Jan. 28, 2013.
Isgaard et al. "Effects of local administration of GH and IGF-1 on longitudinal bone growth in rats." American Journal of Physiology—Endocrinology and Metabolism 250.4 (1986): E367-E372.
Joshi et al. "Recombinant thyrotropin containing a beta-subunit chimera with the human chorionic gonadotropin-beta carboxy-terminus is biologically active, with a prolonged plasma half-life: role of carbohydrate in bioactivity and metabolic clearance" Endocrinology. 136.9 (1995): 3839-48.
Kanda et al. "Genetic Fusion of an a-subunit Gene to the Follicle-Stimulating Hormone and Chorionic Gonadotropin-b Subunit Genes: Production of a Bifunctional Protein." Molecular Endocrinology 13.11 (1999): 1873-1881.
Kelly et al. "Outcomes of patients with Burkitt lymphoma older than age 40 treated with intensive chemotherapeutic regimens." Clin Lymphoma Myeloma 9.4 (2009): 307-310.
Kessler et al. "Structure and location of the O-glycosidic carbohydrate units of human chorionic gonadotropin." Journal of Biological Chemistry 254.16 (1979): 7909-7914.
Kessler et al., "Structures of N-Glycosidic Carbohydrate Units of Human Chorionic Gonadotropin." Journal of Biological Chemistry 254.16 (1979): 7901-7908.
Kicman et al., "Human chorionic gonadotrophin and sport." British Journal of Sports Medicine 25.2 : 73-80 (1991).
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Kotler et al., "Effects of growth hormone on abnormal visceral adipose tissue accumulation and dyslipidemia in HIV-infected patients." JAIDS Journal of Acquired Immune Deficiency Syndromes 35.3: 239-252 (2004).
Langer Robert "New Methods of Drug Delivery" Science 249.4976: 1527-1533 (1990).
Larsen et al., "Accumulation of magnetic iron oxide nanoparticles coated with variably sized polyethylene glycol in murine tumors." Nanoscale 4.7: 2352-2361 (2012).
Le et al., "Improved Vancomycin Dosing in Children Using Area Under the Curve Exposure." The Pediatric infectious disease journal 32.4 (2013): e155-e163.
Lentz et al., "Posttranslational modification of the carboxy-terminal region of the. beta. subunit of human chorionic gonadotropin." Biochemistry 23.22: 5330-5337 (1984).
Li et al. "Bioassay of hGH .I. Weight gain of hypophysectomized rats". Abstract, Yaowu Fenxi Zazhi 15.2 (1995): 3-7.
Lippin et al. "Human erythropoietin gene therapy for patients with chronic renal failure" Blood 106.7: 2280-2286 (2005).
Lo et al. "The effects of recombinant human growth hormone on body composition and glucose metabolism in HIV-infected patients with fat accumulation." The Journal of Clinical Endocrinology & Metabolism 86.8 (2001): 3480-3487.
Lopez-Berestein, Liposomes in the Therapy of Infectious Disease and Cancer, Lopez-Berestein and Fidler (eds.), Liss, New York, pp. 317-327 (1989).

Lopez-Berestein et al. "Treatment of systemic fungal infections with liposomal amphotericin B." Archives of Internal Medicine 149.11 (1989): 2533-2536.
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
Maston et al., "Chorionic gonadotropin beta subunit [*Homo sapiens*]" NCBI Accession No. AAL69705.1 (Apr. 3, 2002).
Matsumoto et al. "The measurement of low levels of factor VIII or factor IX in hemophilia A and hemophilia B plasma by clot waveform analysis and thrombin generation assay." Journal of thrombosis and haemostasis 4.2 (2006): 377-384.
Matsuo et al. "Thrombolysis by human tissue plasminogen activator and urokinase in rabbits with experimental pulmonary embolus" Nature 291.5816 (1981): 590-591.
Maun et al., "Disulfide locked variants of factor VIIa with a restricted β-strand conformation have enhanced enzymatic activity." Protein Science 14.5: 1171-1180 (2005).
McAlister et al. "NMR analysis of the N-terminal SRCR domain of human CD5: engineering of a glycoprotein for superior characteristics in NMR experiments." Protein Engineering 11.10: 847-853 (1998).
Meulien et al., "Increased biological activity of a recombinant factor IX variant carrying alanine at position+ 1." Protein Engineering 3.7: 629-633 (1990).
Milton et al. "The delineation of a decapeptide gonadotropin-releasing sequence in the carboxyl-terminal extension of the human gonadotropin-releasing hormone precursor." Journal of Biological Chemistry 261.36 (1986): 16990-16997.
Morgan et al. "The amino acid sequence of human chorionic gonadotropin. The alpha subunit and beta subunit." Journal of Biological Chemistry 250.13 (1975): 5247-5258.
Muleo et al. "Small doses of recombinant factor Vila in acquired deficiencies of vitamin K dependent factors." Blood Coagulation & Fibrinolysis Abstract 10.8 (1999): 521-522.
Murray et al. "Dose titration and patient selection increases the efficacy of GH replacement in severely GH deficient adults", Clinical Endocrinology (1999) 50, pp. 749-757.
Mutter et al. "A New Base-Labile Anchoring Group for Polymer-Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Nezu et al. "Treatment of idiopathic pituitary dwarfism with human growth hormone", Journal of Nara Medical Association 40.1(1989): 16-22; with English Abstract.
Ngo et al. "Computational Complexity, Protein Structure Protein Prediction and the Levinthal Paradox" in Birkhauser The Protein Folding Problem and Tertiary Structure Prediction, pp. 433-440 and 492-495 (1994).
Office Action for Japanese Application No. 2014-523441 dated May 24, 2016.
Ogle et al. "Renal effects of growth hormone. I. Renal function and kidney growth." Pediatric Nephrology 6.4 (1992): 394-398.
Oosterhof et al. "Regulation of whole body energy homeostasis with growth hormone replacement therapy and endurance exercise." Physiological genomics 43.12 (2011): 739-748.
Pedrosa et al., "Selective neoglycosylation increases the structural stability of vicilin, the 7S storage globulin from pea seeds." Archives of Biochemistry and Biophysics 382.2: 203-210 (2000).
Persson et al. "Recombinant coagulation factor VIIa—from molecule to clinical aspects of a versatile haemostatic agent", Thrombosis Research (2010) 125: 483-489.
Persson et al., "Rational design of coagulation factor VIIa variants with substantially increased intrinsic activity." Proceedings of the National Academy of Sciences 98.24: 13583-13588 (2001).
Philips A. "The challenge of gene therapy and DNA delivery." Journal of Pharmacy and Pharmacology 53.9 (2001): 1169-1174.
Pierce et al. "Glycoprotein hormones: structure and function." Annual review of biochemistry 50.1: 465-495 (1981).

(56) References Cited

OTHER PUBLICATIONS

Pinkert et al. "An albumin enhancer located 10 kb upstream functions along with its promoter to direct efficient, liver-specific expression in transgenic mice." Genes & development 1.3 (1987): 268-276.
Polizzotti et al. "Effects of saccharide spacing and chain extension on toxin inhibition by glycopolypeptides of well-defined architecture", Macromolecules 40.20:7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Rebois et al., "Hydrodynamic properties of the gonadotropin receptor from a murine Leydig tumor cell line are altered by desensitization." Biochemistry 26.20: 6422-6428 (1987).
Reichel "Sarcosyl-Page: a new electrophoretic method for the separation and immunological detection of PEGylated proteins." Protein Electrophoresis: Methods and Protocols. Humana Press 65-79 (2012).
Reiter et al. "A multicenter study of the efficacy and safety of sustained release GH in the treatment of naive pediatric patients with GH deficiency." The Journal of Clinical Endocrinology & Metabolism 86.10 (2001): 4700-4706.
Ronzi et al. "Optimisation of a freeze-drying process of high purity Factor VIII and Factor IX concentrates." Chemical Engineering and Processing: Process Intensification 42.10 (2003): 751-757.
Rudman et al. "Effects of human growth hormone in men over 60 years old." New England Journal of Medicine 323.1 (1990): 1-6.
Russell et al. "Local Injections of Human or Rat Growth Hormone or of Purified Human Somatomedin-C Stimulate Unilateral Tibial Epiphyseal Growth in Hypophysectomized Rats." Endocrinology 116.6(1985):2563-2567.
Saudek et al "A preliminary trial of the programmable implantable medication system for insulin delivery." New England Journal of Medicine 321.9 (1989): 574-579.
Schein, Catherine H. "The shape of the messenger: Using protein structure information to design novel cytokine-based therapeutics" Abstract; Current Pharmaceutical Design 8.24: 2113-2129 (2002).
Scheuttrumpf et al., "Factor IX variants improve gene therapy efficacy for hemophilia B." Blood 105.6: 2316-2323 (2005).
Schulte "Half-life extension through albumin fusion technologies", Thrombosis Research (2009) 124 Suppl. 2; S6-S8.
Sefton, "Implantable pumps." Critical Reviews in Biomedical Engineering 14.3: 201-240 (1986).
Sheffield et al. "Effects of genetic fusion of factor IX to albumin on in vivo clearance in mice and rabbits", Blackwell Publishing Ltd, British Journal of Haematology (2004) 126.4: 565-573.
Silverman et al. "A long-acting human growth hormone (Nutropin Depot): Efficacy and safety following two years of treatment in children with growth hormone deficiency" J Pediatr Endocrinol Metab.15 Suppl 2: 715-722. (May 2002).
Smeland et al. "Treatment of Burkitt's/Burkitt-like lymphoma in adolescents and adults: a 20-year experience from the Norwegian Radium Hospital with the use of three successive regimens." Annals of Oncology 15.7 (2004): 1072-1078.
Speiser et al. "Optimization of spray-dried and -congealed lipid micropellets and characterization of their surface morphology." Pharm. Res. 8.1 : 47-54 (1991).
Srour et al. "Regulation of human factor IX expression using doxycycline-inducible gene expression system." Thromb Haemost 90.3: 398-405 (2003).
Studier F.W. et al "Use of T7 RNA Polymerase to Direct Expression of Cloned Genes." Methods in Enzymol. 185: 60-89 (1990).
Su et al. "Curcumin Inhibits Human Lung Cell Carcinoma Cancer Tumour Growth in a Murine Xenograft Model" Phytotherapy Research 24.2 (2010): 189-192.
Sugahara et al. "Characterization of the O-glycosylation sites in the chorionic gonadotropin β subunit in vivo using site-directed mutagenesis and gene transfer." Journal of Biological Chemistry 271.34: 20797-20804 (1996).

Supplementary European Search Report for Application No. 13749077.7 dated Oct. 22, 2015.
Supplementary European Search Report for Application No. 12819794.4 dated Feb. 24, 2015.
Supplementary European Search Report for EP patent application No. 09797630.2, dated Dec. 5, 2011.
Takamatsu et al. "Expression of bacterial chloramphenicol acetyltransferase gene in tobacco plants mediated by TMV-RNA" The EMBO Journal 6.2: 307-311 (1987).
Treat, J, Greenspan, AR, and Rahman, A. "Liposome Encapsulated Doxorubicin—Preliminary Results of Phase I and Phase II Trials." in: G Lopez-Berestein, IJ Fidler (Eds.) Liposomes in the Therapy of Infectious Diseases and Cancer. Alan R. Liss, New York; 1989: 353-365.
Uenalp et al. "Factor VII deficiency associated with valproate treatment" Pediatrics International 50.3:403-405 Abstract (2008).
Venn et al. "Biosynthesis and metabolism in vivo of intervertebral-disc proteoglycans in the mouse." Biochemical Journal 215.2 (1983): 217-225.
Weiss et al. "Noncompliance in Neurologic Patients" Current Treatment Options in Neurology 7.5: 419-425 (2005).
Weissbach and Weissbach, "Methods for Plant Molecular Biology." Selected Methods in Enzymology (USA) Section VIII: 421-463 (1988).
Wells, J.A, "Additivity of Mutational Effects in Proteins" Biochemistry 29.37: 8509-8517 (1990).
White et al. "Mammalian Recombinant Coagulation Proteins: Structure and Function", Transfus. Sci. (1998) 19.2: 177-189.
Wildt et al., "The humanization of N-glycosylation pathways in yeast." Nature Reviews Microbiology 3.2: 119-128 (2005).
Wilken et al. "A novel four-amino acid determinant defines conformational freedom within chorionic gonadotropin β-subunits." Biochemistry 46.14: 4417-4424 (2007).
Winoto et al. "A novel, inducible and T cell-specific enhancer located at the 3' end of the T cell receptor alpha locus" EMBO J. 8.3: 729-733 (1989).
Wynne et al. "Subcutaneous oxyntomodulin reduces body weight in overweight and obese subjects a double-blind, randomized, controlled trial." Diabetes 54.8 (2005): 2390-2395.
Yefenof & McConnell "Interferon amplifies complement activation by Burkitt's lymphoma cells." Nature. Feb. 21-27, 1985; 313(6004):68.
Yin et al. "Recombinant human growth hormone replacement therapy in HIV-associated wasting and visceral adiposity". Exper. Rev. Anti-Infect. Ther. 3.5: 727-736 (2005).
Zheng et al., "The impact of glycosylation on monoclonal antibody conformation and stability." MAbs. vol. 3. No. 6. Landes Bioscience (Nov.-Dec. 2011), pp. 568-576.
Zhong et al. "The N-terminal epidermal growth factor-like domain in factor IX and factor X represents an important recognition motif for binding to tissue factor." J. Biol. Chem. (2002) 277.5: 3622-3631.
Alberts et al, "Molecular biology of the cell", 5th ed.(Garland Science, 2008). 2002, p. 367.
Anonymous "Prolor Biotech Announces Positive Results of its Obesity/Diabetes Drug Candidate in Preclinical Weight Loss Study", Apr. 17, 2012, pp. 1-2: Retrieved from the Internet: URL;http://web.archive.org/web/20120526154526/http://www.prolor-biotech.com/_Uploads/dbsAttachedFiles/NewsPROLORAnnouncesObesityDiabetesStudyResults.pdf.
Anonymous "Prolor Biotech Receives New U.S. Patent Allowance Covering Broad Applications of its CTP Platform for Long Acting Therapeutic Proteins", Jul. 11, 2011, pp. 1-2; Retrieved from the Internet: URL;http://web.archive.org/web/20110725053527/http://www.prolor-biotech.com/_Uploads/dbsAttachedFiles/NewsPROLORAnnouncesAllowanceOfNewCTP-PlatformPatentByUSPatentOffice.pdf.
Anonymous "Corporate Presentation—Lazard Capital Markets Healthcare Conference", Nov. 15, 2011, pp. 1-19; Retrieved from

(56) References Cited

OTHER PUBLICATIONS the Internet: URL:http://web.archive.org/web/20110628023057/ http://www.prolor-biotech.com/_Uploads/dbsAttachedFiles/prolorInvestorsNov2011.pdf.

Anonymous "Corporate Presentation", Jun. 1, 2011, pp. 1-35; Retrieved from the Internet: URL;http://web.archive.org/web/20110628023057/http://www.prolor-biotech.com/_Uploads/dbsAttachedFiles/prolorPresentationJune2011Investors.pdf.

Anonymous "PROLOR and Yeda enter definitive license agreement for Reversible PEGylation technology", Jan. 18, 2011; pp. 1-3; Retrieved from the Internet: URL;http://web.archive.org/web/20110123063420/http://www.news-medical.net/news/20110118/PROLOR-and-Yeda-enter-definitive-license-agreement-for-Reversible-PEGylation-technology.aspx.

Cohen et al, "Oxyntomodulin suppresses appetite and reduces food intake in humans", J Clin Endocrinol Metab. Oct. 2003:88(10):4696-701.

Genbank Accession No. NP 002045 (version 1), Sep. 6, 2014.

Havron et al. "OR2, 8 Phase I PK&PD profile of long acting bio-better CTP modified hGH (MOD-4023) in healthy volunteers"Growth Hormone & IGF Research. Jan. 1, 2010;20:S4-5.

Kieffer at al, "Distribution of glucagon receptors on hormone-specific endocrine cells of rat pancreatic islets" Endocrinology. Nov. 1996:137(11):5119-25.

Pocai et al. "Glucagon-Like Peptide 1/Glucagon Receptor Dual Agonism Reverses Obesity in Mice", Diabetes, vol. 58, Oct. 2009, pp. 2258-2266.

Schneider KH "GMP Requirements for master and working cell bank" Pharmazeutische Industrie, Jan. 1, 2005;67(11):1366-9.

Shechter et al. "Reversible PEGylation of peptide YY3-36 prolongs its inhibition of food intake in mice", FEBS Lett. Apr. 25, 2005;579(11):2439-44.

Takeya et al. "Bovine factor VII. Its purification and complete amino acid sequence". Journal of Biological Chemistry, Oct. 15, 1988;263(29)1 4868-77.

Bjorkman et al. "Pharmacokinetic of Coagulation Factors", 2001: 40 (11): 815-832.

European Search Report for European Application No. 17161199.9 dated Aug. 7, 2017.

International Search Report for PCT/IL2017/050645 dated Sep. 21, 2017.

International Search Report for PCT/IL2017/050784 dated Sep. 22, 2017.

* cited by examiner

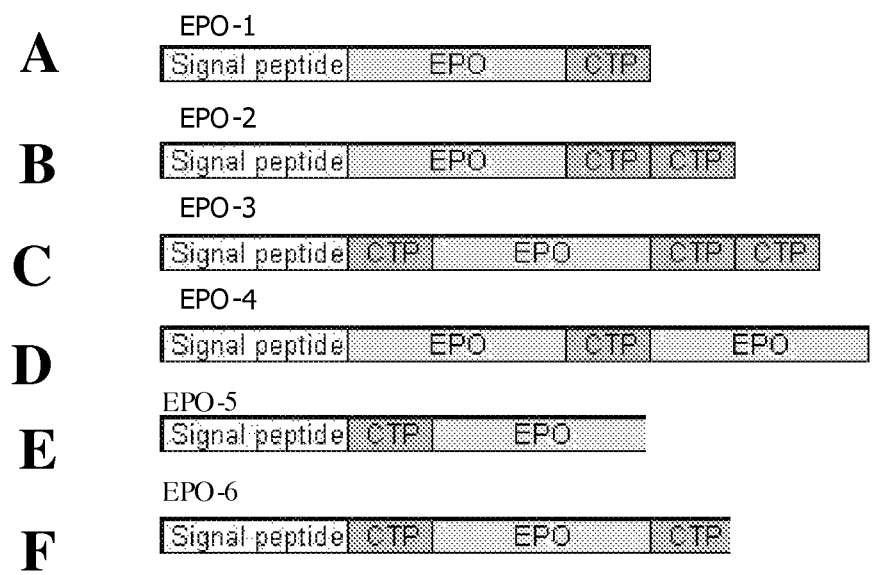
Figures 1A-F
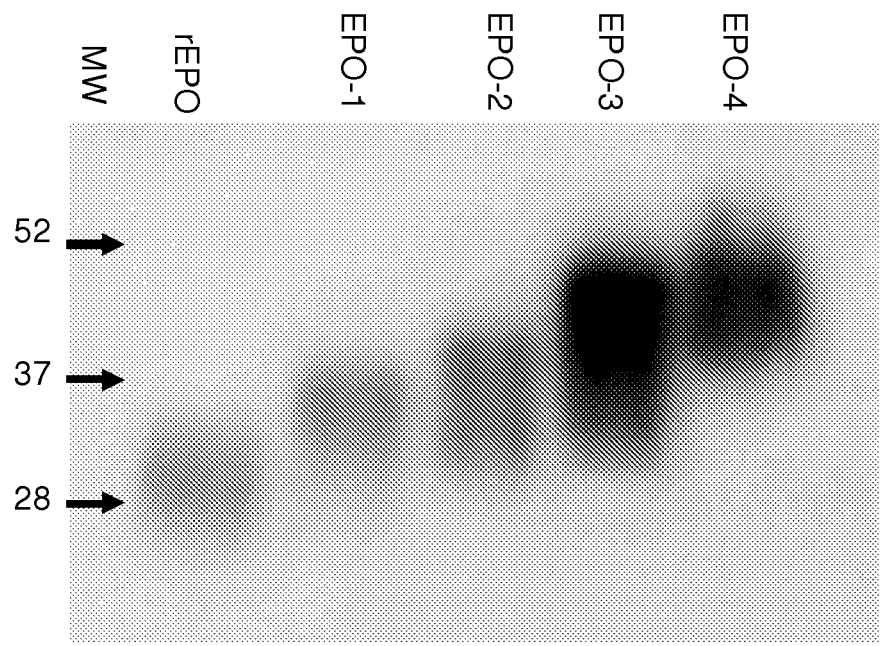
Figure 2

SEQUENCE LISTING

```
<160> NUMBER OF SEQ ID NOS: 51

<210> SEQ ID NO 1
<211> LENGTH: 221
<212> TYPE: PRT
<213> ORGANISM: Homo sapiens

<400> SEQUENCE: 1

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110
```

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln
    210                 215                 220

<210> SEQ ID NO 2
<211> LENGTH: 249
<212> TYPE: PRT
<213> ORGANISM: Homo sapiens

<400> SEQUENCE: 2

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ser Ser Ser
    210                 215                 220

Ser Lys Ala Pro Pro Ser Leu Pro Ser Pro Ser Arg Leu Pro Gly
225                 230                 235                 240

Pro Ser Asp Thr Pro Ile Leu Pro Gln
                245

```
<210> SEQ ID NO 3
<211> LENGTH: 277
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
            20                  25                  30

Ala Pro Pro Pro Ser Leu Pro Ser Pro Ser Arg Leu Pro Gly Pro Ser
        35                  40                  45

Asp Thr Pro Ile Leu Pro Gln Ala Pro Arg Leu Ile Cys Asp Ser
    50                  55                  60

Arg Val Leu Glu Arg Tyr Leu Leu Glu Ala Lys Glu Ala Glu Asn Ile
65              70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg Ser Ser Ser
    210                 215                 220

Ser Lys Ala Pro Pro Ser Leu Pro Ser Pro Ser Arg Leu Pro Gly
225                 230                 235                 240

Pro Ser Asp Thr Pro Ile Leu Pro Gln Ser Ser Ser Ser Lys Ala Pro
                245                 250                 255

Pro Pro Ser Leu Pro Ser Pro Ser Arg Leu Pro Gly Pro Ser Asp Thr
            260                 265                 270

Pro Ile Leu Pro Gln
        275

<210> SEQ ID NO 4
<211> LENGTH: 387
<212> TYPE: PRT
<213> ORGANISM: Homo sapiens

<400> SEQUENCE: 4

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
```

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg Ser Ser Ser Lys Ala Pro Pro Ser Leu Pro Ser Pro Ser
            195                 200                 205

Arg Leu Pro Gly Pro Ser Asp Thr Pro Ile Leu Pro Gln Ala Pro Pro
210                 215                 220

Arg Leu Ile Cys Asp Ser Arg Val Leu Glu Arg Tyr Leu Leu Glu Ala
225                 230                 235                 240

Lys Glu Ala Glu Asn Ile Thr Thr Gly Cys Ala Glu His Cys Ser Leu
                245                 250                 255

Asn Glu Asn Ile Thr Val Pro Asp Thr Lys Val Asn Phe Tyr Ala Trp
                260                 265                 270

Lys Arg Met Glu Val Gly Gln Gln Ala Val Glu Val Trp Gln Gly Leu
            275                 280                 285

Ala Leu Leu Ser Glu Ala Val Leu Arg Gly Gln Ala Leu Leu Val Asn
        290                 295                 300

Ser Ser Gln Pro Trp Glu Pro Leu Gln Leu His Val Asp Lys Ala Val
305                 310                 315                 320

Ser Gly Leu Arg Ser Leu Thr Thr Leu Leu Arg Ala Leu Gly Ala Gln
                325                 330                 335

Lys Glu Ala Ile Ser Pro Pro Asp Ala Ala Ser Ala Ala Pro Leu Arg
                340                 345                 350

Thr Ile Thr Ala Asp Thr Phe Arg Lys Leu Phe Arg Val Tyr Ser Asn
            355                 360                 365

Phe Leu Arg Gly Lys Leu Lys Leu Tyr Thr Gly Glu Ala Cys Arg Thr
        370                 375                 380

Gly Asp Arg
385

<210> SEQ ID NO 5
<211> LENGTH: 221
<212> TYPE: PRT
<213> ORGANISM: Homo sapiens

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Lys
            20                  25                  30

Ala Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
 50                  55                  60

Arg Val Leu Glu Arg Tyr Leu Leu Glu Ala Lys Glu Ala Glu Asn Ile
 65                  70                  75                  80

Thr Thr Gly Cys Ala Glu His Cys Ser Leu Asn Glu Asn Ile Thr Val
                 85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg
    210                 215                 220

<210> SEQ ID NO 6
<211> LENGTH: 249
<212> TYPE: PRT
<213> ORGANISM: Homo sapiens

<400> SEQUENCE: 6

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ser Ser Ser Ser Lys
            20                  25                  30

Ala Pro Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
 50                  55                  60

Arg Val Leu Glu Arg Tyr Leu Leu Glu Ala Lys Glu Ala Glu Asn Ile
 65                  70                  75                  80

Thr Thr Gly Cys Ala Glu His Cys Ser Leu Asn Glu Asn Ile Thr Val
                 85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

```
Phe Arg Lys Leu Phe Arg Val Tyr Ser Asn Phe Leu Arg Gly Lys Leu
            195                 200                 205

Lys Leu Tyr Thr Gly Glu Ala Cys Arg Thr Gly Asp Arg Ser Ser Ser
    210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
                245

<210> SEQ ID NO 7
<211> LENGTH: 25
<212> TYPE: DNA
<213> ORGANISM: Artificial
<220> FEATURE:
<223> OTHER INFORMATION: Forward primer for EPO-CTP constructs

<400> SEQUENCE: 7
aatctagagg tcatcatggg ggtgc                                       25

<210> SEQ ID NO 8
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 8
attgcggccg cggatccaga agacctttat tg                               32

<210> SEQ ID NO 9
<211> LENGTH: 25
<212> TYPE: DNA
<213> ORGANISM: Artificial
<220> FEATURE:
<223> OTHER INFORMATION: Reverse primer for EPO-CTP constructs

<400> SEQUENCE: 9
taaatattgg ggtgtccgag ggccc                                       25

<210> SEQ ID NO 10
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 10
ccaatattac cacaagcccc accacgcctc at                               32

<210> SEQ ID NO 11
<211> LENGTH: 35
<212> TYPE: DNA
<213> ORGANISM: Artificial
<220> FEATURE:
<223> OTHER INFORMATION: Reverse primer for EPO-CTP constructs

<400> SEQUENCE: 11
tgcggccgcg gatccttatc tgtcccctgt cctgc                            35

<210> SEQ ID NO 12
<211> LENGTH: 17
<212> TYPE: DNA
<213> ORGANISM: Artificial
<220> FEATURE:
```

```
<223> OTHER INFORMATION: Forward primer for EPO-CTP constructs

<400> SEQUENCE: 12
gccctgctgt cggaagc                                                          17

<210> SEQ ID NO 13
<211> LENGTH: 32
<212> TYPE: DNA
<213> ORGANISM: Artificial
<220> FEATURE:
<223> OTHER INFORMATION: Reverse primer for EPO-CTP constructs

<400> SEQUENCE: 13
attgcggccg cggatccaga agacctttat tg                                         32

<210> SEQ ID NO 14
<211> LENGTH: 32
<212> TYPE: DNA
<213> ORGANISM: Artificial
<220> FEATURE:
<223> OTHER INFORMATION: Reverse primer for EPO-CTP constructs

<400> SEQUENCE: 14
ctttgaggaa gaggagccca ggactgggag gc                                         32

<210> SEQ ID NO 15
<211> LENGTH: 24
<212> TYPE: DNA
<213> ORGANISM: Artificial
<220> FEATURE:
<223> OTHER INFORMATION: Forward primer for EPO-CTP constructs

<400> SEQUENCE: 15
cctgggctcc tcttcctcaa aggc                                                  24

<210> SEQ ID NO 16
<211> LENGTH: 193
<212> TYPE: PRT
<213> ORGANISM: Homo sapiens

<400> SEQUENCE: 16
```

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

```
Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
        180                 185                 190

Arg

<210> SEQ ID NO 17
<211> LENGTH: 34
<212> TYPE: PRT
<213> ORGANISM: Artificial
<220> FEATURE:
<223> OTHER INFORMATION: CTP amino acid sequence

<400> SEQUENCE: 17

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

Pro Gln

<210> SEQ ID NO 18
<211> LENGTH: 28
<212> TYPE: PRT
<213> ORGANISM: Artificial
<220> FEATURE:
<223> OTHER INFORMATION: CTP amino acid sequence

<400> SEQUENCE: 18

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 19
<211> LENGTH: 27
<212> TYPE: PRT
<213> ORGANISM: Homo sapiens

<400> SEQUENCE: 19

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 20
<211> LENGTH: 786
<212> TYPE: DNA
<213> ORGANISM: Homo sapiens

<400> SEQUENCE: 20
tctagaggtc atcatggggg tgcacgaatg tcctgcctgg ctgtggcttc tcctgtccct    60
tctgtcgctc cctctgggcc tcccagtcct gggctcctct tcctcaaagg ccctcccccc   120
gagccttcca gtccatccc  gactcccggg gccctcggac accccaatat taccacaagc   180
cccaccacgc ctcatctgtg acagccgagt cctggagagg tacctcttgg aggccaagga   240
ggccgagaat atcacgacgg gctgtgctga cactgcagc  ttgaatgaga atatcactgt   300
cccagacacc aaagttaatt tctatgcctg gaagaggatg gaggtcgggc agcaggccgt   360
agaagtctgg caggg cctgg ccctgctgtc ggaagctgtc ctgcggggcc aggccctgtt   420
```

```
ggtcaactct tcccagccgt gggagcccct gcagctgcat gtggataaag ccgtcagtgg    480
ccttcgcagc ctcaccactc tgcttcgggc tctgggagcc agaaggaag ccatctcccc     540 tccagatgcg gcctcagctg ctccactccg aacaatcact gctgacactt tccgcaaact    600
cttccgagtc tactccaatt tcctccgggg aaagctgaag ctgtacacag gggaggcctg    660
caggacaggg gacagatcct cttcctcaaa ggcccctccc ccgagccttc caagtccatc    720
ccgactcccg ggccctcgg acaccccgat cctcccacaa taaaggtctt ctggatccgc     780
ggccgc                                                              786
```

```
<210> SEQ ID NO 21
<211> LENGTH: 873
<212> TYPE: DNA
<213> ORGANISM: Homo sapiens

<400> SEQUENCE: 21
tctagaggtc atcatggggg tgcacgaatg tcctgcctgg ctgtggcttc tcctgtccct     60
tctgtcgctc cctctgggcc tcccagtcct gggctcctct tcctcaaagg cccctccccc    120
gagccttcca gtccatccc gactcccggg gccctcggac accccaatat taccacaagc    180
cccaccacgc tcatctgtg acagccgagt cctggagagg tacctcttgg aggccaagga    240
ggccgagaat atcacgacgg gctgtgctga acactgcagc ttgaatgaga atatcactgt    300
cccagacacc aaagttaatt tctatgcctg gaagaggatg gaggtcgggc agcaggccgt    360
agaagtctgg cagggcctgg ccctgctgtc ggaagctgtc ctgcgggc aggccctgtt    420 ggtcaactct tcccagccgt gggagcccct gcagctgcat gtggataaag ccgtcagtgg    480
ccttcgcagc ctcaccactc tgcttcgggc tctgggagcc agaaggaag ccatctcccc     540 tccagatgcg gcctcagctg ctccactccg aacaatcact gctgacactt tccgcaaact    600
cttccgagtc tactccaatt tcctccgggg aaagctgaag ctgtacacag gggaggcctg    660
caggacaggg gacagatcct cttcctcaaa ggcccctccc ccgagccttc caagtccatc    720
ccgactcccg ggccctccg acacaccaat cctgccacag agcagctcct ctaaggcccc    780
tcctccatcc ctgccatccc cctcccggct gcctggcccc tctgacaccc ctatcctgcc    840
tcagtgatga aggtcttctg gatccgcggc cgc                                 873
```

```
<210> SEQ ID NO 22
<211> LENGTH: 221
<212> TYPE: PRT
<213> ORGANISM: Homo sapiens

<400> SEQUENCE: 22
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Ser Gln Ala Leu Leu Val Asn Ser Ser

```
                100                 105                 110
Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln
    210                 215                 220
```

<210> SEQ ID NO 23
<211> LENGTH: 217
<212> TYPE: PRT
<213> ORGANISM: Homo sapiens

<400> SEQUENCE: 23

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 24
<211> LENGTH: 166
<212> TYPE: PRT
<213> ORGANISM: Homo sapiens

```
<400> SEQUENCE: 24

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 25
<211> LENGTH: 30
<212> TYPE: PRT
<213> ORGANISM: Homo sapiens

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 26
<211> LENGTH: 21
<212> TYPE: PRT
<213> ORGANISM: Homo sapiens

<400> SEQUENCE: 26

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 27
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 27
ctctagagga catggccac                                              19

<210> SEQ ID NO 28
<211> LENGTH: 24
<212> TYPE: DNA
```

```
<213> ORGANISM: Artificial
<220> FEATURE:
<223> OTHER INFORMATION: Reverse primer for HGH-CTP constructs

<400> SEQUENCE: 28
acagggaggt ctgggggttc tgca                                          24

<210> SEQ ID NO 29
<211> LENGTH: 26
<212> TYPE: DNA
<213> ORGANISM: Artificial
<220> FEATURE:
<223> OTHER INFORMATION: Forward primer for HGH-CTP constructs

<400> SEQUENCE: 29
tgcagaaccc ccagacctcc ctgtgc                                        26

<210> SEQ ID NO 30
<211> LENGTH: 22
<212> TYPE: DNA
<213> ORGANISM: Artificial
<220> FEATURE:
<223> OTHER INFORMATION: Reverse primer for HGH-CTP constructs

<400> SEQUENCE: 30
ccaaactcat caatgtatct ta                                            22

<210> SEQ ID NO 31
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 31
ctctagagga catggccac                                                19

<210> SEQ ID NO 32
<211> LENGTH: 25
<212> TYPE: DNA
<213> ORGANISM: Artificial
<220> FEATURE:
<223> OTHER INFORMATION: Reverse primer for HGH-CTP constructs

<400> SEQUENCE: 32
cgaactcctg gtaggtgtca aaggc                                         25

<210> SEQ ID NO 33
<211> LENGTH: 25
<212> TYPE: DNA
<213> ORGANISM: Artificial
<220> FEATURE:
<223> OTHER INFORMATION: Forward primer for HGH-CTP constructs

<400> SEQUENCE: 33
gcctttgaca cctaccagga gttcg                                         25

<210> SEQ ID NO 34
<211> LENGTH: 33
<212> TYPE: DNA
<213> ORGANISM: Artificial
<220> FEATURE:
<223> OTHER INFORMATION: NotI Reverse primer for HGH-CTP constructs

<400> SEQUENCE: 34
acgcggccgc atccagacct tcatcactga ggc                                33
```

<210> SEQ ID NO 35
<211> LENGTH: 34
<212> TYPE: DNA
<213> ORGANISM: Artificial
<220> FEATURE:
<223> OTHER INFORMATION: Reverse primer for HGH-CTP constructs

<400> SEQUENCE: 35
gcggccgcgg actcatcaga agccgcagct gccc                34

<210> SEQ ID NO 36
<211> LENGTH: 217
<212> TYPE: PRT
<213> ORGANISM: Homo sapiens

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 37
<211> LENGTH: 245
<212> TYPE: PRT
<213> ORGANISM: Homo sapiens

<400> SEQUENCE: 37

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

```
Leu Ala Phe Asp Thr Tyr Gln Glu Phe Glu Ala Tyr Ile Pro Lys
        50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
                180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Ser Ser Ser Lys Ala Pro
210                 215                 220

Pro Pro Ser Leu Pro Ser Pro Ser Arg Leu Pro Gly Pro Ser Asp Thr
225                 230                 235                 240

Pro Ile Leu Pro Gln
                245

<210> SEQ ID NO 38
<211> LENGTH: 273
<212> TYPE: PRT
<213> ORGANISM: Homo sapiens

<400> SEQUENCE: 38

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
             35                  40                  45

Leu Ala Phe Asp Thr Tyr Gln Glu Phe Glu Glu Ala Tyr Ile Pro Lys
         50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
```

```
              165                 170                 175
His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Ser Ser Ser Lys Ala Pro
            210                 215                 220

Pro Pro Ser Leu Pro Ser Pro Ser Arg Leu Pro Gly Pro Ser Asp Thr
225                 230                 235                 240

Pro Ile Leu Pro Gln Ser Ser Ser Lys Ala Pro Pro Ser Leu
            245                 250                 255

Pro Ser Pro Ser Arg Leu Pro Gly Pro Ser Asp Thr Pro Ile Leu Pro
            260                 265                 270

Gln

<210> SEQ ID NO 39
<211> LENGTH: 301
<212> TYPE: PRT
<213> ORGANISM: Homo sapiens

<400> SEQUENCE: 39

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
            195                 200                 205

Ala Leu Leu Lys Asn Tyr Gly Leu Leu Tyr Cys Phe Arg Lys Asp Met
            210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Ser Leu
                245                 250                 255

Pro Ser Pro Ser Arg Leu Pro Gly Pro Ser Asp Thr Pro Ile Leu Pro
```

```
                    260                 265                 270
Gln Ser Ser Ser Lys Ala Pro Pro Ser Leu Pro Ser Pro Ser
            275                 280                 285

Arg Leu Pro Gly Pro Ser Asp Thr Pro Ile Leu Pro Gln
        290                 295                 300

<210> SEQ ID NO 40
<211> LENGTH: 285
<212> TYPE: PRT
<213> ORGANISM: Homo sapiens

<400> SEQUENCE: 40

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Phe Pro Thr Ile Pro Leu Ser Arg Leu Phe
            35                  40                  45

Asp Asn Ala Met Leu Arg Ala His Arg Leu His Gln Leu Ala Phe Asp
    50                  55                  60

Thr Tyr Gln Glu Phe Glu Glu Ala Tyr Ile Pro Lys Glu Gln Lys Tyr
65                  70                  75                  80

Ser Phe Leu Gln Asn Pro Gln Thr Ser Leu Cys Phe Ser Glu Ser Ile
                85                  90                  95

Pro Thr Pro Ser Asn Arg Glu Glu Thr Gln Gln Lys Ser Asn Leu Glu
            100                 105                 110

Leu Leu Arg Ile Ser Leu Leu Leu Ile Gln Ser Trp Leu Glu Pro Val
        115                 120                 125

Gln Phe Leu Arg Ser Val Phe Ala Asn Ser Leu Val Tyr Gly Ala Ser
    130                 135                 140

Asp Ser Asn Val Tyr Asp Leu Leu Lys Asp Leu Glu Glu Gly Ile Gln
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
            180                 185                 190

Ala Leu Leu Lys Asn Tyr Gly Leu Leu Tyr Cys Phe Arg Lys Asp Met
        195                 200                 205

Asp Lys Val Glu Thr Phe Leu Arg Ile Val Gln Cys Arg Ser Val Glu
    210                 215                 220

Gly Ser Cys Gly Phe Ser Ser Ser Lys Ala Pro Pro Pro Ser Leu
225                 230                 235                 240

Pro Ser Pro Ser Arg Leu Pro Gly Pro Ser Asp Thr Pro Ile Leu Pro
                245                 250                 255

Gln Ser Ser Ser Ser Lys Ala Pro Pro Pro Ser Leu Pro Ser Pro Ser
            260                 265                 270

Arg Leu Pro Gly Pro Ser Asp Thr Pro Ile Leu Pro Gln
        275                 280                 285

<210> SEQ ID NO 41
<211> LENGTH: 273
<212> TYPE: PRT
<213> ORGANISM: Homo sapiens

<400> SEQUENCE: 41

Met Ala Thr Gly Ser Arg Thr Ser Leu Leu Leu Ala Phe Gly Leu Leu
```

```
            1               5                  10                 15
Cys Leu Pro Trp Leu Gln Glu Gly Ser Ala Ser Ser Ser Lys Ala
            20                 25                 30

Pro Pro Pro Ser Leu Pro Ser Pro Ser Arg Leu Pro Gly Pro Ser Asp
            35                 40                 45

Thr Pro Ile Leu Pro Gln Phe Pro Thr Ile Pro Leu Ser Arg Leu Phe
         50                 55                 60

Asp Asn Ala Met Leu Arg Ala His Arg Leu His Gln Leu Ala Phe Asp
65                  70                 75                  80

Thr Tyr Gln Glu Phe Glu Glu Ala Tyr Ile Pro Lys Glu Gln Lys Tyr
         85                 90                 95

Ser Phe Leu Gln Asn Pro Gln Thr Ser Leu Cys Phe Ser Glu Ser Ile
             100                105                110

Pro Thr Pro Ser Asn Arg Glu Glu Thr Gln Gln Lys Ser Asn Leu Glu
             115                120                125

Leu Leu Arg Ile Ser Leu Leu Leu Ile Gln Ser Trp Leu Glu Pro Val
         130                135                140

Gln Phe Leu Arg Ser Val Phe Ala Asn Ser Leu Val Tyr Gly Ala Ser
145                 150                155                 160

Asp Ser Asn Val Tyr Asp Leu Leu Lys Asp Leu Glu Glu Gly Ile Gln
                165                170                175

Thr Leu Met Gly Arg Leu Glu Asp Gly Ser Pro Arg Thr Gly Gln Ile
             180                185                190

Phe Lys Gln Thr Tyr Ser Lys Phe Asp Thr Asn Ser His Asn Asp Asp
         195                200                205

Ala Leu Leu Lys Asn Tyr Gly Leu Leu Tyr Cys Phe Arg Lys Asp Met
         210                215                220

Asp Lys Val Glu Thr Phe Leu Arg Ile Val Gln Cys Arg Ser Val Glu
225                 230                235                 240

Gly Ser Cys Gly Phe Ser Ser Ser Lys Ala Pro Pro Ser Leu
                245                250                255

Pro Ser Pro Ser Arg Leu Pro Gly Pro Ser Asp Thr Pro Ile Leu Pro
             260                265                270

Gln

<210> SEQ ID NO 42
<211> LENGTH: 245
<212> TYPE: PRT
<213> ORGANISM: Homo sapiens

<400> SEQUENCE: 42

Met Ala Thr Gly Ser Arg Thr Ser Leu Leu Leu Ala Phe Gly Leu Leu
1               5                  10                 15

Cys Leu Pro Trp Leu Gln Glu Gly Ser Ala Ser Ser Ser Lys Ala
            20                 25                 30

Pro Pro Pro Ser Leu Pro Ser Pro Ser Arg Leu Pro Gly Pro Ser Asp
            35                 40                 45

Thr Pro Ile Leu Pro Gln Phe Pro Thr Ile Pro Leu Ser Arg Leu Phe
         50                 55                 60

Asp Asn Ala Met Leu Arg Ala His Arg Leu His Gln Leu Ala Phe Asp
65                  70                 75                  80

Thr Tyr Gln Glu Phe Glu Glu Ala Tyr Ile Pro Lys Glu Gln Lys Tyr
         85                 90                 95

Ser Phe Leu Gln Asn Pro Gln Thr Ser Leu Cys Phe Ser Glu Ser Ile
```

```
                100                 105                 110
Pro Thr Pro Ser Asn Arg Glu Glu Thr Gln Gln Lys Ser Asn Leu Glu
            115                 120                 125

Leu Leu Arg Ile Ser Leu Leu Ile Gln Ser Trp Leu Glu Pro Val
        130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
                215                 220

Asp Lys Val Glu Thr Phe Leu Arg Ile Val Gln Cys Arg Ser Val Glu
225                 230                 235                 240

Gly Ser Cys Gly Phe
            245

<210> SEQ ID NO 43
<211> LENGTH: 12
<212> TYPE: PRT
<213> ORGANISM: Artificial
<220> FEATURE:
<223> OTHER INFORMATION: CTP amino acid sequence

<400> SEQUENCE: 43

Ser Ser Ser Ser Lys Ala Pro Pro Pro Ser Leu Pro
1               5                   10

<210> SEQ ID NO 44
<211> LENGTH: 853
<212> TYPE: DNA
<213> ORGANISM: Homo sapiens

<400> SEQUENCE: 44
tctagaggac atggccaccg gcagcaggac cagcctgctg ctggccttcg gcctgctgtg      60
cctgccatgg ctgcaggagg cagcgccag ctcttcttct aaggctccac ccccatctct     120
gcccagcccc agcagactgc cgggcccag cgacacaccc attctgcccc agttccccac     180 catcccctg agcaggctgt tcgacaacgc catgctgagg gctcacaggc tgcaccagct     240
ggcctttgac acctaccagg agttcgagga agcctacatc cccaaggagc agaagtacag     300
cttcctgcag aaccccaga cctccctgtg cttcagcgag agcatcccca ccccagcaa     360 cagagaggag acccagcaga agagcaacct ggagctgctg aggatctccc tgctgctgat     420
ccagagctgg ctggagcccg tgcagttcct gagaagcgtg ttcgccaaca gcctggtgta     480
cggcgccagc gacagcaacg tgtacgacct gctgaaggac ctggaggag gcatccagac     540 cctgatgggc cggctggagg acggcagccc caggaccggc cagatcttca gcagaccta     600 cagcaagttc gacaccaaca gccacaacga cgacgccctg ctgaagaact acgggctgct     660
gtactgcttc agaaaggaca tggacaaggt ggagaccttc ctgaggatcg tgcagtgcag     720
aagcgtggag ggcagctgcg gcttcagctc cagcagcaag gcccctcccc cgagcctgcc     780
ctccccaagc aggctgcctg ggccctccga cacaccaatc ctgcctcagt gatgaaggtc     840
tggatgcggc cgc                                                      853
```

<210> SEQ ID NO 45
<211> LENGTH: 937
<212> TYPE: DNA
<213> ORGANISM: Homo sapiens

<400> SEQUENCE: 45

```
tctagaggac atggccaccg gcagcaggac cagcctgctg ctggccttcg gcctgctgtg      60
cctgccatgg ctgcaggagg gcagcgccag ctcttcttct aaggctccac ccccatctct     120
gcccagcccc agcagactgc cgggcccag cgacacaccc attctgcccc agttccccac      180
catcccctg agcaggctgt tcgacaacgc catgctgagg gctcacaggc tgcaccagct     240
ggcctttgac acctaccagg agttcgagga agcctacatc cccaaggagc agaagtacag     300
cttcctgcag aaccccaga cctccctgtg cttcagcgag agcatcccca cccccagcaa      360
cagagaggag acccagcaga gagcaacct ggagctgctg aggatctccc tgctgctgat      420
ccagagctgg ctggagcccg tgcagttcct gagaagcgtg ttcgccaaca gcctggtgta     480
cggcgccagc gacagcaacg tgtacgacct gctgaaggac ctggaggagg catccagac      540
cctgatgggc cggctggagg acggcagccc caggaccggc cagatcttca agcagaccta     600
cagcaagttc gacaccaaca gccacaacga cgacgccctg ctgaagaact acgggctgct     660
gtactgcttc agaaaggaca tggacaaggt ggagaccttc ctgaggatcg tgcagtgcag     720
aagcgtggag ggcagctgcg gcttcagctc agcagcaag gcccctcccc cgagcctgcc      780
ctccccaagc aggctgcctg ggccctccga cacaccaatc ctgccacaga gcagctcctc     840
taaggcccct cctccatccc tgccatcccc ctcccggctg cctggcccct ctgacacccc     900
tatcctgcct cagtgatgaa ggtctggatg cggccgc                              937
```

<210> SEQ ID NO 46
<211> LENGTH: 889
<212> TYPE: DNA
<213> ORGANISM: Homo sapiens

<400> SEQUENCE: 46

```
tctagaggac atggccaccg gcagcaggac cagcctgctg ctggccttcg gcctgctgtg      60
cctgccatgg ctgcaggagg gcagcgccag ctcttcttct aaggctccac ccccgagcct     120
gcccttcccc accatccccc tgagcaggct gttcgacaac gccatgctga gggctcacag     180
gctgcaccag ctggcctttg acacctacca ggagttcgag gaagcctaca tccccaagga     240
gcagaagtac agcttcctgc agaaccccca gacctccctg tgcttcagcg agagcatccc     300
caccccagc aacagagagg agacccagca gaagagcaac ctggagctgc tgaggatctc     360
cctgctgctg atccagagct ggctggagcc cgtgcagttc ctgagaagcg tgttcgccaa     420
cagcctggtg tacggcgcca gcgacagcaa cgtgtacgac ctgctgaagg acctggagga     480
gggcatccag accctgatgg gccggctgga ggacggcagc cccaggaccg ccagatctt     540
caagcagacc tacagcaagt cgacaccaa cagccacaac gacgacgccc tgctgaagaa     600
ctacgggctg ctgtactgct tcagaaagga catggacaag gtggagacct tcctgaggat     660
cgtgcagtgc agaagcgtgg agggcagctg cggcttcagc tccagcagca aggcccctcc     720
cccgagcctg ccctccccaa gcaggctgcc tgggccctcc gacacaccaa tcctgccaca     780
gagcagctcc tctaaggccc ctcctccatc cctgccatcc cctcccggc tgcctggccc     840
ctctgacacc cctatcctgc ctcagtgatg aaggtctgga tgcggccgc                  889
```

<210> SEQ ID NO 47
<211> LENGTH: 217
<212> TYPE: PRT
<213> ORGANISM: Homo sapiens

<400> SEQUENCE: 47

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 48
<211> LENGTH: 33
<212> TYPE: PRT
<213> ORGANISM: Homo sapiens

<400> SEQUENCE: 48

```
Asp Pro Arg Phe Gln Asp Ser Ser Ser Lys Ala Pro Pro Pro Ser
 1               5                  10                  15

Leu Pro Ser Pro Ser Arg Leu Pro Gly Pro Ser Asp Thr Pro Ile Leu
             20                  25                  30

Gln
```

<210> SEQ ID NO 49
<211> LENGTH: 26
<212> TYPE: PRT
<213> ORGANISM: Homo sapiens

<400> SEQUENCE: 49

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
             20                  25
```

```
<210> SEQ ID NO 50
<211> LENGTH: 17
<212> TYPE: DNA
<213> ORGANISM: Artificial Sequence
<220> FEATURE:
<223> OTHER INFORMATION: Reverse primer for EPO-CTP constructs

<400> SEQUENCE: 50
gcttccgaca gcagggc                                                   17

<210> SEQ ID NO 51
<211> LENGTH: 250
<212> TYPE: PRT
<213> ORGANISM: Artificial
<220> FEATURE:
<223> OTHER INFORMATION: Artificial Sequence

<400> SEQUENCE: 51

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Ala Pro Pro Arg
            20                  25                  30

Leu Ile Cys Asp Ser Arg Val Leu Glu Arg Tyr Leu Leu Glu Ala Lys
        35                  40                  45

Glu Ala Glu Asn Ile Thr Thr Gly Cys Ala Glu His Cys Ser Leu Asn
    50                  55                  60

Glu Asn Ile Thr Val Pro Asp Thr Lys Val Asn Phe Tyr Ala Trp Lys
65                  70                  75                  80

Arg Met Glu Val Gly Gln Gln Ala Val Glu Val Trp Gln Gly Leu Ala
                85                  90                  95

Leu Leu Ser Glu Ala Val Leu Arg Gly Gln Ala Leu Leu Val Asn Ser
            100                 105                 110

Ser Gln Pro Trp Glu Pro Leu Gln Leu His Val Asp Lys Ala Val Ser
        115                 120                 125

Gly Leu Arg Ser Leu Thr Thr Leu Leu Arg Ala Leu Gly Ala Gln Lys
    130                 135                 140

Glu Ala Ile Ser Pro Pro Asp Ala Ala Ser Ala Ala Pro Leu Arg Thr
145                 150                 155                 160

Ile Thr Ala Asp Thr Phe Arg Lys Leu Phe Arg Val Tyr Ser Asn Phe
                165                 170                 175

Leu Arg Gly Lys Leu Lys Leu Tyr Thr Gly Glu Ala Cys Arg Thr Gly
            180                 185                 190

Asp Arg Ser Ser Ser Lys Ala Pro Pro Pro Ser Leu Pro Ser Pro
        195                 200                 205

Ser Arg Leu Pro Gly Pro Ser Asp Thr Pro Ile Leu Pro Gln Ser Ser
    210                 215                 220

Ser Ser Lys Ala Pro Pro Pro Ser Leu Pro Ser Pro Ser Arg Leu Pro
225                 230                 235                 240

Gly Pro Ser Asp Thr Pro Ile Leu Pro Gln
                245                 250
```

LONG-ACTING POLYPEPTIDES AND METHODS OF PRODUCING AND ADMINISTERING SAME

CROSS REFERENCE TO RELATED APPLICATIONS

This application is a continuation of U.S. patent application Ser. No. 14/309,496, filed Jun. 19, 2014, which is (1) a continuation in part of U.S. patent application Ser. No. 14/059,134, filed Oct. 21, 2013, which is a continuation in part of U.S. patent application Ser. No. 13/804,354, filed Mar. 14, 2013 and issued Feb. 3, 2015 as U.S. Pat. No. 8,946,155, which is a continuation in part of U.S. patent application Ser. No. 13/192,542 filed Jul. 28, 2011 and issued Jun. 18, 2013 as U.S. Pat. No. 8,465,948, which is a continuation of U.S. patent application Ser. No. 12/401,755 filed Mar. 11, 2009 and issued Feb. 14, 2013 as U.S. Pat. No. 8,114,836, which is a continuation of U.S. application Ser. No. 11/702,156 filed on Feb. 05, 2007, now abandoned, which claims the benefit of U.S. Provisional Application Ser. No. 60/764,761, filed Feb. 3, 2006, and (2) a continuation-in-part of U.S. patent application Ser. No. 13/195,931, filed Aug. 2, 2011 and issued May 28, 2013 as U.S. Pat. No. 8,450,269, which is a continuation-in-part of U.S. patent application Ser. No. 12/509,188, filed Jul. 24, 2009 and issued Nov. 6, 2012 as U.S. Pat. No. 8,304,386, which is a continuation-in-part of U.S. patent application Ser. No. 12/476,916, filed Jun. 2, 2009 and issued Nov. 1, 2011 as U.S. Pat. No. 8,048,849, which is a continuation-in-part of U.S. patent application Ser. No. 12/401,746, filed Mar. 11, 2009 and issued Jan. 17, 2012 as U.S. Pat. No. 8,097,435, and is a continuation of U.S. patent application Ser. No. 11/700,910, filed Feb. 1, 2007 and issued Jun. 30, 2009 as U.S. Pat. No. 7,553,940, which claims the benefit of U.S. Provisional Application Ser. No. 60/764,761, filed Feb. 3, 2006. All of these applications are hereby incorporated by reference in their entirety herein.

FIELD OF INVENTION

A polypeptide and polynucleotides encoding same comprising at least two carboxy-terminal peptides (CTP) of chorionic gonadotrophin attached to a peptide-of-interest are disclosed. Pharmaceutical compositions comprising the polypeptide and polynucleotides of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administered by infusion, frequent injection of peptide drugs causes considerable discomfort to a subject. Thus, there is a need for technologies that will prolong the half-lives of therapeutic polypeptides while maintaining a high pharmacological efficacy thereof. Such desired peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

SUMMARY OF THE INVENTION

In one embodiment, the invention relates to a method of reducing the dosing frequency of a growth hormone in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the invention relates to a method of improving the area under the curve (AUC) of a growth hormone in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In one embodiment, the invention relates to a method of treating a subject in need of GH therapy, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the invention relates to a method of increasing insulin-like growth factor (IGF-1) levels in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby increasing insulin-like growth factor (IGF-1) levels in a subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIGS. 1A-1F are diagrams illustrating six EPO-CTP constructs.

FIG. 1A—is a diagram of the polypeptide of SEQ ID NO: 1.

FIG. 1B is a diagram of the polypeptide of SEQ ID NO: 2.

FIG. 1C is a diagram of the polypeptide of SEQ ID NO: 3.

FIG. 1D is a diagram of the polypeptide of SEQ ID NO: 4.

FIG. 1E is a diagram of the polypeptide of SEQ ID NO: 5.

FIG. 1F is a diagram of the polypeptide of SEQ ID NO: 6.

FIG. 2 is a photograph illustrating the expression of the EPO-CTP variants from transfected DG44 cells. Final test samples from transfected cells were prepared as described under "sample preparation" and run on SDS/PAGE. Proteins were detected by Western blot.

DETAILED DESCRIPTION OF THE INVENTION

Figure 3:
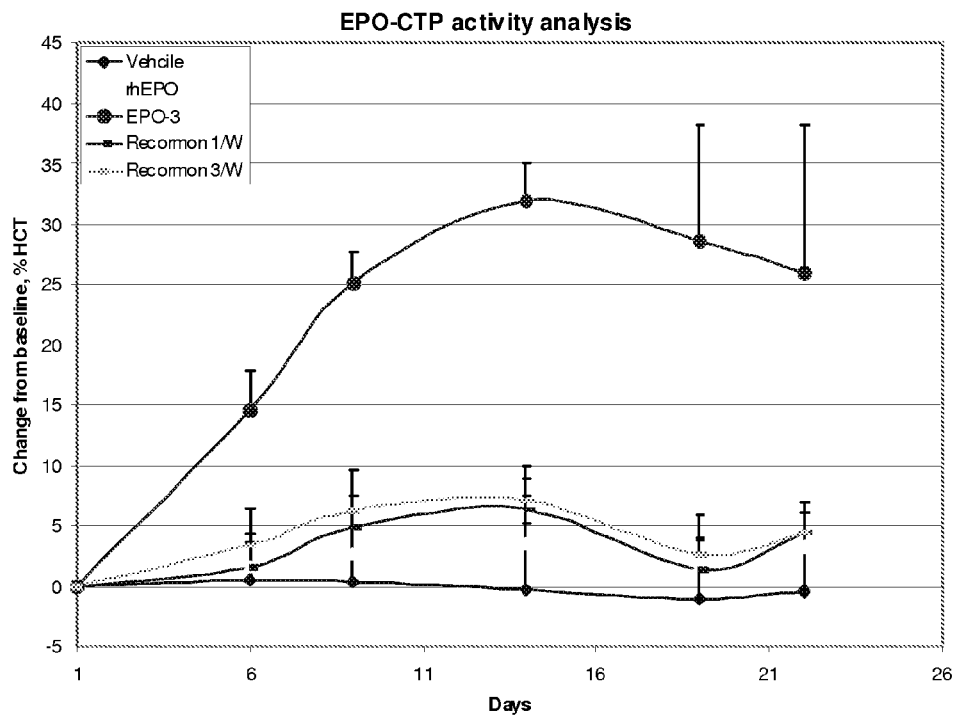
FIG. 3 is a graph illustrating the in vivo bioactivity of recombinant hEPO derivatives and EPO-3 (SEQ ID NO: 3). ICR mice (n=7/group) received a single i.v. injection/week (15 µg/kg) for three weeks of EPO-3, rhEPO-WT (SEQ ID NO: 16), Recormon® (Commercial EPO) or Recormon® (5 µg/kg) 3 times a week. Control animals were injected i.v. with PBS. Blood samples were collected three times a week and haematocrit levels were detected. Each point represents the group average of haematocrit (%) ±SE.

In one embodiment, the present invention describes long-acting polypeptides and methods of producing and using same. In another embodiment, long-acting polypeptides comprise carboxy terminal peptide (CTP) of human Chorionic Gonadotropin (hCG). In another embodiment, CTP acts as a protectant against degradation of proteins or peptides derived therefrom. In another embodiment, CTP extends circulatory half-lives of proteins or peptides derived therefrom. In some embodiments, CTP enhances the potency of proteins or peptides derived therefrom.

In another embodiment, "CTP peptide," "carboxy terminal peptide," and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, "peptide of interest" and "polypeptide sequence of interest" are used interchangeably herein. In another embodiment, the peptide of interest is a full-length protein. In another embodiment, the peptide of interest is a protein fragment. Each possibility represents a separate embodiment of the present invention.

In another embodiment, the invention provides a polypeptide consisting a growth hormone, a single chorionic gonadotrophin carboxy terminal peptide attached to the amino terminus of the growth hormone, and two chorionic gonadotrophin carboxy terminal peptides attached to the carboxy terminus of the growth hormone. In another embodiment, the invention provides a polypeptide consisting a growth hormone, a single chorionic gonadotrophin carboxy terminal peptide attached to the amino terminus of the growth hormone, two chorionic gonadotrophin carboxy terminal peptides attached to the carboxy terminus of the growth hormone, and a signal peptide attached to the amino terminus of one chorionic gonadotrophin carboxy terminal peptide.

In another embodiment, a growth hormone comprising CTPs as described herein has enhanced in vivo biological activity compared the same growth hormone without CTPs. In another embodiment, a growth hormone comprising at least one CTP attached to its amino terminus and at least two CTPs attached to its carboxy terminus has enhanced in vivo biological activity compared the same growth hormone without CTPs. In another embodiment, a growth hormone comprising one CTP attached to its amino terminus and two CTPs attached to its carboxy terminus has enhanced in vivo biological activity compared the same growth hormone without CTPs.

In another embodiment, a polypeptide comprising at least two carboxy-terminal peptide (CTP) sequences of chorionic gonadotrophin attached to a polypeptide sequence of interest, wherein a first CTP sequence of the at least two CTP sequences is attached to an amino terminus of the polypeptide sequence of interest and a second CTP sequence of the at least two CTP sequences is attached to the carboxy terminus of the polypeptide sequence of interest is provided. In another embodiment, the carboxy-terminal peptide (CTP) sequence is of human chorionic gonadotrophin.

In another embodiment, a subject is a human subject. In another embodiment, a subject is a pet. In another embodiment, a subject is a mammal. In another embodiment, a subject is a farm animal. In another embodiment, a subject is a dog. In another embodiment, a subject is a cat. In another embodiment, a subject is a monkey. In another embodiment, a subject is a horse. In another embodiment, a subject is a cow. In another embodiment, a subject is a mouse. In another embodiment, a subject is a rat. In one embodiment, the subject is male. In another embodiment, the subject is female.

The phrase "polypeptide sequence of interest" refers, in another embodiment, to any polypeptide sequence, such as one comprising a biological activity. In another embodiment, the peptide is glycosylated. In another embodiment, the peptide is non-glycosylated. Examples of polypeptides which benefit from an extension in their circulatory half-life include, but are not limited to erythropoietin (EPO), interferons, human growth hormone (hGH) and glucagon-like peptide-1 (GLP-1).

In another embodiment, the configuration of CTP-growth hormone-CTP-CTP as described herein comprises a growth hormone or an active fragment thereof connected via a peptide bond to at least one CTP unit. In another embodiment, a CTP-growth hormone-CTP-CTP as described herein comprises a growth hormone or an active fragment thereof connected via a peptide bond to at least one CTP unit which is connected to an additional CTP unit via a peptide bond. In another embodiment, a polypeptide as described herein comprising a growth hormone fragments thereof and CTP units and/or fragments thereof are interconnected via a peptide bond. In another embodiment, one nucleic acid molecule encodes a polypeptide as described herein comprising a growth hormone and/or fragments thereof and CTP units and/or fragments thereof.

In another embodiment, the carboxy-terminal peptide (CTP) is attached to the polypeptide sequence of interest via a linker. In another embodiment, at least one CTP is optionally attached to said polypeptide sequence of interest via a linker. In another embodiment, the linker which connects the CTP sequence to the polypeptide sequence of interest is a covalent bond. In another embodiment, the linker which connects the CTP sequence to the polypeptide sequence of interest is a peptide bond. In another embodiment, the linker which connects the CTP sequence to the polypeptide sequence of interest is a substituted peptide bond. In another embodiment, the carboxy-terminal peptide (CTP) sequence comprises an amino acid sequence selected from the sequences set forth in SEQ ID NO: 48.

In another embodiment, SEQ ID NO: 48 comprises the following amino acid (AA) sequence: DPRFQDSSSSKAP-PPSLPSPSRLPGPSDTPILQ (SEQ ID NO: 48).

In another embodiment, the carboxy terminal peptide (CTP) of human Chorionic Gonadotropin (hCG) is fused to a protein. In another embodiment, the carboxy terminal peptide (CTP) of human hCG is fused to a glycoprotein. In another embodiment, the carboxy terminal peptide (CTP) of hCG is fused to a glycoprotein hormone. In another embodiment, the CTP of hCG is fused to a peptide derived from a glycoprotein hormone. In some embodiments, glycoprotein hormones comprise EPO, FSH, or TSH and peptides derived therefrom.

In some embodiments, a CTP sequence at both the amino terminal end of a polypeptide and at the carboxy terminal end of the polypeptide provide enhanced protection against degradation of a protein. In some embodiments, CTP sequences at both the amino terminal end of a polypeptide and at the carboxy terminal end of the polypeptide provide an extended half-life to the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced protection against degradation of a protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced activity of the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced protection against degradation of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced activity the attached protein.

In some embodiments, a CTP sequences at both the amino terminal end of a growth hormone and at the carboxy terminal end of the growth hormone provide enhanced protection against degradation of a growth hormone. In another embodiment, at least one CTP sequence at the amino terminal end of a growth hormone and two CTP units in the carboxy terminal end of a growth hormone provide enhanced protection against clearance. In another embodiment, at least one CTP sequence at the amino terminal end of a growth hormone and two CTP units in the carboxy terminal end of a growth hormone provide prolonged clearance time. In another embodiment, at least one CTP sequence at the amino terminal end of a growth hormone and two CTP units in the carboxy terminal end of a growth hormone enhance $C_{max}$ of a growth hormone. In another embodiment, at least one CTP sequence at the amino terminal end of a growth hormone and two CTP units in the carboxy terminal end of a growth hormone enhance $T_{max}$ of a growth hormone. In another embodiment, at least one CTP sequence at the amino terminal end of a growth hormone and two CTP units in the carboxy terminal end of a growth hormone enhanced T1/2.

In some embodiments, CTP sequences at both the amino terminal end of a growth hormone and at the carboxy terminal end of the growth hormone extend the half-life of the modified growth hormone. In another embodiment, at least a single CTP sequence at the amino terminal end of a growth hormone and at least two CTP sequences at the carboxy terminal end of the growth hormone provide an extended half-life to the modified growth hormone. In another embodiment, a single CTP sequence at the amino terminal end of a growth hormone and two CTP sequences at the carboxy terminal end of the growth hormone provide extended half-life to the attached growth hormone. In another embodiment, a single CTP sequence at the amino terminal end of a growth hormone and two CTP sequences in tandem at the carboxy terminal end of the growth hormone provide extended half-life to the modified growth hormone.

In some embodiments, a CTP sequence at the amino terminal end of a polypeptide, a CTP sequence at the carboxy terminal end of the growth hormone, and at least one additional CTP sequence attached in tandem to the CTP sequence at the carboxy terminus provide enhanced protection against degradation to a growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus extend the half-life of the growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus enhance the biological activity of the growth hormone.

In another embodiment, the carboxy terminal peptide (CTP) peptide of the present invention comprises the amino acid sequence from amino acid 112 to position 145 of human chorionic gonadotrophin, as set forth in SEQ ID NO: 17. In another embodiment, the CTP sequence of the present invention comprises the amino acid sequence from amino acid 118 to position 145 of human chorionic gonadotropin, as set forth in SEQ ID NO: 18. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native CTP DNA sequence or a peptide thereof. In another embodiment, the CTP peptide DNA sequence of the present invention is at least 80% homologous to the native CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 43. In one embodiment, the truncated CTP comprises the first 11 amino acids of SEQ ID NO: 43. In one embodiment, the truncated CTP comprises the first 12 amino acids of SEQ ID NO: 43. In one embodiment, the truncated CTP comprises the first 13 amino acids of SEQ ID NO: 43. In one embodiment, the truncated CTP comprises the first 14 amino acids of SEQ ID NO: 43. In one embodiment, the truncated CTP comprises the first 15 amino acids of SEQ ID NO: 43. In one embodiment, the truncated CTP comprises the first 16 amino acids of SEQ ID NO: 43. In one embodiment, the truncated CTP comprises the last 14 amino acids of SEQ ID NO: 43.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites. Each possibility represents a separate embodiment of the present invention.

As provided herein, attachment of CTP sequence to both the amino and carboxy termini of the EPO protein results in increased potency at stimulating erythropoiesis (FIGS. 3-5 and Table 6 of Example 4), as compared to recombinant EPO and other combinations of EPO and CTP. In some embodiments, an EPO attached to three CTP sequences does not impair binding to its receptor as evidenced in Table 4 of Example 3, which demonstrates that EPO attached to three CTP sequences is equally effective at stimulating proliferation of TF-1 cells as wild-type EPO.

In some embodiments, "homology" according to the present invention also encompasses deletions, insertions, or substitution variants, including an amino acid substitution thereof, and biologically active polypeptide fragments thereof. In one embodiment the substitution variant comprises a substitution of the glycine in position 104 of the erythropoietin amino acid sequence with a serine (SEQ ID NO: 22).

In another embodiment, the methods of the present invention provide an EPO peptide having additionally at least one CTP amino acid peptide on the N-terminus and at least one CTP amino acid peptide on the C-terminus for the treatment of anemia. In another embodiment, the methods of the present invention provide an EPO peptide having additionally one CTP amino acid peptide on the N-terminus and two CTP amino acid peptides on the C-terminus for the treatment of anemia. In another embodiment, the methods of the present invention provide an EPO peptide set forth in SEQ ID NO: 1 having additionally at least one CTP amino acid peptide on the N-terminus for the treatment of anemia. In another embodiment, the methods of the present invention provide an EPO peptide set forth in SEQ ID NO: 1 having additionally at least one CTP amino acid peptide on the N-terminus and at least one additional CTP amino acid peptide on the C-terminus for the treatment of anemia. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of anemia.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of anemia. In another embodiment, the methods of the present invention provide a nucleic acid sequence encoding an EPO peptide having additionally one CTP amino acid peptide on the N-terminus and two CTP amino acid peptides on the C-terminus for the treatment of anemia. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for the treatment of anemia. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for the treatment of anemia.

In another embodiment, the methods of the present invention provide any of the CTP-modified EPO peptides described herein, for inhibiting anemia.

In another embodiment, the methods of the present invention provide a nucleic acid sequence encoding any of the CTP-modified EPO peptides described herein, for inhibiting anemia.

In another embodiment, the methods of the present invention provide any of the CTP-modified EPO peptides described herein, for the treatment of tumor-associated anemia.

In another embodiment, the methods of the present invention provide a nucleic acid sequence encoding any of the CTP-modified EPO peptides described herein, for the treatment of tumor-associated anemia.

In another embodiment, the methods of the present invention provide any of the CTP-modified EPO peptides described herein, for inhibiting tumor-associated anemia.

In another embodiment, the methods of the present invention provide a nucleic acid sequence encoding any of the CTP-modified EPO peptides described herein, for inhibiting tumor-associated anemia.

In another embodiment, the methods of the present invention provide any of the CTP-modified EPO peptides, as described herein, for the treatment of tumor hypoxia.

In another embodiment, the methods of the present invention provide a nucleic acid sequence encoding any of the CTP-modified EPO peptides described herein, for the treatment of tumor hypoxia.

In another embodiment, the methods of the present invention provide any of the CTP-modified EPO peptides described herein, for the treatment of chronic infections such as HIV, inflammatory bowel disease, or septic episodes.

In another embodiment, the methods of the present invention provide a nucleic acid sequence encoding any of the CTP-modified EPO peptides for the treatment of chronic infections such as HIV, inflammatory bowel disease, or septic episodes.

In another embodiment, the methods of the present invention provide any of the CTP-modified EPO peptides described herein, for inhibiting chronic infections such as HIV, inflammatory bowel disease, or septic episodes.

In another embodiment, the methods of the present invention provide a nucleic acid sequence encoding any of the CT-modified EPO peptides described herein, for inhibiting chronic infections such as HIV, inflammatory bowel disease, or septic episodes.

In another embodiment, the methods of the present invention provide any of the CTP-modified EPO peptides described herein, for the treatment of fatigue syndrome following cancer chemotherapy.

In another embodiment, the methods of the present invention provide a nucleic acid sequence encoding any of the CTP-modified EPO peptides described herein, for the treatment of fatigue syndrome following cancer chemotherapy.

In another embodiment, the methods of the present invention provide any of the CTP-modified EPO peptides described herein, for improving stem cell engraftment.

In another embodiment, the methods of the present invention provide a nucleic acid sequence encoding any of the CTP-modified EPO peptides described herein, for improving stem cell engraftment.

In another embodiment, the methods of the present invention provide any of the CTP-modifieds EPO peptide described herein, for increasing the survival rate of a patient with aplastic anemia or myelodysplastic syndrome.

In another embodiment, the methods of the present invention provide a nucleic acid sequence encoding any of the CTP-modified EPO peptides described herein, for increasing the survival rate of a patient with aplastic anemia or myelodysplastic syndrome.

Figure 11:
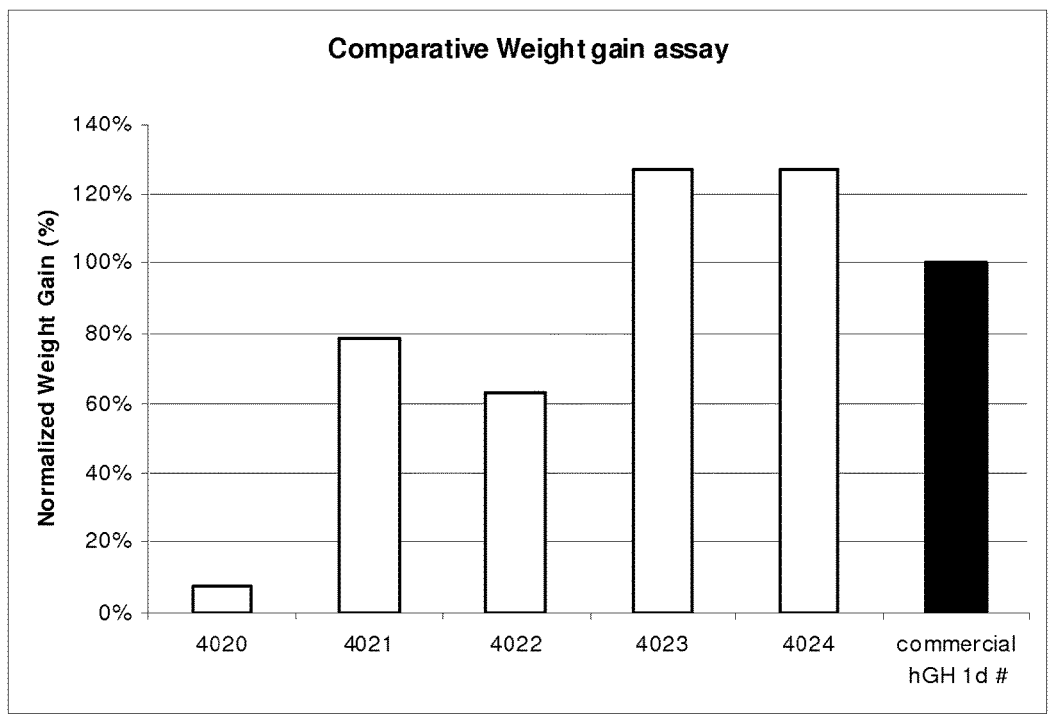
FIG. 11 is a bar graph illustrating the weight gain of hypophysectomized rats following administration of the GH-CTP polypeptides of the present invention.

In some embodiments, human growth hormone (hGH) is utilized according to the teachings of the present invention. In some embodiments, the attachment of CTP sequence to both the amino and carboxy termini of the hGH protein results in increased potency (FIG. 11). In some embodiments, the attachment of CTP sequence to both the amino and carboxy termini of the hGH protein results in prolonged in-vivo activity. In one embodiment, CTP-hGH polypeptides of the present invention are set forth in SEQ ID NO: 39-41.

As provided herein, growth gain was demonstrated in hypophysectomized rats (which have no growth hormone secretion) following injections of CTP-hGH.

In one embodiment, the phrase "human growth hormone" (hGH) refers to a polypeptide, such as set forth in Genbank Accession No. P01241 (SEQ ID NO: 47), exhibiting hGH activity (i.e. stimulation of growth).

In another embodiment, "human growth hormone" (hGH) refers to a polypeptide, such as set forth in Genbank Accession No. P01241, exhibiting hGH activity (i.e. stimulation of growth). In another embodiment, "GH" of the present invention also refers to homologues. In another embodiment, a GH amino acid sequence of the methods and compositions the present invention is at least 50% homologous to a GH sequence set forth herein as determined using BlastP software of the National Center of Biotechnology Information (NCBI) using default parameters. In another embodiment, the percent homology is 60%. In another embodiment, the percent homology is 70%. In another embodiment, the percent homology is 80%. In another embodiment, the percent homology is 90%. In another embodiment, the percent homology is at least 95%. In another embodiment, the percent homology is greater than 95%. Each possibility represents a separate embodiment of the present invention.

Exemplary CTP-GH polypeptides and CTP-hGH polypeptides of the present invention are set forth in SEQ ID NO: 39, SEQ ID NO: 40 and SEQ ID NO: 41.

In another embodiment, the methods of the present invention provide a growth hormone (GH) peptide having additionally at least one CTP amino acid peptide on the N-terminus and at least one CTP amino acid peptide on the C-terminus for stimulating muscle growth. In another embodiment, the methods of the present invention provide a GH peptide having additionally one CTP amino acid peptide on the N-terminus and two CTP amino acid peptides on the C-terminus for stimulating muscle growth. In another embodiment, the methods of the present invention provide a GH peptide set forth in SEQ ID NO: 23 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 36 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 37 having additionally at least one CTP amino acid peptide on the N-terminus for stimulating muscle growth. In another embodiment, the methods of the present invention provide a GH peptide set forth in SEQ ID NO: 38, having additionally at least one CTP amino acid peptide on the N-terminus for stimulating muscle growth. In another embodiment, the methods of the present invention provide a GH peptide set forth in SEQ ID NO: 39 for stimulating muscle growth. In another embodiment, the methods of the present invention provide a GH peptide set forth in SEQ ID NO: 40 for stimulating muscle growth. In another embodiment, the methods of the present invention provide a GH peptide set forth in SEQ ID NO: 41 for stimulating muscle growth. In another embodiment, the methods of the present invention provide a GH peptide set forth in SEQ ID NO: 42 having additionally at least one CTP amino acid peptide on the N-terminus for stimulating muscle growth. In another embodiment, the methods of the present invention provide a GH peptide modified by CTPs as provided herein for stimulating muscle growth.

In another embodiment, the methods of the present invention provide a nucleic acid sequence encoding a GH peptide having additionally at least one CTP amino acid peptide on the N-terminus and at least one CTP amino acid peptide on the C-terminus for stimulating muscle growth. In another embodiment, the methods of the present invention provide a nucleic acid sequence encoding a GH peptide having additionally one CTP amino acid peptide on the N-terminus and two CTP amino acid peptides on the C-terminus for stimulating muscle growth. In another embodiment, the methods of the present invention provide a nucleic acid of SEQ ID NO: 45 encoding a GH peptide comprising one CTP amino acid peptide on the N-terminus and two CTP amino acid peptides on the C-terminus for stimulating muscle growth. In another embodiment, the methods of the present invention provide a nucleic acid of SEQ ID NO: 46 encoding a GH peptide and one CTP amino acid peptide on the N-terminus and two CTP amino acid peptides on the C-terminus for stimulating muscle growth.

In one embodiment, the present invention provides a method of reducing the dosing frequency of a growth hormone in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the present invention provides a method of improving the area under the curve (AUC) of a growth hormone in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In one embodiment, the present invention provides a method of treating a subject in need of GH therapy, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the present invention provides a method of increasing insulin-like growth factor (IGF-1) levels in a subject, comprising administering to said subject a therapeutically effective amount of a polypeptide consisting of a growth hormone, one chorionic gonadotrophin carboxy terminal peptide (CTP) attached to the amino terminus of said growth hormone, and two chorionic gonadotrophin CTPs attached to the carboxy terminus of said growth hormone, and wherein said polypeptide optionally consists of a signal peptide attached to the amino terminus of said one CTP, thereby increasing insulin-like growth factor (IGF-1) levels in a subject.

In another embodiment, the methods of the present invention provide any of the CTP-modified GH peptides described herein, for stimulating bone growth.

In another embodiment, the methods of the present invention provide a nucleic acid sequence encoding any of the CTP-modified GH peptides described herein, for stimulating bone growth.

In another embodiment, conjugated growth hormones of this invention are used in the same manner as unmodified growth hormones. In another embodiment, conjugated growth hormones of this invention have an increased circulating half-life and plasma residence time, decreased clearance, and increased clinical activity in vivo. In another embodiment, due to the improved properties of the conjugated growth hormones as described herein, these conjugates are administered less frequently than unmodified growth hormones. In another embodiment, conjugated growth hormones as described herein are administered once a week to once every two weeks. In another embodiment, conjugated growth hormones as described herein are administered once every two weeks to once every three weeks. In another embodiment, conjugated growth hormones as described herein are administered once a day to three times a week. In another embodiment, decreased frequency of administration will result in improved patient compliance leading to improved treatment outcomes, as well as improved patient quality of life. In another embodiment, compared to conventional conjugates of growth hormones linked to poly(ethylene glycol) it has been found that growth hormone CTP conjugates having the molecular weight and linker structure of the conjugates of this invention have an improved potency, improved stability, elevated AUC levels, enhanced circulating half-life. In another embodiment, compared to conventional conjugates of growth hormones linked to poly(ethylene glycol) it has been found that growth hormones having the molecular weight and linker structure of the conjugates of this invention have an improved potency, improved stability, elevated AUC levels, enhanced circulating half-life. In another embodiment, a therapeutically effective amount of a conjugated growth hormone is the amount of conjugate necessary for the in vivo measurable expected biological activity. In another embodiment, a growth hormone utilized according to the teachings of the present invention exhibits increased potency. In some embodiments, the attachment of CTP sequence to both the amino and carboxy termini of a growth hormone results in prolonged in-vivo activity.

In another embodiment, a therapeutically effective amount of a conjugated growth hormone is determined according to factors as the exact type of condition being treated, the condition of the patient being treated, as well as the other ingredients in the composition. In another embodiment, a therapeutically effective amount of a conjugated growth hormone is 0.01 to 10 µg per kg body weight administered once a week. In another embodiment, a therapeutically effective amount of a conjugated growth hormone is 0.1 to 1 µg per kg body weight, administered once a week. In another embodiment, a pharmaceutical composition comprising a conjugated growth hormone is formulated at strength effective for administration by various means to a human patient.

In another embodiment, the growth hormone is any growth hormone known to one of skill in the art. In another embodiment, the growth hormone is a human growth hormone. In another embodiment, the growth hormone is a non-human growth hormone. In another embodiment, the nucleotide sequence and/or the amino acid sequence of a growth hormone is available in a gene bank database. In another embodiment, the growth hormone is a homologue. In another embodiment, a homologue also refers to a deletion, insertion, or substitution variant, including an amino acid substitution, thereof and biologically active polypeptide fragments thereof.

In another embodiment, the growth hormone is variant of hGH missing exons 2, 3, 4, or any combination thereof. In another embodiment, the growth hormone comprises a signal peptide. In another embodiment, the growth hormone comprises a signal cleavage site. In another embodiment, polypeptides comprising GH modified by CTPs of the present invention comprise recombinant GH.

In another embodiment, the methods of the present invention provide a GH peptide of the present invention for maintaining muscle quality.

In another embodiment, the methods of the present invention provide a GH of the present invention for maintaining bone quality.

In another embodiment, the methods of the present invention provide a GH-CTP nucleic acid sequence of the present invention for maintaining bone quality.

In another embodiment, the methods of the present invention provide any of the CTP-modified GH peptides described herein, for treating a wasting disease.

In another embodiment, the methods of the present invention provide a nucleic acid sequence encoding any of the CTP-modified GH peptides described herein, for treating a wasting disease.

In another embodiment, the methods of the present invention provide any of the CTP-modified GH peptides described herein, for increasing cardiac function.

In another embodiment, the methods of the present invention provide a nucleic acid sequence encoding any of the CTP-modified GH peptides described herein, for increasing cardiac function.

In another embodiment, the methods of the present invention provide a GH peptides described herein, for increasing lipolysis.

In another embodiment, the methods of the present invention provide a nucleic acid sequence encoding any of the CTP-modified GH peptides described herein, for increasing lipolysis.

In another embodiment, the methods of the present invention provide any of the CTP-modified GH peptides described herein, for improving fluid balance.

In another embodiment, a growth hormone of the invention comprises the gene bank amino acid deposited sequence under accession no. AAA72260. In another embodiment, a growth hormone of the invention comprises the gene bank amino acid deposited sequence under accession no. AAK69708. In another embodiment, a growth hormone of the invention comprises the gene bank amino acid deposited sequence under accession no. CAA01435. In another embodiment, a growth hormone of the invention comprises the gene bank amino acid deposited sequence under accession no. CAA01329. In another embodiment, a growth hormone of the invention comprises the gene bank amino acid deposited sequence under accession no. CAA00380. In another embodiment, a growth hormone of the invention comprises the gene bank amino acid deposited sequence under accession no. AAA72555. In another embodiment, a growth hormone of the invention comprises the gene bank amino acid deposited sequence under accession no. NP_000506.2. In another embodiment, a growth hormone of the invention comprises the gene bank amino acid deposited sequence under accession no. NP_072053.1. In another embodiment, a growth hormone of the invention comprises the gene bank amino acid deposited sequence under accession no. NP_072054.1. In another embodiment, a growth hormone of the invention comprises the gene bank amino acid deposited sequence under accession no. NP_072055.1. In another embodiment, a growth hormone of the invention comprises the gene bank amino acid deposited sequence under accession no. NP_072056.1.

In another embodiment, the methods of the present invention provide a nucleic acid sequence encoding a GH peptide having additionally at least one CTP amino acid peptide on the N-terminus and at least one CTP amino acid peptide on the C-terminus for improving fluid balance. In another embodiment, the methods of the present invention provide a nucleic acid sequence encoding a GH peptide having additionally one CTP amino acid peptide on the N-terminus and two CTP amino acid peptides on the C-terminus for improving fluid balance. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving fluid balance. In another embodiment, the methods of the present invention provide a nucleic acid of SEQ ID NO: 46 encoding a GH peptide and one CTP amino acid peptide on the N-terminus and two CTP amino acid peptides on the C-terminus for improving fluid balance.

In another embodiment, the methods of the present invention provide a GH peptide having additionally at least one CTP amino acid peptide on the N-terminus and at least one CTP amino acid peptide on the C-terminus for treating osteoporosis. In another embodiment, the methods of the present invention provide a GH peptide having additionally one CTP amino acid peptide on the N-terminus and two CTP amino acid peptides on the C-terminus for treating osteoporosis. In another embodiment, the methods of the present invention provide a GH peptide set forth in SEQ ID NO: 23 having additionally at least one CTP amino acid peptide on the N-terminus and at least one CTP amino acid peptide on the C-terminus for treating osteoporosis. In another embodiment, the methods of the present invention provide a GH peptide set forth in SEQ ID NO: 36 having additionally at least one CTP amino acid peptide on the N-terminus and at least one CTP amino acid peptide on the C-terminus for treating osteoporosis. In another embodiment, the methods of the present invention provide a GH peptide set forth in SEQ ID NO: 37 having additionally at least one CTP amino acid peptide on the N-terminus for treating osteoporosis. In another embodiment, the methods of the present invention provide a GH peptide set forth in SEQ ID NO: 38 having additionally at least one CTP amino acid peptide on the N-terminus for treating osteoporosis. In another embodiment, the methods of the present invention provide a GH peptide set forth in SEQ ID NO: 39 for treating osteoporosis. In another embodiment, the methods of the present invention provide a GH peptide set forth in SEQ ID NO: 40 for treating osteoporosis. In another embodiment, the methods of the present invention provide a GH peptide set forth in SEQ ID NO: 41 for treating osteoporosis. In another embodiment, the methods of the present invention provide a GH peptide set forth in SEQ ID NO: 42 having additionally at least one CTP amino acid peptide on the N-terminus for treating osteoporosis. In another embodiment, the methods of the present invention provide a GH peptide modified by CTPs, as provided herein, for treating osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for treating osteoporosis. In another embodiment, the methods of the present invention provide a nucleic acid sequence encoding a GH peptide having additionally one CTP amino acid peptide on the N-terminus and two CTP amino acid peptides on the C-terminus for treating osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for treating osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for treating osteoporosis.

In another embodiment, the methods of the present invention provide a GH peptide having additionally at least one CTP amino acid peptide on the N-terminus and at least one CTP amino acid peptide on the C-terminus for inhibiting osteoporosis. In another embodiment, the methods of the present invention provide a GH peptide having additionally one CTP amino acid peptide on the N-terminus and two CTP amino acid peptides on the C-terminus for inhibiting osteoporosis. In another embodiment, the methods of the present invention provide a GH peptide set forth in SEQ ID NO: 23 having additionally at least one CTP amino acid peptide on the N-terminus and at least one CTP amino acid peptide on the C-terminus for inhibiting osteoporosis. In another embodiment, the methods of the present invention provide a GH peptide set forth in SEQ ID NO: 36 having additionally at least one CTP amino acid peptide on the N-terminus and at least one CTP amino acid peptide on the C-terminus for inhibiting osteoporosis. In another embodiment, the methods of the present invention provide a GH peptide set forth in SEQ ID NO: 37 having additionally at least one CTP amino acid peptide on the N-terminus for inhibiting osteoporosis. In another embodiment, the methods of the present invention provide a GH peptide set forth in SEQ ID NO: 38 having additionally at least one CTP amino acid peptide on the N-terminus for inhibiting osteoporosis. In another embodiment, the methods of the present invention provide a GH peptide set forth in SEQ ID NO: 39 for inhibiting osteoporosis. In another embodiment, the methods of the present invention provide a GH peptide set forth in SEQ ID NO: 40 for inhibiting osteoporosis. In another embodiment, the methods of the present invention provide a GH peptide set forth in SEQ ID NO: 41 for inhibiting osteoporosis. In another embodiment, the methods of the present invention provide a GH peptide set forth in SEQ ID NO: 42 having additionally at least one CTP amino acid peptide on the N-terminus for inhibiting osteoporosis. In another embodiment, the methods of the present invention provide a GH peptide modified by CTPs, as provided herein, for inhibiting osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for inhibiting osteoporosis. In another embodiment, the methods of the present invention provide a nucleic acid sequence encoding a GH peptide having additionally one CTP amino acid peptide on the N-terminus and two CTP amino acid peptides on the C-terminus for inhibiting osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for inhibiting osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for inhibiting osteoporosis.

In another embodiment, the methods of the present invention provide a GH peptide of the present invention for improving exercise capacity.

In another embodiment, the methods of the present invention provide a GH peptide having additionally at least one CTP amino acid peptide on the N-terminus and at least one CTP amino acid peptide on the C-terminus for improving lung function. In another embodiment, the methods of the present invention provide a GH peptide having additionally one CTP amino acid peptide on the N-terminus and two CTP amino acid peptides on the C-terminus for improving lung function. In another embodiment, the methods of the present invention provide a GH peptide set forth in SEQ ID NO: 23 having additionally at least one CTP amino acid peptide on the N-terminus and at least one CTP amino acid peptide on the C-terminus for improving lung function. In another embodiment, the methods of the present invention provide a GH peptide set forth in SEQ ID NO: 36 having additionally at least one CTP amino acid peptide on the N-terminus and at least one CTP amino acid peptide on the C-terminus for improving lung function. In another embodiment, the methods of the present invention provide a GH peptide set forth in SEQ ID NO: 37 having additionally at least one CTP amino acid peptide on the N-terminus for improving lung function. In another embodiment, the methods of the present invention provide a GH peptide set forth in SEQ ID NO: 38 having additionally at least one CTP amino acid peptide on the N-terminus for improving lung function. In another embodiment, the methods of the present invention provide a GH peptide set forth in SEQ ID NO: 39 for improving lung function. In another embodiment, the methods of the present invention provide a GH peptide set forth in SEQ ID NO: 40 for improving lung function. In another embodiment, the methods of the present invention provide a GH peptide set forth in SEQ ID NO: 41 for improving lung function. In another embodiment, the methods of the present invention provide a GH peptide set forth in SEQ ID NO: 42 having additionally at least one CTP amino acid peptide on the N-terminus for improving lung function. In another embodiment, the methods of the present invention provide a GH peptide modified by CTPs as provided herein for improving lung function.

In another embodiment, the methods of the present invention provide a nucleic acid sequence encoding a GH peptide having additionally at least one CTP amino acid peptide on the N-terminus and at least one CTP amino acid peptide on the C-terminus for improving lung function. In another embodiment, the methods of the present invention provide a nucleic acid sequence encoding a GH peptide having additionally one CTP amino acid peptide on the N-terminus and two CTP amino acid peptides on the C-terminus for improving lung function. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving lung function. In another embodiment, the methods of the present invention provide a nucleic acid of SEQ ID NO: 46 encoding a GH peptide and one CTP amino acid peptide on the N-terminus and two CTP amino acid peptides on the C-terminus for improving lung function.

In another embodiment, the methods of the present invention provide a GH peptide having additionally at least one CTP amino acid peptide on the N-terminus and at least one CTP amino acid peptide on the C-terminus for improving immunity. In another embodiment, the methods of the present invention provide a GH peptide having additionally one CTP amino acid peptide on the N-terminus and two CTP amino acid peptides on the C-terminus for improving immunity. In another embodiment, the methods of the present invention provide a GH peptide set forth in SEQ ID NO: 23 having additionally at least one CTP amino acid peptide on the N-terminus and at least one CTP amino acid peptide on the C-terminus for improving immunity. In another embodiment, the methods of the present invention provide a GH peptide set forth in SEQ ID NO: 36 having additionally at least one CTP amino acid peptide on the N-terminus and at least one CTP amino acid peptide on the C-terminus for improving immunity. In another embodiment, the methods of the present invention provide a GH peptide set forth in SEQ ID NO: 37 having additionally at least one CTP amino acid peptide on the N-terminus for improving immunity. In another embodiment, the methods of the present invention provide a GH peptide set forth in SEQ ID NO: 38 having additionally at least one CTP amino acid peptide on the N-terminus for improving immunity. In another embodiment, the methods of the present invention provide a GH peptide set forth in SEQ ID NO: 39 for improving immunity. In another embodiment, the methods of the present invention provide a GH peptide set forth in SEQ ID NO: 40 for improving immunity. In another embodiment, the methods of the present invention provide a GH peptide set forth in SEQ ID NO: 41 for improving immunity. In another embodiment, the methods of the present invention provide a GH peptide set forth in SEQ ID NO: 42 having additionally at least one CTP amino acid peptide on the N-terminus for improving immunity. In another embodiment, the methods of the present invention provide a GH peptide modified by CTPs, as provided herein, for improving immunity.

In another embodiment, the methods of the present invention provide a nucleic acid sequence encoding a GH peptide having additionally at least one CTP amino acid peptide on the N-terminus and at least one CTP amino acid peptide on the C-terminus for improving immunity. In another embodiment, the methods of the present invention provide a nucleic acid sequence encoding a GH peptide having additionally one CTP amino acid peptide on the N-terminus and two CTP amino acid peptides on the C-terminus for improving immunity. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving immunity. In another embodiment, the methods of the present invention provide a nucleic acid of SEQ ID NO: 46 encoding a GH peptide and one CTP amino acid peptide on the N-terminus and two CTP amino acid peptides on the C-terminus for improving immunity.

In another embodiment, the methods of the present invention provide a GH peptide having additionally at least one CTP amino acid peptide on the N-terminus and at least one CTP amino acid peptide on the C-terminus for regrowing vital organs. In another embodiment, the methods of the present invention provide a GH peptide having additionally one CTP amino acid peptide on the N-terminus and two CTP amino acid peptides on the C-terminus for regrowing vital organs. In another embodiment, the methods of the present invention provide a GH peptide set forth in SEQ ID NO: 23 having additionally at least one CTP amino acid peptide on the N-terminus and at least one CTP amino acid peptide on the C-terminus for regrowing vital organs. In another embodiment, the methods of the present invention provide a GH peptide set forth in SEQ ID NO: 36 having additionally at least one CTP amino acid peptide on the N-terminus and at least one CTP amino acid peptide on the C-terminus for regrowing vital organs. In another embodiment, the methods of the present invention provide a GH peptide set forth in SEQ ID NO: 37 having additionally at least one CTP amino acid peptide on the N-terminus for regrowing vital organs. In another embodiment, the methods of the present invention provide a GH peptide set forth in SEQ ID NO: 38 having additionally at least one CTP amino acid peptide on the N-terminus for regrowing vital organs. In another embodiment, the methods of the present invention provide a GH peptide set forth in SEQ ID NO: 39 for regrowing vital organs. In another embodiment, the methods of the present invention provide a GH peptide set forth in SEQ ID NO: 40 for regrowing vital organs. In another embodiment, the methods of the present invention provide a GH peptide set forth in SEQ ID NO: 41 for regrowing vital organs. In another embodiment, the methods of the present invention provide a GH peptide set forth in SEQ ID NO: 42 having additionally at least one CTP amino acid peptide on the N-terminus for regrowing vital organs. In another embodiment, the methods of the present invention provide a GH peptide modified by CTPs, as provided herein, for regrowing vital organs.

In another embodiment, the methods of the present invention provide a nucleic acid sequence encoding a GH peptide having additionally at least one CTP amino acid peptide on the N-terminus and at least one CTP amino acid peptide on the C-terminus for regrowing vital organs. In another embodiment, the methods of the present invention provide a nucleic acid sequence encoding a GH peptide having additionally one CTP amino acid peptide on the N-terminus and two CTP amino acid peptides on the C-terminus for regrowing vital organs. In another embodiment, the methods of the present invention provide a nucleic acid of SEQ ID NO: 45 encoding a GH peptide comprising one CTP amino acid peptide on the N-terminus and two CTP amino acid peptides on the C-terminus for regrowing vital organs. In another embodiment, the methods of the present invention provide a nucleic acid of SEQ ID NO: 46 encoding a GH peptide and one CTP amino acid peptide on the N-terminus and two CTP amino acid peptides on the C-terminus for regrowing vital organs.

In another embodiment, the methods of the present invention provide a GH peptide of the present invention for increasing sense of well-being.

In another embodiment, the methods of the present invention provide a GH peptide having additionally at least one CTP amino acid peptide on the N-terminus and at least one CTP amino acid peptide on the C-terminus for restoring REM sleep. In another embodiment, the methods of the present invention provide a GH peptide having additionally one CTP amino acid peptide on the N-terminus and two CTP amino acid peptides on the C-terminus for restoring REM sleep. In another embodiment, the methods of the present invention provide a GH peptide set forth in SEQ ID NO: 23 having additionally at least one CTP amino acid peptide on the N-terminus and at least one CTP amino acid peptide on the C-terminus for restoring REM sleep. In another embodiment, the methods of the present invention provide a GH peptide set forth in SEQ ID NO: 36 having additionally at least one CTP amino acid peptide on the N-terminus and at least one CTP amino acid peptide on the C-terminus for restoring REM sleep. In another embodiment, the methods of the present invention provide a GH peptide set forth in SEQ ID NO: 37 having additionally at least one CTP amino acid peptide on the N-terminus for restoring REM sleep. In another embodiment, the methods of the present invention provide a GH peptide set forth in SEQ ID NO: 38 having additionally at least one CTP amino acid peptide on the N-terminus for restoring REM sleep. In another embodiment, the methods of the present invention provide a GH peptide set forth in SEQ ID NO: 39 for restoring REM sleep. In another embodiment, the methods of the present invention provide a GH peptide set forth in SEQ ID NO: 40 for restoring REM sleep. In another embodiment, the methods of the present invention provide a GH peptide set forth in SEQ ID NO: 41 for restoring REM sleep. In another embodiment, the methods of the present invention provide a GH peptide set forth in SEQ ID NO: 42 having additionally at least one CTP amino acid peptide on the N-terminus for restoring REM sleep. In another embodiment, the methods of the present invention provide a GH peptide modified by CTPs, as provided herein, for restoring REM sleep.

In another embodiment, the methods of the present invention provide a nucleic acid sequence encoding a GH peptide having additionally at least one CTP amino acid peptide on the N-terminus and at least one CTP amino acid peptide on the C-terminus for restoring REM sleep. In another embodiment, the methods of the present invention provide a nucleic acid sequence encoding a GH peptide having additionally one CTP amino acid peptide on the N-terminus and two CTP amino acid peptides on the C-terminus for restoring REM sleep. In another embodiment, the methods of the present invention provide a nucleic acid of SEQ ID NO: 45 encoding a GH peptide comprising one CTP amino acid peptide on the N-terminus and two CTP amino acid peptides on the C-terminus for restoring REM sleep. In another embodiment, the methods of the present invention provide a nucleic acid of SEQ ID NO: 46 encoding a GH peptide and one CTP amino acid peptide on the N-terminus and two CTP amino acid peptides on the C-terminus for restoring REM sleep.

In another embodiment, the methods of the present invention provide a nucleic acid sequence encoding a GH protein as described herein. In another embodiment, the methods of the present invention provide a nucleic acid sequence encoding polypeptide comprising hGH modified by CTPs for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof.

In some embodiments, "homology" according to the present invention also encompasses deletions, insertions, or substitution variants, including an amino acid substitution, thereof and biologically active polypeptide fragments thereof. In one embodiment the substitution variant is one in which the glutamine in position 65 of hGH is substituted by a valine [Gellerfors et al., J Pharm Biomed Anal 1989, 7:173-83].

In another embodiment, the nucleic acid molecule encoding a growth hormone as described herein encodes any amino acid sequence of a growth hormone known to one of skill in the art. In another embodiment, the nucleic acid molecule encoding a growth hormone as described herein encodes an hGH. In another embodiment, the nucleic acid molecule encoding a growth hormone comprises the gene bank nucleic acid deposited sequence under accession no. NM_000515.3. In another embodiment, the nucleic acid molecule encoding a growth hormone comprises the gene bank nucleic acid deposited sequence under accession no. NM_022559.2. In another embodiment, the nucleic acid molecule encoding a growth hormone comprises the gene bank nucleic acid deposited sequence under accession no. NM_022560.2. In another embodiment, the nucleic acid molecule encoding a growth hormone comprises the gene bank nucleic acid deposited sequence under accession no. NM_022561.2. In another embodiment, the nucleic acid molecule encoding a growth hormone comprises the gene bank nucleic acid deposited sequence under accession no. NM_022562.2.

In some embodiments, interferon is utilized according to the teachings of the present invention. In some embodiments, the attachment of CTP sequence to both the amino and carboxy termini of the interferon protein results in increased potency. In some embodiments, the attachment of CTP sequence to both the amino and carboxy termini of the interferon protein results in prolonged in-vivo activity.

In one embodiment, "interferon" refers to the mammalian interferon polypeptide Type I. In one embodiment, "interferon" refers to the mammalian interferon polypeptide Type II. In some embodiments, additional suitable interferon polypeptides as known to those of ordinary skill in the art are utilized. In some embodiments, the interferon is alpha-interferon. In some embodiments, the interferon is beta-interferon. In some embodiments, the interferon is gamma-interferon. In some embodiments, the interferon is omega-interferon. In some embodiments, the interferon is a subspecies interferon. In one embodiment, the subspecies of interferon (IFN) is IFN-α2a. In one embodiment, the subspecies of interferon (IFN) is IFN-α2b. In one embodiment, the subspecies of interferon (IFN) is IFN-β1a. In one embodiment, the interferon (IFN) subspecies is IFN-β1b.

In one embodiment, interferon of the present invention exhibits interferon activity, such as antiviral or antiproliferative activity. In some embodiments, GenBank=Accession Numbers of non-limiting examples of interferons are listed in Table 1 below.

In one embodiment, an interferon of the present invention also refers to homologues. In one embodiment, an interferon amino acid sequence of the present invention is at least 50% homologous to an interferon sequence disclosed herein. In one embodiment, an interferon amino acid sequence of the present invention is at least 60% homologous an interferon sequence disclosed herein. In one embodiment, an interferon amino acid sequence of the present invention is at least 70% homologous an interferon sequence disclosed herein. In one embodiment, an interferon amino acid sequence of the present invention is at least 80% homologous to an interferon sequence disclosed herein). In one embodiment, interferon amino acid sequence of the present invention is at least 90% homologous to an interferon sequence disclosed herein. In one embodiment, an interferon amino acid sequence of the present invention is at least 95% homologous an interferon sequence disclosed herein. In some embodiments, homology according to the present invention also encompasses deletions, insertions, or substitution variants, including an amino acid substitution, thereof and biologically active polypeptide fragments thereof. In one embodiment the cysteine in position 17 of interferon β is substituted by a serine (SEQ ID NO: 24).

Table 1 below lists examples of interferons with their respective NCBI sequence numbers

TABLE 1

| Interferon name | NCBI sequence number |
| --- | --- |
| interferon, α 1 | NP_076918.1 |
| interferon, α 10 | NP_002162.1 |
| interferon, α13 | NP_008831.2 |
| interferon, α14 | NP_002163.1 |
| interferon, α16 | NP_002164.1 |
| interferon, α17 | NP_067091.1 |
| interferon, α2 | NP_000596.2 |
| interferon, α21 | NP_002166.1 |
| interferon, α4 | NP_066546.1 |
| interferon, α5 | NP_002160.1 |
| interferon, α6 | NP_066282.1 |
| interferon, α7 | NP_066401.2 |
| interferon, α8 | NP_002161.2 |
| interferon, β 1 | NP_002167.1 |
| interferon, ε1 | NP_795372.1 |
| interferon, γ | NP_000610.2 |
| interferon, ε | NP_064509.1 |
| interferon, Ω1 | NP_002168.1 |

In another embodiment, the methods of the present invention provide an interferon beta 1 peptide having additionally at least one CTP amino acid peptide on the N-terminus and at least one CTP amino acid peptide on the C-terminus for treating or inhibiting multiple sclerosis. In another embodiment, the methods of the present invention provide an interferon beta 1 peptide having additionally one CTP amino acid peptide on the N-terminus and two CTP amino acid peptides on the C-terminus for treating or inhibiting multiple sclerosis. In another embodiment, the methods of the present invention provide an interferon beta 1 peptide set forth in SEQ ID NO: 24 having additionally at least one CTP amino acid peptide on the N-terminus and one CTP amino acid peptide on the C-terminus for treating or inhibiting multiple sclerosis. In another embodiment, the methods of the present invention provide an interferon beta 1 peptide set forth in SEQ ID NO: 24 having additionally on the N-terminus the signal peptide of SEQ ID NO: 26 and at least one CTP amino acid peptide on the N-terminus of SEQ ID NO: 26 and at least one CTP amino acid peptide on the C-terminus of SEQ ID NO: 24 for treating or inhibiting multiple sclerosis.

In some embodiments, glucagon-like peptide-1 is utilized according to the teachings of the present invention. In some embodiments, the attachment of CTP sequences to both the amino and carboxy termini of a "glucagon-like peptide-1" results in increased potency. In some embodiments, the attachment of CTP sequences to both the amino and carboxy termini of a peptide results in prolonged in-vivo activity. In some embodiments, the attachment of CTP sequences to both the amino and carboxy termini of the glucagon-like peptide-results in prolonged in-vivo activity.

In one embodiment, "glucagon-like peptide-1" (GLP-1) refers to a mammalian polypeptide. In one embodiment, "glucagon-like peptide-1" (GLP-1) refers to a human polypeptide. In some embodiments, GLP-1 is cleaved from the glucagon preproprotein (Genbank ID No. NP002045) that has the ability to bind to the GLP-1 receptor and initiate a signal transduction pathway resulting in insulinotropic activity. In one embodiment, "insulinotropic activity" refers to the ability to stimulate insulin secretion in response to elevated glucose levels, thereby causing glucose uptake by cells and decreased plasma glucose levels. In some embodiments, GLP-1 polypeptides include, but are not limited to those described in U.S. Pat. No. 5,118,666; which is incorporated by reference herein.

In one embodiment, "GLP-1" refers to a polypeptide, such as set forth in sequences set forth in SEQ ID NO: 25 as determined using BlastP software of the National Center of Biotechnology Information (NCBI) using default parameters. In one embodiment, a GLP-1 of the present invention also refers to a GLP-1 homologue. In one embodiment, a GLP-1 amino acid sequence of the present invention is at least 50% homologous to GLP-1 sequences set forth in SEQ ID NO: 25 as determined using BlastP software of the National Center of Biotechnology Information (NCBI) using default parameters. In one embodiment, aGLP-1 amino acid sequence of the present invention is at least 60% homologous to GLP-1 sequences set forth in SEQ ID NO: 25 as determined using BlastP software of the National Center of Biotechnology Information (NCBI) using default parameters. In one embodiment, aGLP-1 amino acid sequence of the present invention is at least 70% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 80% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 90% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 95% homologous to GLP-1 sequences set forth in SEQ ID NO: 25 as determined using BlastP software of the National Center of Biotechnology Information (NCBI) using default parameters.

In another embodiment, the methods of the present invention provide a GLP-1 peptide having additionally at least one CTP amino acid peptide on the N-terminus and at least one CTP amino acid peptide on the C-terminus for treating or inhibiting type II diabetes. In another embodiment, the methods of the present invention provide a GLP-1 peptide having additionally one CTP amino acid peptide on the N-terminus and two CTP amino acid peptides on the C-terminus for treating or inhibiting type II diabetes. In another embodiment, the methods of the present invention provide a GLP-1 peptide set forth in SEQ ID NO: 25 having additionally at least one CTP amino acid peptide on the N-terminus and at least one CTP amino acid peptide on the C-terminus for treating or inhibiting tune II diabetes.

In one embodiment, the homologue also refers to a deletion, insertion, or substitution variant, including an amino acid substitution, thereof and biologically active polypeptide fragments thereof.

In one embodiment the polypeptide sequence of interest is an EPO. In one embodiment the polypeptide sequence of interest is an interferon. In another embodiment the polypeptide sequence of interest is an hGH. In another embodiment the polypeptide sequence of interest is a GLP-1. In another embodiment the polypeptide sequence of interest is an insulin. In another embodiment the polypeptide sequence of interest is enkephalin. In another embodiment the polypeptide sequence of interest is an ACTH. In another embodiment the polypeptide sequence of interest is a glucagon. In another embodiment the polypeptide sequence of interest is an insulin-like growth factor. In another embodiment the polypeptide sequence of interest is an epidermal growth factor. In another embodiment the polypeptide sequence of interest is an acidic or basic fibroblast growth factor. In another embodiment the polypeptide sequence of interest is a platelet-derived growth factor. In another embodiment the polypeptide sequence of interest is a granulocyte-CSF. In another embodiment the polypeptide sequence of interest is a macrophage-CSF. In another embodiment the polypeptide sequence of interest is an IL-2. In another embodiment the polypeptide sequence of interest is an IL-3. In another embodiment the polypeptide sequence of interest is a tumor necrosis factor. In another embodiment the polypeptide sequence of interest is an LHRH. In another embodiment the polypeptide sequence of interest is an LHRH analog. In another embodiment the polypeptide sequence of interest is a somatostatin. In another embodiment the polypeptide sequence of interest is a growth hormone releasing factor. In another embodiment the polypeptide sequence of interest is an endorphin. In another embodiment the polypeptide sequence of interest is an alveolar surfactant protein. In another embodiment the polypeptide sequence of interest is a natriuretic factor. In another embodiment the polypeptide sequence of interest is an adhesion. In another embodiment the polypeptide sequence of interest is an angiostatin. In another embodiment the polypeptide sequence of interest is an endostatin. In another embodiment the polypeptide sequence of interest is a receptor peptide. In another embodiment the polypeptide sequence of interest is a receptor binding ligand. In another embodiment the polypeptide sequence of interest is an antibody. In another embodiment the polypeptide sequence of interest is an antibody fragment. In another embodiment the polypeptide sequence of interest is a peptide or a protein including any modified form.

In another embodiment, the peptide of the invention comprises a peptide of interest having additionally at least one CTP amino acid peptide on the N-terminus and one CTP amino acid peptide on the C-terminus. In another embodiment, the peptide of interest having additionally at least one CTP amino acid peptide on the N-terminus and one CTP amino acid peptide on the C-terminus comprises a protein selected from the following list: insulin, Albutein/albumin, Activase® Alteplase/tPA, adenosine deaminase, immune globulin, glucocerebrosidase, Leukine-sargramostim/GM-CSF, G-CSF, Venoglobulin-S/IgG, Proleukin aldesleukin, DNase, Factor VIII, Helixate, L-asparaginase, WinRho SDF Rh I, Retavase retaplase/tPA, Factor IX, FSH, globulin, fibrin, interleukin-11, becaplermin/PDGF, lepirudin/herudin, TNF, Thymoglobulin, Factor VIIa, interferon alpha-2a, interferon alfa n-1, interferon alfa-N3, interferon beta-1b, interferon gamma-1b, Interleukin-2, HGH, or monoclonal antibodies.

In another embodiment, the methods of the present invention provide insulin having additionally at least one CTP amino acid peptide on the N-terminus and one CTP amino acid peptide on the C-terminus for the treatment of diabetes.

In another embodiment, the methods of the present invention provide albumin having additionally at least one CTP amino acid peptide on the N-terminus and one CTP amino acid peptide on the C-terminus for the treatment of hypovolemic shock, hemodialysis or cardiopulmonary bypass.

In another embodiment, the methods of the present invention provide Activase-altiplase/tPA having additionally at least one CTP amino acid peptide on the N-terminus and one CTP amino acid peptide on the C-terminus for the treatment of acute myocardial infarction, acute massive pulmonary embolism, or ischemic stroke.

In another embodiment, the methods of the present invention provide adenosine deaminase having additionally at least one CTP amino acid peptide on the N-terminus and one CTP amino acid peptide on the C-terminus for the treatment of severe combined immunodeficiency disease.

In another embodiment, the methods of the present invention provide immune globulin having additionally at least one CTP amino acid peptide on the N-terminus and one CTP amino acid peptide on the C-terminus for the treatment of transplant recipients.

In another embodiment, the methods of the present invention provide a CMV immune globulin. In another embodiment, the methods of the present invention provide glucocerebrosidase having additionally at least one CTP amino acid peptide on the N-terminus and one CTP amino acid peptide on the C-terminus for the treatment of Gaucher disease.

In another embodiment, the methods of the present invention provide Leukine-sargramostim/GM-CSF having additionally at least one CTP amino acid peptide on the N-terminus and one CTP amino acid peptide on the C-terminus for the Stimulation of hematopoietic progenitor cells.

In another embodiment, the methods of the present invention provide G-CSF having additionally at least one CTP amino acid peptide on the N-terminus and one CTP amino acid peptide on the C-terminus for the treatment of Neutropenia. In another embodiment, the methods of the present invention provide Venoglobulin-S/IgG having additionally at least one CTP amino acid peptide on the N-terminus and one CTP amino acid peptide on the C-terminus for the treatment of Immunodeficiency diseases.

In another embodiment, the methods of the present invention provide Proleukin (aldesleukin) having additionally at least one CTP amino acid peptide on the N-terminus and one CTP amino acid peptide on the C-terminus for the treatment of renal carcinoma or metastatic melanoma.

In another embodiment, the methods of the present invention provide DNase having additionally at least one CTP amino acid peptide on the N-terminus and one CTP amino acid peptide on the C-terminus for the treatment of Cystic fibrosis.

In another embodiment, the methods of the present invention provide Factor VIII having additionally at least one CTP amino acid peptide on the N-terminus and one CTP amino acid peptide on the C-terminus for the treatment of Hemophilia A.

In another embodiment, the methods of the present invention provide Helixate having additionally at least one CTP amino acid peptide on the N-terminus and one CTP amino acid peptide on the C-terminus for the treatment of Hemophilia A.

In another embodiment, the methods of the present invention provide L-asparaginase having additionally at least one CTP amino acid peptide on the N-terminus and one CTP amino acid peptide on the C-terminus for the treatment of acute lymphoblastic leukemia.

In another embodiment, the methods of the present invention provide WinRho SDF Rh IgG having additionally at least one CTP amino acid peptide on the N-terminus and one CTP amino acid peptide on the C-terminus for the treatment of Rh isoimmunization and immune thrombocytopenic purpura.

In another embodiment, the methods of the present invention provide Retavase retaplase/tPA having additionally at least one CTP amino acid peptide on the N-terminus and one CTP amino acid peptide on the C-terminus for the treatment of acute myocardial infarction.

In another embodiment, the methods of the present invention provide Factor IX having additionally at least one CTP amino acid peptide on the N-terminus and at least one CTP amino acid peptide on the C-terminus for the treatment of Hemophilia B.

In another embodiment, the methods of the present invention provide FSH having additionally at least one CTP amino acid peptide on the N-terminus and at least one CTP amino acid peptide on the C-terminus for stimulation of ovulation during assisted reproduction.

In another embodiment, the methods of the present invention provide globulin having additionally at least one CTP amino acid peptide on the N-terminus and at least one CTP amino acid peptide on the C-terminus for the prevention of respiratory syncytial virus disease.

In another embodiment, the methods of the present invention provide fibrin having additionally at least one CTP amino acid peptide on the N-terminus and at least one CTP amino acid peptide on the C-terminus for wound management and hemostasis. In another embodiment, the methods of the present invention provide interleukin-11 having additionally at least one CTP amino acid peptide on the N-terminus and at least one CTP amino acid peptide on the C-terminus for chemotherapy-induced thrombocytopenia.

In another embodiment, the methods of the present invention provide becaplermin/PDGF having additionally at least one CTP amino acid peptide on the N-terminus and at least one CTP amino acid peptide on the C-terminus for the treatment of diabetic foot ulcers.

In another embodiment, the methods of the present invention provide lepirudin/herudin having additionally at least one CTP amino acid peptide on the N-terminus and at least one CTP amino acid peptide on the C-terminus for anticoagulation in heparin-induced thrombocytopenia.

In another embodiment, the methods of the present invention provide soluble TNF having additionally at least one CTP amino acid peptide on the N-terminus and at least one CTP amino acid peptide on the C-terminus for the treatment of rheumatoid arthritis.

In another embodiment, the methods of the present invention provide Thymoglobulin having additionally at least one CTP amino acid peptide on the N-terminus and at least one CTP amino acid peptide on the C-terminus for the treatment of organ transplant rejection disease.

In another embodiment, the methods of the present invention provide Factor VIIa having additionally at least one CTP amino acid peptide on the N-terminus and at least one CTP amino acid peptide on the C-terminus for the treatment of hemophilia.

In another embodiment, the methods of the present invention provide interferon alpha-2a having additionally at least one CTP amino acid peptide on the N-terminus and at least one CTP amino acid peptide on the C-terminus for the treatment of hairy cell leukemia and AIDS-related Kaposi's sarcoma.

In another embodiment, the methods of the present invention provide interferon alpha-2b having additionally at least one CTP amino acid peptide on the N-terminus and at least one CTP amino acid peptide on the C-terminus for the treatment of Hairy cell leukemia, genital warts, AIDS-related Kaposi's sarcoma, Hepatitis C, Hepatitis B, malignant melanoma, and follicular lymphoma.

In another embodiment, the methods of the present invention provide interferon alfa-N3 having additionally at least one CTP amino acid peptide on the N-terminus and at least one CTP amino acid peptide on the C-terminus for the treatment of genital warts.

In another embodiment, the methods of the present invention provide interferon gamma-1b having additionally at least one CTP amino acid peptide on the N-terminus and at least one CTP amino acid peptide on the C-terminus for the treatment of chronic granulomatous disease.

In another embodiment, the methods of the present invention provide interferon alfa n-1 having additionally at least one CTP amino acid peptide on the N-terminus and at least one CTP amino acid peptide on the C-terminus for the treatment of Hepatitis C infection.

In another embodiment, the methods of the present invention provide Interleukin-2 having additionally at least one CTP amino acid peptide on the N-terminus and at least one CTP amino acid peptide on the C-terminus for the treatment of renal carcinoma and metastatic melanoma.

In another embodiment, the methods of the present invention provide interferon beta-1b having additionally at least one CTP amino acid peptide on the N-terminus and at least one CTP amino acid peptide on the C-terminus for the treatment of multiple sclerosis.

In another embodiment, the methods of the present invention provide hGH having additionally at least one CTP amino acid peptide on the N-terminus and at least one CTP amino acid peptide on the C-terminus for the treatment of wasting disease, AIDS, cachexia, or hGH deficiency.

In another embodiment, the methods of the present invention provide an OKT3 monoclonal antibody having additionally at least one CTP amino acid peptide on the N-terminus and at least one CTP amino acid peptide on the C-terminus for organ transplant.

In another embodiment, the methods of the present invention provide a Reo monoclonal antibody having additionally at least one CTP amino acid peptide on the N-terminus and at least one CTP amino acid peptide on the C-terminus for prevention of complications from coronary intervention and angioplasty.

In another embodiment, the methods of the present invention provide a monoclonal antibody having additionally at least one CTP amino acid peptide on the N-terminus and at least one CTP amino acid peptide on the C-terminus for treating colorectal cancer, Non-Hodgkin's lymphoma, kidney transplant rejection, metastatic breast cancer, or the prevention of respiratory syncytial virus disease.

In one embodiment, the invention is employed in veterinary medicine. In one embodiment, the present invention provides treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

In one embodiment, polypeptides, antibodies, or polynucleotides of the present invention are administered to an animal (e.g., mouse, rat, rabbit, hamster, guinea pig, pigs, micro-pig, chicken, camel, goat, horse, cow, sheep, dog, cat, non-human primate, and human. In one embodiment, the recited applications have uses in a wide variety of hosts. In some embodiments, such hosts include, but are not limited to, human, murine, rabbit, goat, guinea pig, camel, horse, mouse, rat, hamster, pig, micro-pig, chicken, goat, cow, sheep, dog, cat, or non-human primate.

In one embodiment, farm animals are treated by the methods of the present invention. In one embodiment, farm animals include pigs, cattle, dairy cows, horses, goats, sheep, chickens, turkeys, geese, ducks and related species. In one embodiment, laboratory animals are treated by the methods of the present invention. In one embodiment, laboratory animals include rats, mice, guinea pigs, rabbits, goats, monkeys, dogs, cats and others. In one embodiment, zoo animals are treated by the methods of the present invention. In one embodiment, zoo animals include all vertebrate animals kept in zoos. In one embodiment, aquatic animals are treated by the methods of the present invention. In one embodiment, aquatic animals include fish, eels, turtles, seals, penguins, sharks, whales, and related species. In one embodiment, domesticated animals are treated by the methods of the present invention. In one embodiment, domesticated animals include any pet, such as cats and dogs, or animal that is kept by humans, e.g., horses, cattle, pigs, goats, rabbits, chickens, turkeys, geese, ducks and the like.

According to the present invention the term pigs includes pigs, piglets, hogs, gilts, barrows, boars and sows. In another embodiment, "cattle" refers to calves, cows, dairy cows, heifers, steers and bulls.

In one embodiment, bovine growth hormone is utilized by the methods of the present invention. In one embodiment, artificial bovine growth hormone is utilized by the methods of the present invention. In one embodiment, the artificial bovine growth hormone has a sequence set forth in NCBI sequence ID number AAA72262. In another embodiment, the artificial bovine growth hormone is any other artificial bovine growth hormone known in the art. Each possibility represents a separate embodiment of the present invention.

In one embodiment, sheep growth hormone is utilized by the methods of the present invention. In one embodiment, sheep growth hormone has a sequence set forth in NCBI sequence ID number NP_001009315. In another embodiment, the sheep growth hormone is any other sheep growth hormone known in the art. Each possibility represents a separate embodiment of the present invention.

In one embodiment, horse growth hormone is utilized by the methods of the present invention. In one embodiment, horse growth hormone has a sequence set forth in NCBI sequence ID number AAA21027. In another embodiment, the horse growth hormone is any other horse growth hormone known in the art. Each possibility represents a separate embodiment of the present invention.

In one embodiment, chicken growth hormone is utilized by the methods of the present invention. In one embodiment, chicken growth hormone has a sequence set forth in NCBI sequence ID number CAA3561. In another embodiment, the chicken growth hormone is any other chicken growth hormone known in the art. Each possibility represents a separate embodiment of the present invention.

In one embodiment, murine growth hormone is utilized by the methods of the present invention. In one embodiment, the murine growth hormone has a sequence set forth in NCBI sequence ID number NP_032143. In another embodiment, the murine growth hormone is any other murine growth hormone known in the art. Each possibility represents a separate embodiment of the present invention.

In one embodiment, tilapia growth hormone is utilized by the methods of the present invention. In one embodiment, the tilapia growth hormone has a sequence set forth in NCBI sequence ID number CAA00818. In another embodiment, the tilapia growth hormone is any other tilapia growth hormone known in the art. Each possibility represents a separate embodiment of the present invention.

In one embodiment, bovine EPO is utilized by the methods of the present invention. In one embodiment, artificial bovine growth hormone is utilized by the methods of the present invention. In one embodiment, artificial bovine growth hormone has a sequence set forth in NCBI sequence ID number NP_776334. In another embodiment, the bovine EPO is any other bovine EPO known in the art. Each possibility represents a separate embodiment of the present invention.

In one embodiment, pig EPO is utilized by the methods of the present invention. In one embodiment, pig EPO has a sequence set forth in NCBI sequence ID number NP_999299. In another embodiment, the pig EPO is any other pig EPO known in the art. Each possibility represents a separate embodiment of the present invention.

In one embodiment, sheep EPO is utilized by the methods of the present invention. In one embodiment, sheep growth hormone has a sequence set forth in NCBI sequence ID number NP_001019908. In another embodiment, the sheep growth hormone is any other sheep growth hormone known in the art. Each possibility represents a separate embodiment of the present invention.

In one embodiment, murine EPO is utilized by the methods of the present invention. In one embodiment, the murine growth hormone has a sequence set forth in NCBI sequence ID number CAA72707. In another embodiment, the murine growth hormone is any other murine growth hormone known in the art. Each possibility represents a separate embodiment of the present invention.

In one embodiment, bovine GLP-1 is utilized by the methods of the present invention. In one embodiment, bovine GLP-1 has a sequence set forth in NCBI sequence ID number P01272. In another embodiment, the bovine GLP-1 is any other bovine GLP-1 known in the art. Each possibility represents a separate embodiment of the present invention.

In one embodiment, sheep GLP-1 is utilized by the methods of the present invention. In one embodiment, sheep GLP-1 has a sequence set forth in NCBI sequence ID number Q8MJ25. In another embodiment, the sheep GLP-1 is any other sheep GLP-1 known in the art. Each possibility represents a separate embodiment of the present invention.

In one embodiment, pig GLP-1 is utilized by the methods of the present invention. In one embodiment, chicken GLP-1 has a sequence set forth in NCBI sequence ID number P01274. In another embodiment, the chicken GLP-1 is any other chicken GLP-1 known in the art. Each possibility represents a separate embodiment of the present invention.

In one embodiment, murine GLP-1 is utilized by the methods of the present invention. In one embodiment, the murine GLP-1 has a sequence set forth in NCBI sequence ID number NP_032127. In another embodiment, the murine GLP-1 is any other murine GLP-1 known in the art. Each possibility represents a separate embodiment of the present invention.

In one embodiment, bovine interferon alpha is utilized by the methods of the present invention. In one embodiment, bovine interferon alpha has a sequence set forth in NCBI sequence ID number ABD57311. In another embodiment, the bovine interferon alpha is any other bovine interferon alpha known in the art. Each possibility represents a separate embodiment of the present invention.

In one embodiment, sheep interferon alpha is utilized by the methods of the present invention. In one embodiment, sheep interferon alpha has a sequence set forth in NCBI sequence ID number CAA41790. In another embodiment, the sheep interferon alpha is any other sheep interferon alpha known in the art. Each possibility represents a separate embodiment of the present invention.

In one embodiment, pig interferon alpha is utilized by the methods of the present invention. In one embodiment, chicken interferon alpha has a sequence set forth in NCBI sequence ID number AAP92118. In another embodiment, the pig interferon alpha is any other pig interferon alpha known in the art. Each possibility represents a separate embodiment of the present invention.

In one embodiment, murine interferon alpha is utilized by the methods of the present invention. In one embodiment, the murine interferon alpha has a sequence set forth in NCBI sequence ID number AAA37886. In another embodiment, the murine interferon alpha is any other murine interferon alpha known in the art. Each possibility represents a separate embodiment of the present invention.

In some embodiments, the CTP sequences modification is advantageous in permitting lower dosages to be used.

In some embodiments, "polypeptide" as used herein encompasses native polypeptides (either degradation products, synthetically synthesized polypeptides or recombinant polypeptides) and peptidomimetics (typically, synthetic polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinbelow.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the polypeptides of the present invention are utilized in a linear form, although it will be appreciated by one skilled in the art that in cases where cyclicization does not severely interfere with polypeptide characteristics, cyclic forms of the polypeptide can also be utilized.

In some embodiments, the polypeptides of the present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide of the present invention is synthesized using a polynucleotide encoding a polypeptide of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention.

In some embodiments, polynucleotides which express the polypeptides of the present invention are as set forth in SEQ ID NOs: 20, 21, 44, 45 and 46.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In some embodiments, signal sequences include, but are not limited to the endogenous signal sequence for EPO as set forth in SEQ ID NO: 19 or the endogenous signal sequence for IFN-β1 as set forth in SEQ ID NO: 26. In another embodiment, the signal sequence is N-terminal to the CTP sequence that is in turn N-terminal to the polypeptide sequence of interest; e.g. the sequence is (a) signal sequence-(b) CTP-(c) sequence of interest-(d) optionally 1 or more additional CTP sequences. In another embodiment, 1 or more CTP sequences is inserted between the signal sequence of a polypeptide sequence of interest and the polypeptide sequence of interest itself, thus interrupting the wild-type sequence of interest. Each possibility represents a separate embodiment of the present invention.

In another embodiment, the growth hormone further comprises a signal peptide. In some embodiments, signal sequences include, but are not limited to the endogenous signal sequence. In some embodiments, signal sequences include, but are not limited to the endogenous signal sequence of any known growth hormone or growth hormones. In another embodiment, the polypeptides and methods of the present invention provide a growth hormone having additionally a signal peptide of comprising the following amino acid sequence: MATGSRTSLLLAFGLL-CLPWLQEGSA (SEQ ID NO: 49).

In one embodiment, following expression and secretion, the signal peptides are cleaved from the precursor proteins resulting in the mature proteins. For example, in the polypeptide set forth in SEQ ID NO: 3, described herein and diagramed in FIG. 1C, amino acids 1-27 (SEQ ID NO: 19), presented above, represent the amino acid sequence of the signal peptide sequence, and amino acids 28-277 of SEQ ID NO: 3, SSSSKAPPPSLPSPSRLPGPSDTPILPQAP-PRLICDSRVLERYLLEAKEAENITTGCAEHCSLNENIT-VPDTKVNFYAWKRMEVGQQAVEVWQGLALLSEAV-LRGQALLVNSSQPWEPLQLHVDKAVSGLRSLTTLL RALGAQKEAISPPDAASAAPLRTITADTFRKLFRVYS-NFLRGKLKLYTGEACRTGDRSSSSKAPPPSLPSPSR-LPGPSDTPILPQSSSSKAP PPSLPSPSRLPGPSDTPILPQ (SEQ ID NO: 51), represent the mature CTP-modified EPO lacking the signal peptide. In one embodiment, the amino acid sequence of a CTP-modified EPO having the structure CTP-EPO-CTP-CTP without the signal peptide is set forth in SEQ ID NO: 51.

In some embodiments, polynucleotides of the present invention are prepared using PCR techniques as described in Example 1, or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using EPO has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in E. coli; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In one embodiment, production of CTP-EPO-CTP polypeptides using recombinant DNA technology is illustrated in Example 1.

In some embodiments, the recombinant polypeptides are synthesized and purified; their therapeutic efficacy can be assayed in vivo or in vitro. In one embodiment, the binding activities of the recombinant EPO polypeptides of the present invention can be ascertained using various assays as described in Examples 2-6 and 8-9. In one embodiment, in vitro binding activity is ascertained by measuring the ability of the polypeptide to stimulate proliferation of TF-1 cells. In one embodiment, in vivo activity is deduced by analyzing heamatocrit levels (FIGS. 3-5) and/or as a percentage of reticulocytes.

In one embodiment, the EPO polypeptides of the present invention can be used to treat a subject, with a variety of erythropoietin-associated conditions. In some embodiments, a subject is a human subject.

In some embodiment, the phrase "erythropoietin-associated conditions" refers to any condition associated with below normal, abnormal, or inappropriate modulation of erythropoietin. In some embodiment, levels of erythropoietin associated with such conditions are determined by any measure accepted and utilized by those of skill in the art. In some embodiment, erythropoietin-associated conditions typically include anemic conditions.

In some embodiment, "anemic conditions" refers to any condition, disease, or disorder associated with anemia. In some embodiment, anemic conditions include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplasic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

In one embodiment, production of GH modified by CTPs using recombinant DNA technology is preformed.

In some embodiments, the recombinant polypeptides are synthesized and purified; their therapeutic efficacy can be assayed either in vivo or in vitro. In one embodiment, the binding activities of the recombinant GH modified by CTPs of the present invention can be ascertained using various assays.

In one embodiment, the present invention comprises CTP-GH-CTP polypeptides. In one embodiment, recombinant DNA technology methods are used for the production of CTP-GH-CTP polypeptides as illustrated in Example 7. In one embodiment, the therapeutic efficacy of the CTP-GH-CTP polypeptides of the present invention is assayed either in vivo. In one embodiment, the therapeutic efficacy of the CTP-GH-CTP polypeptides of the present invention is assayed either in vitro. In one embodiment, the binding activities of the recombinant GH polypeptides of the present invention are measured using Nb2 (a prolactin-dependent rat lymphoma cell line (ECACC Cell Bank)) or a FCD-P1 murine cell line, previously transfected with human growth hormone receptor. In one embodiment, binding of GH to these receptors induces cell proliferation which in one embodiment is measured by the levels of MTT cellular stain as a function of GH activity. In one embodiment, in vivo activity is deduced by measuring weight gain over time in treated growth hormone deficient animals.

In one embodiment, the present invention provides a method of inducing growth or weight gain in a subject, comprising administering to the subject a therapeutically effective amount of a polypeptide comprising a growth hormone, one chorionic gonadotrophin carboxy terminal peptide (CTP) attached to an amino terminus of said growth hormone, and two chorionic gonadotrophin CTPs attached to a carboxy terminus of the growth hormone, thereby inducing growth or weight gain in a subject.

In another embodiment, the present invention provides a method of inducing growth or weight gain in a non-human subject, comprising the step of administering to said non-human subject a therapeutically effective amount of an expression vector comprising a polynucleotide consisting of a nucleic acid encoding a polypeptide, said polypeptide consisting of a non-human growth hormone, one chorionic gonadotrophin carboxy terminal peptide (CTP) attached to the amino terminus of said non-human growth hormone, and two chorionic gonadotrophin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of inducing weight loss or decreasing body fat in a subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby inducing weight loss or decreasing body fat in said subject. In one embodiment, said subject is obese. In another embodiment, said subject is overweight.

In another embodiment, the present invention provides a method of decreasing body fat in a non-human subject, comprising administering to said subject a therapeutically effective amount of an expression vector comprising a polynucleotide, said polynucleotide consisting of a non-human growth hormone, one chorionic gonadotrophin carboxy terminal peptide (CTP) attached to the amino terminus of said non-human growth hormone, and two chorionic gonadotrophin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of decreasing fat deposits in a subject. In another embodiment, the present invention provides a method of increasing muscle mass in a subject. In another embodiment, the present invention provides a method of promoting muscle growth in a subject. In another embodiment, the present invention provides a method of increasing muscle to fat ratio. In another embodiment, the present invention provides a method of decreasing body mass index (BMI) or Quetelet index.

In another embodiment, growth is measured by weight gain. In another embodiment, growth is measured by height gain. In another embodiment, growth is measured by weight gain. In another embodiment, growth is measured by muscle mass gain. In another embodiment, growth is measured by weight gain. In another embodiment, growth is measured by bone mass gain. In another embodiment, growth is measured by weight gain. In another embodiment, growth is measured by muscle mass gain. In another embodiment, the weight gain is due to bone and/or muscle mass gain. In another embodiment, growth is measured by any known measure known to one of skill in the art.

In some embodiment, human growth hormone polypeptides of the present invention can be used to treat a subject, with conditions related to growth and weight, such as a growth deficiency disorder, AIDS wasting, aging, impaired immune function of HIV-infected subjects, a catabolic illness, surgical recovery, a congestive cardiomyopathy, liver transplantation, liver regeneration after hepatectomy, chronic renal failure, renal osteodystrophy, osteoporosis, achondroplasia/hypochondroplasia, skeletal dysplasia, a chronic inflammatory or nutritional disorder such as Crohn's disease, short bowel syndrome, juvenile chronic arthritis, cystic fibrosis, male infertility, X-linked hypophosphatemic rickets, Down's syndrome, Spina bifida, Noonan Syndrome, obesity, impaired muscle strength and fibromyalgia. In some embodiments, interferon polypeptides of the present invention are used to treat a subject, with a variety of conditions such as hairy cell leukemia (HCL), Kaposi's sarcoma (KS), chronic myelogenous leukemia (CML), chronic Hepatitis C (CHC), condylomata acuminata (CA), chronic Hepatitis B, malignant melanoma, follicular non-Hodgkin's lymphoma, multiple sclerosis, chronic granulomatous disease, *Mycobacterium avium* complex (MAC), pulmonary fibrosis and osteoporosis.

In some embodiments, Glucagon-like peptide-1 (GLP-1) polypeptides of the present invention are used to treat a subject with non-insulin dependent diabetes, obesity, stroke, myocardial infarction, stroke, stress-induced hyperglycemia, or irritable bowel syndrome.

In one embodiment, the polypeptides of the present invention can be provided to the individual per se. In one embodiment, the polypeptides of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the polypeptide sequence of interest, which is accountable for the biological effect.

In some embodiments, any of the compositions of this invention will comprise at least two CTP sequences bound to a protein of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which can be used interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

In another embodiment, polypeptides comprising GH modified by CTPs of the present invention are administered in a dose of 1-90 micrograms in 0.1-5 ml solution. In another embodiment, polypeptides comprising GH modified by CTPs are administered in a dose of 1-50 micrograms in 0.1-5 ml solution. In another embodiment, polypeptides comprising GH modified by CTPs are administered in a dose of 1-25 micrograms in 0.1-5 ml solution. In another embodiment, polypeptides comprising GH modified by CTPs are administered in a dose of 50-90 micrograms in 0.1-5 ml solution. In another embodiment, polypeptides comprising GH modified by CTPs are administered in a dose of 10-50 micrograms in 0.1-5 ml solution.

In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection twice a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection three times a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every two weeks. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 17 days. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 19 days weeks.

Various embodiments of dosage ranges are contemplated by this invention. The dosage of the polypeptide of the present invention, in one embodiment, is in the range of 0.05-80 mg/day. In another embodiment, the dosage is in the range of 0.05-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day. In another embodiment, the dosage is in the range of 0.5-50 mg/day. In another embodiment, the dosage is in the range of 5-80 mg/day. In another embodiment, the dosage is in the range of 35-65 mg/day. In another embodiment, the dosage is in the range of 35-65 mg/day. In another embodiment, the dosage is in the range of 20-60 mg/day. In another embodiment, the dosage is in the range of 40-60 mg/day. In another embodiment, the dosage is in a range of 45-60 mg/day. In another embodiment, the dosage is in the range of 40-60 mg/day. In another embodiment, the dosage is in a range of 60-120 mg/day. In another embodiment, the dosage is in the range of 120-240 mg/day. In another embodiment, the dosage is in the range of 40-60 mg/day. In another embodiment, the dosage is in a range of 240-400 mg/day. In another embodiment, the dosage is in a range of 45-60 mg/day. In another embodiment, the dosage is in the range of 15-25 mg/day. In another embodiment, the dosage is in the range of 5-10 mg/day. In another embodiment, the dosage is in the range of 55-65 mg/day.

In one embodiment, the dosage is 20 mg/day. In another embodiment, the dosage is 30 mg/day. In another embodiment, the dosage is 40 mg/day. In another embodiment, the dosage is 50 mg/day. In another embodiment, the dosage is 60 mg/day. In another embodiment, the dosage is 70 mg/day. In another embodiment, the dosage is 80 mg/day. In another embodiment, the dosage is 90 mg/day. In another embodiment, the dosage is 100 mg/day.

The dosage of the GH modified by CTPs of the present invention, in one embodiment, is in the range of 0.005-100 mg/week. In another embodiment, the dosage is in the range of 0.005-5 mg/week. In another embodiment, the dosage is in the range of 0.01-50 mg/week. In another embodiment, the dosage is in the range of 0.1-20 mg/week. In another embodiment, the dosage is in the range of 0.1-10 mg/week. In another embodiment, the dosage is in the range of 0.01-5 mg/week. In another embodiment, the dosage is in the range of 0.001-0.01 mg/week. In another embodiment, the dosage is in the range of 0.001-0.1 mg/week. In another embodiment, the dosage is in the range of 0.1-5 mg/week. In another embodiment, the dosage is in the range of 0.5-50 mg/week. In another embodiment, the dosage is in the range of 0.2-15 mg/week. In another embodiment, the dosage is in the range of 0.8-65 mg/week. In another embodiment, the dosage is in the range of 1-50 mg/week. In another embodiment, the dosage is in the range of 5-10 mg/week. In another embodiment, the dosage is in the range of 8-15 mg/week. In another embodiment, the dosage is in a range of 10-20 mg/week. In another embodiment, the dosage is in the range of 20-40 mg/week. In another embodiment, the dosage is in a range of 60-120 mg/week. In another embodiment, the dosage is in the range of 12-40 mg/week. In another embodiment, the dosage is in the range of 40-60 mg/week. In another embodiment, the dosage is in a range of 50-100 mg/week. In another embodiment, the dosage is in a range of 1-60 mg/week. In another embodiment, the dosage is in the range of 15-25 mg/week. In another embodiment, the dosage is in the range of 5-10 mg/week. In another embodiment, the dosage is in the range of 55-65 mg/week. In another embodiment, the dosage is in the range of 1-5 mg/week.

In another embodiment, the GH dosage given to a subject is 50% of the standard dosage given to a reference subject from the same population of subjects (e.g. children, elderly, men, women, GH deficient, specific nationality, etc). In another embodiment, the dosage is 30% of the dosage given to a subject from a specific population of subjects. In another embodiment, the dosage is 45% of the dosage given to a subject from a specific population of subjects. In another embodiment, the dosage is 100% of the dosage given to a subject from a specific population of subjects.

In another embodiment, the dosage is 1-5 mg/week. In another embodiment, the dosage is 2 mg/week. In another embodiment, the dosage is 4 mg/week. In another embodiment, the dosage is 1.2 mg/week. In another embodiment, the dosage is 1.8 mg/week. In another embodiment, the dosage is approximately the dosages described herein.

In another embodiment, the dosage is 1-5 mg/administration. In another embodiment, the dosage is 2 mg/administration. In another embodiment, the dosage is 4 mg/administration. In another embodiment, the dosage is 1.2 mg/administration. In another embodiment, the dosage is 1.8 mg/administration. In one embodiment, the composition is administered once a week. In another embodiment, the composition is administered once biweekly. In another embodiment, the composition is administered monthly. In another embodiment, the composition is administered daily.

In another embodiment, GH modified by CTPs is formulated in an intranasal dosage form. In another embodiment, GH modified by CTPs is formulated in an injectable dosage form. In another embodiment, GH modified by CTPs is administered to a subject in a dose ranging from 0.0001 mg to 0.6 mg. In another embodiment, GH modified by CTPs is administered to a subject in a dose ranging from 0.001 mg to 0.005 mg. In another embodiment, GH modified by CTPs is administered to a subject in a dose ranging from 0.005 mg to 0.01 mg. In another embodiment, GH modified by CTPs is administered to a subject in a dose ranging from 0.01 mg to 0.3 mg. In another embodiment, a GH modified by CTPs is administered to a subject in a dose in a dose ranging from 0.2 mg to 0.6 mg.

In another embodiment, GH modified by CTPs is administered to a subject in a dose ranging from 1-100 micrograms. In another embodiment, a GH modified by CTPs is administered to a subject in a dose ranging from 10-80 micrograms. In another embodiment, a GH modified by CTPs is administered to a subject in a dose ranging from 20-60 micrograms. In another embodiment, a GH modified by CTPs is administered to a subject in a dose ranging from 10-50 micrograms. In another embodiment, a GH modified by CTPs is administered to a subject in a dose ranging from 40-80 micrograms. In another embodiment, a GH modified by CTPs is administered to a subject in a dose ranging from 10-30 micrograms. In another embodiment, a GH modified by CTPs is administered to a subject in a dose ranging from 30-60 micrograms.

In another embodiment, GH modified by CTPs is administered to a subject in a dose ranging from 0.2 mg to 2 mg. In another embodiment, a GH modified by CTPs is administered to a subject in a dose ranging from 2 mg to 6 mg. In another embodiment, a GH modified by CTPs is administered to a subject in a dose ranging from 4 mg to 10 mg. In another embodiment, a GH modified by CTPs is administered to a subject in a dose ranging from 5 mg and 15 mg.

In another embodiment, a GH modified by CTPs is injected into the muscle (intramuscular injection). In another embodiment, a GH modified by CTPs is injected below the skin (subcutaneous injection). In another embodiment, a GH modified by CTPs is injected into the muscle. In another embodiment, a GH modified by CTPs is injected below the skin.

In another embodiment, the methods of the invention include increasing the compliance in the use of GH therapy, comprising providing to a subject in need thereof, a GH modified by CTPs, thereby increasing compliance in the use of growth hormone therapy.

In another embodiment, protein drugs of molecular weight lower than 50,000 daltons, such as GH modified by CTPs of the present invention are in general short-lived species in vivo, having short circulatory half-lives of several hours. In another embodiment, the subcutaneous route of administration in general provides slower release into the circulation. In another embodiment, the CTP modified polypeptide of the invention prolongs the half-live of protein drugs of molecular weight lower than 50,000 daltons, such as GH. In another embodiment, the CTP modified polypeptide of the invention enable interferons to exert their beneficial effects for a longer period of time.

In another embodiment, the immunogenicity of a CTP modified polypeptide comprising a GH modified by CTPs is equal to an isolated GH. In another embodiment, the immunogenicity of a CTP modified polypeptide comprising a GH modified by CTPs is comparable to an isolated GH. In another embodiment, modifying a GH as described herein with CTP peptides reduces the immunogenicity of the GH. In another embodiment, the CTP modified polypeptide comprising a GH is as active as an isolated GH protein. In another embodiment, the CTP modified polypeptide comprising a GH is more active than an isolated GH. In another embodiment, the CTP modified polypeptide comprising a GH maximizes the growth hormone's protective ability against degradation while minimizing reductions in bioactivity.

In another embodiment, the methods of the invention include increasing the compliance of subjects afflicted with chronic illnesses that are in need of a GH therapy. In another embodiment, the methods of the invention enable reduction in the dosing frequency of a GH by modifying the GH with CTPs as described hereinabove. In another embodiment, the term compliance comprises adherence. In another embodiment, the methods of the invention include increasing the compliance of patients in need of a GH therapy by reducing the frequency of administration of the GH. In another embodiment, reduction in the frequency of administration of the GH is achieved due to the CTP modifications which render the CTP-modified GH more stable. In another embodiment, reduction in the frequency of administration of the GH is achieved as a result of increasing T1/2 of the growth hormone. In another embodiment, reduction in the frequency of administration of the GH is achieved as a result of increasing the clearance time of the GH. In another embodiment, reduction in the frequency of administration of the growth hormone is achieved as a result of increasing the AUC measure of the growth hormone.

In another embodiment, the present invention provides a method of decreasing body fat in a non-human subject, comprising administering to said subject a therapeutically effective amount of an expression vector comprising a polynucleotide, said polynucleotide consisting of a non-human growth hormone, one chorionic gonadotrophin carboxy terminal peptide (CTP) attached to the amino terminus of said non-human growth hormone, and two chorionic gonadotrophin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of increasing insulin-like growth factor (IGF-1) levels in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby increasing IGF-1 levels in said subject.

In another embodiment, the present invention provides a method of increasing insulin-like growth factor (IGF-1) levels in a non-human subject, comprising administering to said subject a therapeutically effective amount of an expression vector comprising a polynucleotide, said polynucleotide consisting of a non-human growth hormone, one chorionic gonadotrophin carboxy terminal peptide (CTP) attached to the amino terminus of said non-human growth hormone, and two chorionic gonadotrophin CTPs attached to the carboxy terminus of said non-human growth hormone, and wherein said polypeptide optionally consists of a signal peptide attached to the amino terminus of said one CTP, thereby inducing growth or weight gain in a non-human subject.

In one embodiment, increasing IGF-1 levels in a human subject may be effective in treating, preventing or suppressing type 1 diabetes, type 2 diabetes, amyotrophic lateral sclerosis (ALS aka "Lou Gehrig's Disease"), severe burn injury and myotonic muscular dystrophy (MMD).

In another embodiment, a GH modified by CTPs is administered to a subject once a day. In another embodiment, a polypeptide comprising a GH modified by CTPs is administered to a subject once every two days. In another embodiment, a GH modified by CTPs is administered to a subject once every three days. In another embodiment, a GH modified by CTPs is administered to a subject once every four days. In another embodiment, a GH modified by CTPs is administered to a subject once every five days. In another embodiment, a GH modified by CTPs is administered to a subject once every six days. In another embodiment, a GH modified by CTPs is administered to a subject once every week. In another embodiment, a GH modified by CTPs is administered to a subject once every 7-14 days. In another embodiment, a GH modified by CTPs is administered to a subject once every 10-20 days. In another embodiment, a GH modified by CTPs is administered to a subject once every 5-15 days. In another embodiment, a GH modified by CTPs is administered to a subject once every 15-30 days.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the growth hormone dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping orlyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compounds solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of an effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a GH modified by CTPs is administered via systemic administration. In another embodiment, a growth hormone as described herein is administered by intravenous, intramuscular or subcutaneous injection. In another embodiment, a GH modified by CTPs is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized GH modified by CTPs as described in sterile water for injection. In another embodiment, a pharmaceutical composition comprises a lyophilized growth hormone as described in sterile PBS for injection. In another embodiment, a pharmaceutical composition comprises a lyophilized growth hormone as described in sterile 0.9% NaCl for injection.

In another embodiment, the pharmaceutical composition comprising a GH modified by CTPs as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a growth hormone as described herein and lactobionic acid and an acetate/glycine buffer. In another embodiment, the pharmaceutical composition comprising a GH modified by CTPs as described herein and amino acids, such as arginine or glutamate that increase the solubility of interferon compositions in water. In another embodiment, the pharmaceutical composition comprises a lyophilized GH modified by CTPs as described herein and glycine or human serum albumin (HSA), a buffer (e g. acetate) and an isotonic agent (e.g NaCl). In another embodiment, the pharmaceutical composition comprises a lyophilized GH modified by CTPs as described herein and phosphate buffer, glycine and HSA.

In another embodiment, the pharmaceutical composition comprising a GH modified by CTPs as described herein is stabilized when placed in buffered solutions having a pH between about 4 and 7.2. In another embodiment, the pharmaceutical composition comprising a GH modified by CTPs as described herein is stabilized with an amino acid as a stabilizing agent and in some cases a salt (if the amino acid does not contain a charged side chain).

In another embodiment, the pharmaceutical composition comprising a GH modified by CTPs as described herein is a liquid composition comprising a stabilizing agent at between about 0.3% and 5% by weight which is an amino acid.

In another embodiment, the pharmaceutical composition comprising a GH modified by CTPs as described herein provides dosing accuracy and product safety. In another embodiment, the pharmaceutical composition comprising a GH modified by CTPs as described herein provides a biologically active, stable liquid formulation for use in injectable applications. In another embodiment, the pharmaceutical composition comprises a non-lyophilized GH modified by CTPs as described herein.

In another embodiment, the pharmaceutical composition comprising a GH modified by CTPs as described herein provides a liquid formulation permitting storage for a long period of time in a liquid state facilitating storage and shipping prior to administration.

In another embodiment, the pharmaceutical composition comprising a GH modified by CTPs as described herein comprises solid lipids as matrix material. In another embodiment, the injectable pharmaceutical composition comprising a GH modified by CTPs as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e. g. glycerides composed of fatty acids which are present in the emulsions for parenteral nutrition).

In another embodiment, the pharmaceutical composition comprising a GH modified by CTPs as described herein is in the form of liposomes (J. E. Diederichs and al., Pharm./nd. 56 (1994) 267-275).

In another embodiment, the pharmaceutical composition comprising a GH modified by CTPs as described herein comprises polymeric microparticles. In another embodiment, the injectable pharmaceutical composition comprising a GH modified by CTPs as described herein comprises polymeric microparticles. In another embodiment, the pharmaceutical composition comprising a GH modified by CTPs as described herein comprises nanoparticles. In another embodiment, the pharmaceutical composition comprising a GH modified by CTPs as described herein comprises liposomes. In another embodiment, the pharmaceutical composition comprising a GH modified by CTPs as described herein comprises lipid emulsion. In another embodiment, the pharmaceutical composition comprising a GH modified by CTPs as described herein comprises microspheres. In another embodiment, the pharmaceutical composition comprising a GH modified by CTPs as described herein comprises lipid nanoparticles. In another embodiment, the pharmaceutical composition comprising a GH modified by CTPs as described herein comprises lipid nanoparticles comprising amphiphilic lipids. In another embodiment, the pharmaceutical composition comprising a GH modified by CTPs as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the GH modified by CTPs of the present invention can be provided to the individual with additional active agents to achieve an improved therapeutic effect as compared to treatment with each agent by itself. In another embodiment, measures (e.g., dosing and selection of the complementary agent) are taken to minimize adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation of EPO Constructs

Materials and Methods:

Construction of expression vector pCI-dhfr: pCI-neo mammalian expression vector was purchased from Promega (Catalog No. E1841). The vector contains a CMV IE enhancer/promoter and neomycin phosphotransferase gene. The pSV2-dhfr clone was purchased from ATCC (Catalog No. 37146). The plasmid contains the murine dhfr gene. The construction of pCI-dhfr vector was performed as follows:
  a. The pSV2-dhfr plasmid was digested with restriction enzyme BglII (3' end of the dhfr gene). DNA polymerase I, Large (Klenow) Fragment was used to fill-in the 5' overhangs to form blunt ends. The DNA was then digested with restriction enzyme AvrII (5' end of the dhfr gene). The dhfr gene (AvrII-blunt end) fragment was isolated.
  b. The pCI-neo vector was digested with restriction enzyme BstXI (3' end of the neo gene). DNA polymerase I, Large (Klenow) Fragment was used to remove the 3' overhangs to form blunt ends. The DNA was then digested with restriction enzyme AvrII (5' end of the neo gene). The expression vector (AvrII-blunt end) was isolated.
  c. The dhfr gene was ligated into pCI vector to form an expression vector containing the dhfr gene (pCI-dhfr).

Construction of hEPO-CTP variants: A cassette gene containing the C-Terminal peptide (CTP) of the beta subunit of hCG was fused to the coding sequence of human EPO (NP_000790.2) at different locations. Four EPO-CTP variants were constructed as illustrated in FIGS. 1A-D. The proEPO signal peptide was used for the construction of the secreted EPO-CTP variants. XbaI-NotI fragments containing Epo sequences were ligated into the pCI-dhfr expression vector of the present invention.

Table 2 hereinbelow summarizes the primer sequences used for constructing the CTP-containing polypeptides of the present invention.

TABLE 2

| Primer number | SEQ ID NO | sequence | Restriction site (underlined in sequence) |
|---|---|---|---|
| 1 | 7 | 5' AA<u>TCTAGA</u>GGTCATCATGGGGGT GC 3' | XbaI |
| 2 | 8 | 5' ATT<u>GCGGCCGC</u>GGATCCAGAAGA CCTTTATTG 3' | NotI |
| 17$^R$ | 9 | 5' TA<u>AATATT</u>GGGGTGTCCGAGGGC CC 3' | SspI |
| 10 | 10 | 5' CC<u>AATATT</u>ACCACAAGCCCCACC ACGCCTCAT 3' | SspI |
| 11$^R$ | 11 | 5' T<u>GCGGCCGC</u>GGATCCTTATCTGT CCCCTGTCCTGC 3' | NotI |
| 15 | 12 | 5' GCCCTGCTGTCGGAAGC 3' | |
| 2$^R$ | 13 | 5' ATT<u>GCGGCCGC</u>GGATCCAGAAGA CCTTTATTG | NotI |
| 23$^R$ | 14 | 5' CTTTGAGGAAGAGGAGCCCAGGA CTGGGAGGC 3' | |
| 24 | 15 | 5' CCTGGGCTCCTCTTCCTCAAAGG C 3' | |
| 38$^R$ | 50 | 5' GCTTCCGACAGCAGGGC 3' | |

EPO-1 701-1-p17-6 (Epo-1—SEQ ID NO: 1): The XbaI-NotI 702 bp fragment was constructed by PCR using the above primers (SEQ ID NOs: 7-16). Then the XbaI-NotI PCR fragment containing Epo-ctp sequence was ligated into pCI-dhfr expression vector.

EPO-2 701-2-p24-2 (Epo-2—SEQ ID NO: 2): The XbaI/ApaI fragment (hGH-ctp) of pCI-dhfr-401-2-p21-2 (hGH-ctpx2) was replaced by the XbaI/ApaI fragment (EPO-ctp) of 701-1-p17-6 to create an Epo-ctpx2.

EPO-4-701-4-p42-1 (Epo-4—SEQ ID NO: 4): Firstly, a fragment from pCI-dhfr-EPO-ctp (701-1-p17-6) was constructed by PCR using primers 1 and 17 followed by XbaI/SspI digestion. This resulted in a fragment containing EPO and partial 5' CTP.

Secondly, a new fragment was constructed by overlapping PCR, on pGT123-hEpo as a template, using primer 10 and primer 11. SspI/NotI digestion resulted in a fragment containing 3' partial CTP and Epo.

The two fragments were ligated into pCI-dhfr to construct the p701-4-p42-1 clone.

EPO-3-p56-6 (Epo-3 SEQ ID NO: 3): Primers were purchased from Sigma-Genosys. PCR reaction was performed using primer 15 (SEQ ID NO: 12) and primer 2$^R$ (SEQ ID NO: 13) and plasmid DNA of pCI-dhfr-EPO-ctp x2 (701-2-p24-2) as a template. As a result of the PCR amplification, a 486 bp product was formed and ligated into a TA cloning vector (Invitrogen, catalog K2000-01). Stu I-NotI fragment containing *Epo-ctp x2 sequence was isolated (209 bp).

Three sequential PCR reactions were performed. The first reaction was conducted with primer 1 (SEQ ID NO: 7) and primer 23$^R$ (SEQ ID NO: 14) and plasmid DNA of pGT123-epo-ctp as a template; as a result of the PCR amplification, an 80 bp product was formed (signal peptide).

The second reaction was conducted with primer 24 (SEQ ID NO: 15) and primer 11$^R$ (SEQ ID NO: 11) and plasmid DNA of 701-4-p42-1 as a template; as a result of the PCR amplification, a 610 bp product was formed.

The last reaction was conducted with primers 1 (SEQ ID NO: 7) and 11$^R$ (SEQ ID NO: 11) and a mixture of the products of the previous two reactions as a template; as a result of the PCR amplification, a 700 bp product was formed and the XbaI-StuI fragment was isolated.

The two fragments (XbaI-StuI and StuI-NotI) were inserted into the eukaryotic expression vector pCI-dhfr (triple ligation) to yield the 701-3-p56-6 clone.

EPO-5-p91-4 (Epo-5 SEQ ID NO: 5—(ctp-Epo): Primers were ordered from Sigma-Genosys. A PCR reaction was performed using primer 1 (SEQ ID NO: 7) and primer 11$^R$ (SEQ ID NO: 11) and plasmid DNA of pCI-dhfr-ctp-EPO-ctp x2 (701-3-p56-6) as a template; as a result of the PCR amplification, a 670 bp product was formed and ligated into TA cloning vector (Invitrogen, catalog K2000-01). XbaI-NotI fragment containing ctp-Epo sequence was ligated into our eukaryotic expression vector pCI-dhfr to yield the 701-5-p91-4 clone.

EPO-6-p90-1 (Epo-6 SEQ ID NO: 6—(ctp-Epo-ctp): Three PCR reactions were performed. The first reaction was conducted with primer 1 (SEQ ID NO: 7) and primer 38$^R$ (SEQ ID NO: 50) and plasmid DNA of 701-3-p56-6 as a template; as a result of the PCR amplification, a 400 bp product was formed.

The second reaction was conducted with primer 15 (SEQ ID NO: 12) and primer 2$^R$ (SEQ ID NO: 13) and plasmid DNA of 701-1-p17-6 as a template; as a result of the PCR amplification, a 390 bp product was formed.

The last reaction was conducted with primers 1 (SEQ ID NO: 7) and 2$^R$ (SEQ ID NO: 13) and a mixture of the products of the previous two reactions as a template; as a result of the PCR amplification, a 787 bp product was formed and ligated into TA cloning vector (Invitrogen, catalog K2000-01). The XbaI-NotI fragment containing ctp-Epo-ctp sequence was ligated into the eukaryotic expression vector pCI-dhfr to yield the 701-6-p90-1 clone.

Example 2

Expression and Isolation of EPO-CTP Polypeptides

Materials and Methods

DNA transfection and clone selection: DG44 cells were transfected with pCI-DHFR expression vectors containing EPO-CTP variants using FuGENE6 Reagent (FuGENE Transfection Reagent—Roche Cat. 11 815 091 001). 48 hr following transfection, cells were diluted and seeded at 50-200 cells per well in a selective medium (CD DG44 Medium w/o HT (Gibco: Scotland part: #07990111A) Sku num.:ME060027 supplemented with 8 mM L-Glutamine Biological Industries: Cat: 03-020-1A) and 18 mL/L of 10% Pluronic F-68 solution (Gibco: Cat: 240040-032). Selected clones were screened for highest protein production using commercial ELISA. Three to five producing clones per each variant were frozen for a backup cell bank. A selected clone for each variant was adapted to growth in larger scale cultures up to 1 L flasks on an orbital shaker platform. Supernatants were collected and analyzed by ELISA, SDS-PAGE and Western blot. Following the withdrawal of aliquots, the protein-containing supernatants were kept frozen until further use.

Cell culture: DG44 cells were maintained in DG44 medium with HT (cat#12610-010, Gibco) supplemented with 8 mM L-Glutamine (Biological Industries: Cat: 03-020-1A) and 18 mL/L of 10% Pluronic F-68 solution (Gibco: Cat: 240040-032), at 37° C. in humidified 8% $CO_2$ incubator. Transfected clones were maintained in DG44 basal medium without HT supplement, hypoxanthine and thymidine, with pluronic acid and L-glutamine.

Sample preparation: Supernatants were collected, filtrated and analyzed by ELISA to determine protein concentration. SDS-PAGE and Western blot were used to determine purity and identity. Following ELISA, sample concentrations were defined and the solution was dialyzed against PBS. Following the withdrawal of aliquots, the protein-contained supernatants were kept frozen at −20° C. until further use.

Western blotting: Samples were electrophoresed on non-denaturing 15% SDS-polyacrylamide gels. Gels were allowed to equilibrate for 10 min in 25 mM Tris and 192 mM glycine in 20% (vol/vol) methanol. Proteins were transferred to a 0.2 μm pore size nitrocellulose membrane (Sigma, Saint Louis, Mo.) at 250 mA for 3 h, using a Mini Trans-Blot electrophoresis cell (Biorad Laboratories, Richmond, Calif.). The nitrocellulose membrane was incubated in 5% non-fat dry milk for 2 h at room temperature. The membrane was incubated with EPO anti-serum (1:1000 titer) overnight at 4° C. followed by three consecutive washes in PBS containing 0.1% Tween (10 min/wash). The membrane was incubated with secondary antibody conjugated to Horse Radish Peroxidase (HRP) (Zymed, San Francisco, Calif.) for 2 h at room temperature, followed by three washes. Finally, the nitrocellulose paper was reacted with enhanced chemiluminescent substrate (ECL) (Pierce, Rockford, Ill.) for 5 min, dried with a Whatman sheet, and exposed to X-ray film.

Results

Table 3 hereinbelow shows the concentrations of the various CTP-modified EPO forms obtained from 5 selected clones and their preparation for further testing.

TABLE 3

| #Version | # Clone | Stock Titer IU/ml[1] | Post dilution in Mock sup. according to Epo3 titer IU/ml[2] | Post ultra-filtration IU/ml[3] |
| --- | --- | --- | --- | --- |
| Epo0 SEQ ID NO: 16 | 17 | 3093 | 102 | 335 |
| Epo1 SEQ ID NO: 1 | 47 | 1049 | 104 | 291 |
| Epo2 SEQ ID NO: 2 | 67 | 2160 | 110 | 303 |
| Epo3 SEQ ID NO: 3 | 85 | 105 | 119 | 392 |
| Epo4 SEQ ID NO: 4 | 112 | 6100 | ND | 342 |

1. EPO variants stock concentration were determined by ELISA (Quantikine IVD Epo ELISA, DEPOO, R&D Systems)
2. Samples EPO-0, 1, 2 and 4 were diluted to 105 IU/ml in mock sup (Adjusted to Epo3 titer). Epo0=wild type EPO expressed in the same system as the CTP-modified EPOs.
3. All samples were concentrated and dialyzed by ultrafiltration against PBS to a final concentration of 180 IU/ml. All proteins were detected by Western blot as illustrated in FIG. 2.

Example 3

Biological Activity of the EPO-CTP Polypeptides of the Present Invention

The TF-1 bioactivity test represents the ability of the EPO-CTP variants to bind its receptor and then stimulate activity which results in cell proliferation. Therefore, this test was used as a first step in evaluating the biological potency of the EPO-CTP polypeptides of the present invention.

Materials and Methods

Cell Proliferation Analysis: Proliferation assay was performed with the cell line TF-1, measuring levels of MTT cellular stain as a function of EPO activity (Kitamura et al., Kitamura, T. et al. (1989) *Establishment and characterization of a unique human cell line that proliferates;* Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996). Exponentially growing TF-1 cells were washed twice, plated at about $10^4$ cells/well in microtiter plates, and incubated in basal medium with a titrated dilution series of EPO (Recormon®), EPO standard (NIBSC standard), rhEPO (MOD-7010), MOD-701 variants (EPO-1, EPO-2, EPO-3 and EPO-4) for 48 hours. 4 hours prior to assaying for cell proliferation, MTT reagent was added to the wells, and absorbance was measured by ELISA reader. A calculated protein concentration value for each variant protein was obtained from Eprex's (Epoetin (EPO)-man-made form of the human hormone) dose-response standard curve.

Results

The in vitro biological activity of EPO polypeptides was determined with an Epo-dependent cell line, human erythroleukemia TF-1 (DSMZ Cell Bank) [Dong et al., Biochemical and Biophysical Research Communications, Volume 339, Issue 1, 6 Jan. 2006, Pages 380-385]. The MTT assay was performed [Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996);], and the laboratory standard of EPO used to generate the standard curve was calibrated against the International Standard (Epo ampoule code 87/684 of NIBSC).

The results are summarized in Table 4 hereinbelow. The results indicate that the highest potency was achieved by using EPO 3 and EPO 0 in both 2 and 0.5 IU/ml concentrations.

TABLE 4

| | TF-1 Bioactivity IU/ml | | | | | | |
| --- | --- | --- | --- | --- | --- | --- | --- |
| Eprex STD IU/ml | EPO 0 SEQ ID NO: 16 | EPO 1 SEQ ID NO: 1 | EPO 2 SEQ ID NO: 2 | EPO 3 SEQ ID NO: 3 | EPO 4 SEQ ID NO: 4 | Recormon ® | EPO st |
| 2 | 4.93 | 2.32 | 2.13 | 6.91 | 3.55 | 3.44 | 7.40 |
| 0.5 | 1.60 | 0.76 | 0.53 | 1.34 | 0.84 | 0.87 | 1.53 |

Conclusion

As summarized in Table 4 hereinabove, different levels of potency were exerted by EPO-CTP polypeptides, indicating differences in receptor binding. EPO-CTP polypeptides differ by the number of CTP cassettes and the location to which they are fused. EPO-1 and EPO-2 contain 1 CTP sequence or 2 CTP sequences at the C-terminal of EPO, while EPO-3 contains 1 CTP at N-terminal and 2 CTP sequences at C-terminal EPO-4 is a dimer of two EPO molecules linked by CTP sequence. EPO-3 demonstrated potency level quite similar to WT-EPO, while EPO-1 and EPO-4 were about 50% less potent than WT-EPO, and EPO-2 potency was even less than 50%.

Example 4

Evaluation of the EPO-CTP Polypeptides of the Present Invention in a Mouse Model The following experiment was performed in order to compare the bio-activity of the EPO-CTP polypeptides of the present invention and commercial EPO Materials and Methods Animals:

Species/Strain: ICR or CD-1 Mice of either sex about 20-25 g

Group Size: n=7

No. Groups: 9

Total No. Animals: n=63

Experimental design of the study: The experiment was set up as summarized in Table 5 hereinbelow.

TABLE 5

| Group No. | No. Mice per Group | TREATMENT Compound | Dosing Dose Level | Regimen |
|---|---|---|---|---|
| 1 | n = 7 | Vehicle (Control) | 0 | 1x weekly |
| 2 | | MOCK | | |
| 3 | | MOD-7010 | 15 µg/kg | |
| 4 | | MOD-7011 | | |
| 5 | | MOD-7012 | | |
| 6 | | MOD-7013 | | |
| 7 | | MOD-7014 | | |
| 8 | | Commercial rhEPO | 15 µg/kg | |
| 9 | | | 5 µg/kg | 3 x weekly |

Animal treatment: All animals were administered with either control or the test EPO polypeptides of the present invention by bolus injection. The injection volume did not exceed 10 ml/kg. The length of the experiment was 22 days. A morbidity and mortality check was performed daily.

Reticulocyte count and hematocrit (hct) examination: Reticulocyte count was carried out in all test animals at day 2 and 14 hrs following the 1st respective vehicle or treatment injection. HCT was determined in all animals once prior to initial treatment ("0" Baseline control) and at 24 hrs after the 1st respective vehicle or treatment injection, and thereafter twice weekly until study termination (Day-22).

Results

Figure 4:
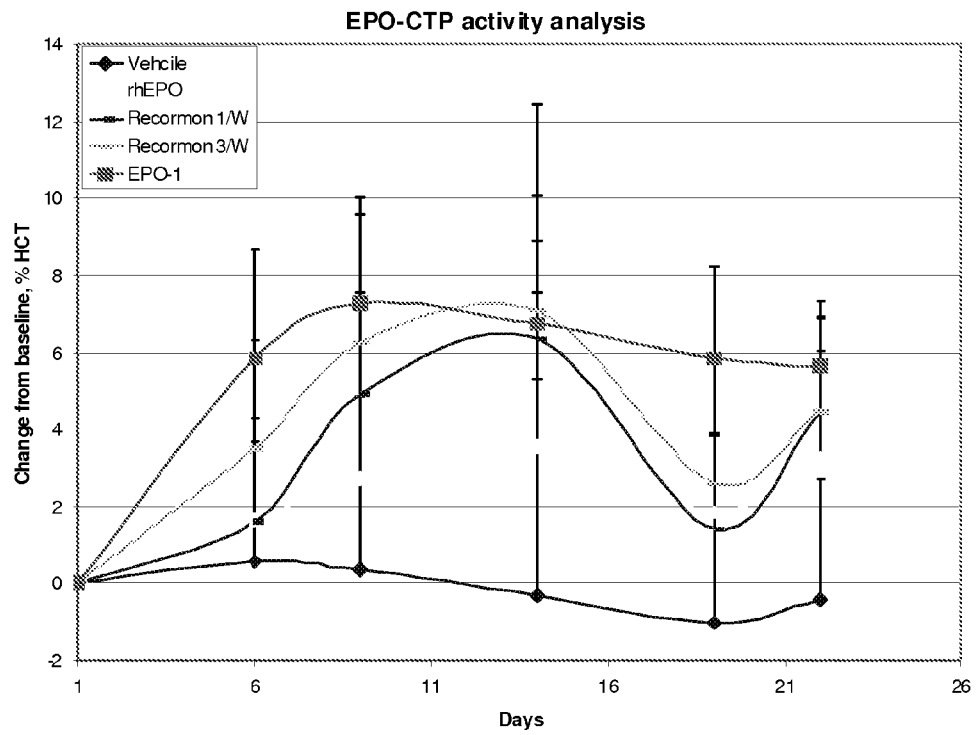
FIG. 4 is a graph illustrating the in vivo bioactivity of recombinant hEPO derivatives and EPO-1 (SEQ ID NO: 1). ICR mice (n=7/group) received a single i.v. injection/week (15 µg/kg) for three weeks of EPO-1, rhEPO-WT (SEQ ID NO: 16), Recormon® or Recormon® (5 µg/kg) 3 times a week. Control animals were injected i.v. with PBS. Blood samples were collected three times a week and haematocrit levels were detected. Each point represents the group average of haematocrit (%) ±SE.
Figure 5:
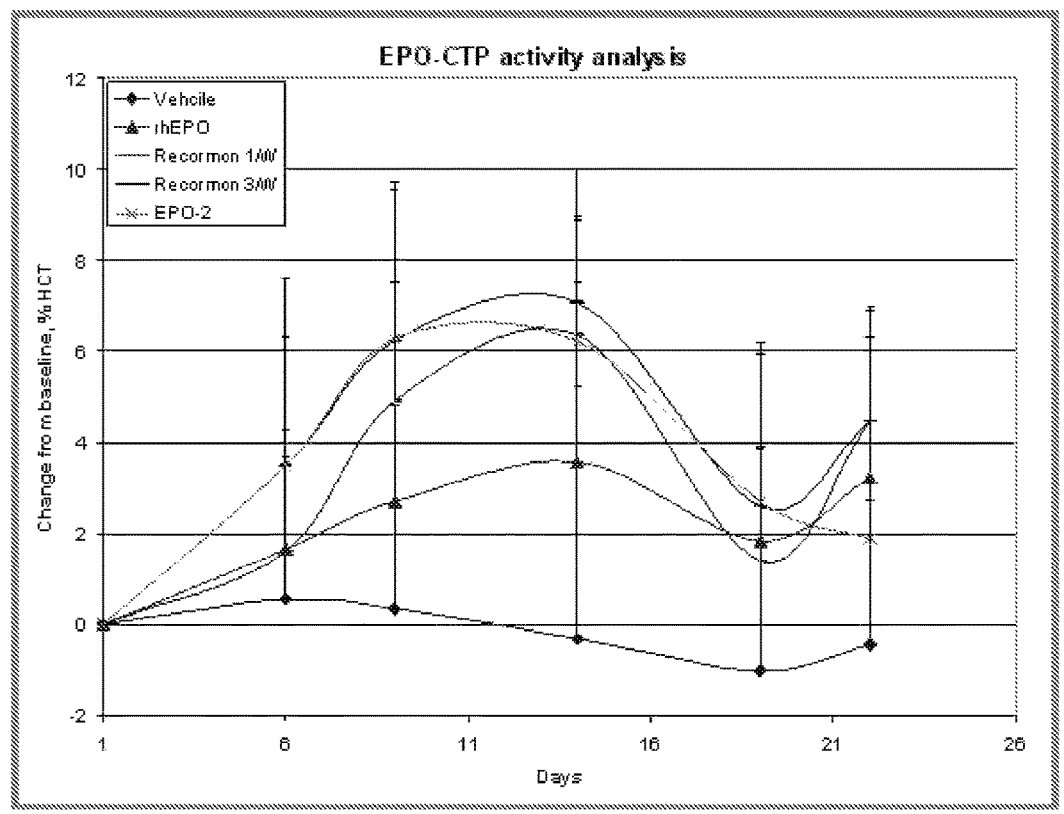
FIG. 5 is a graph illustrating the in vivo bioactivity of recombinant hEPO derivatives and EPO-2 (SEQ ID NO: 2). ICR mice (n=7/group) received a single i.v. injection/week (15 µg/kg) for three weeks of EPO-2 (SEQ ID NO: 2), rhEPO-WT (SEQ ID NO: 16), Recormon® or Recormon® (5 µg/kg) 3 times a week. Control animals were injected i.v. with PBS. Blood samples were collected three times a week and haematocrit levels were detected. Each point represents the group average of haematocrit (%) ±SE.
Figure 6:
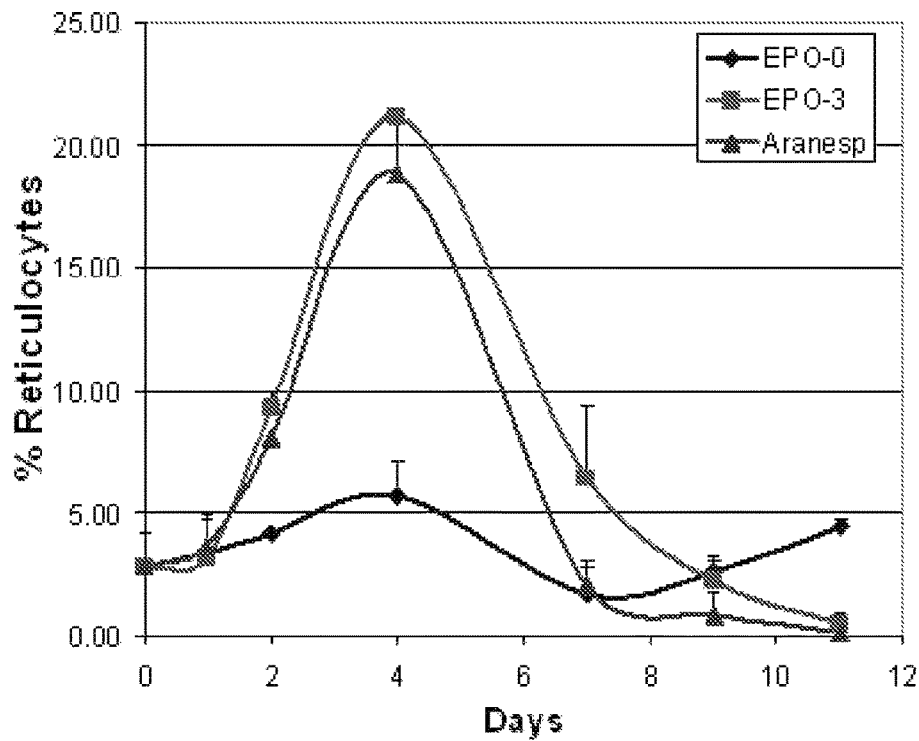
FIG. 6 is a time graph illustrating the change in reticulocyte level following a single bolus dose of EP0-0 (SEQ ID NO: 16), EPO-3 (SEQ ID NO: 3) and Aranesp®.
Figure 7:
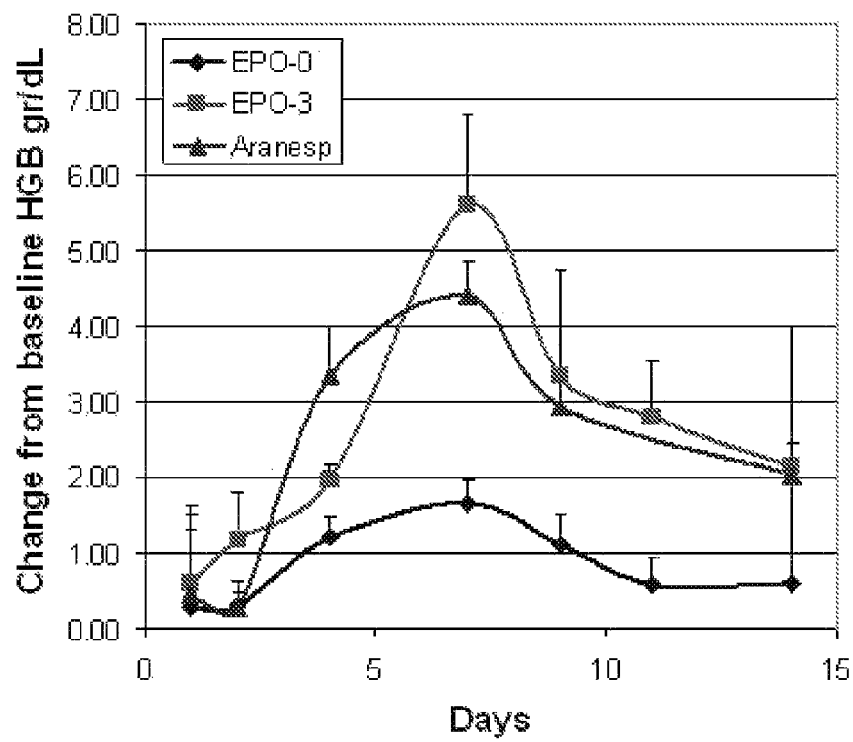
FIG. 7 is a time graph illustrating the change in hemoglobin level (presented as change from baseline) following a single bolus dose of EP0-0 (SEQ ID NO: 16), EPO-3 (SEQ ID NO: 3) and Aranesp®.
Figure 8:
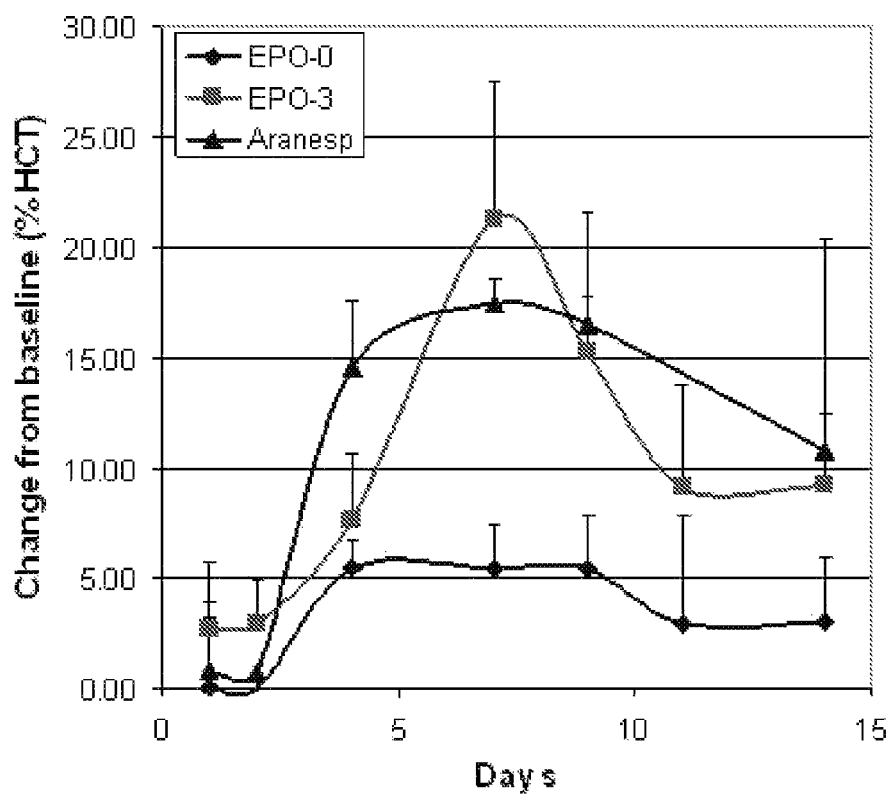
FIG. 8 is a time graph illustrating the change in hematocrit level following a single bolus dose of EP0-0 (SEQ ID NO: 16), EPO-3 (SEQ ID NO: 3) and Aranesp®.

The hematocrit results which are illustrated in FIGS. 3-5 show that EPO 3 has the highest hematocrit percentage change from baseline compared to EPO 1, EPO 2, Recormon® 1, Recormon® 3, rhEPO, and vehicle. The results demonstrating the percentage of reticulocytes in mice treated with the EPO-CTP polypeptides are summarized in Table 6 hereinbelow. These results show that EPO-3 is the most potent stimulator of erythropoiesis.

TABLE 6

| | % reticulocytes | |
|---|---|---|
| Days | 2 | 14 |
| Control | 3.72 | 3.46 |
| | 1.08 | 0.8 |
| Mock | 3.5 | 3.64 |
| | 0.6 | 1.13 |
| 7010 SEQ ID NO: 16 | 3.5 | 3.9 |
| | 0.6 | 1.54 |
| 7011 SEQ ID NO: 1 | 3.52 | 1.94 |
| | 1.38 | 1.08 |
| 7012 SEQ ID NO: 2 | 3.82 | 3.0 |
| | 1.02 | 0.88 |
| 7013 SEQ ID NO: 3 | 2.66 | 5.20 |
| | 0.97 | 2.96 |
| 7014 SEQ ID NO: 4 | 3.48 | 3.82 |
| | 0.71 | 0.90 |
| Recormon ® 1/W | 3.23 | 3.27 |
| | 0.73 | 0.59 |
| Recormon ® 3/w | 4.13 | 4.24 |
| | 1.21 | 1.14 |

Conclusion

The in vivo experiment was designed to measure two parameters; the first was to measure erythropoiesis parameters such as percentage of reticulocytes and increase of hemoglobin, RBC and hematocrit levels. The second was to measure the durability of the biological activity of each variant by injecting once weekly doses.

A superior performance of EPO-3 in its ability to stimulate erythropoiesis was observed in normal mice.

Example 5

Comparison of the EPO-CTP Polypeptides of the Present Invention to Aranesp®

The following experiment was performed in order to compare the biological activity of a single bolus dose of some EPO-CTP polypeptides of the present invention, commercial EPO and Aranesp®. Aranesp® is a commercial long-acting recombinant erythropoietin in which two site mutations were introduced, resulting in two additional N-glycosylation sites and an increase in the number of incorporated sialic acid residues.

Materials and Methods

Animals:

Species/Strain: Female CD-1 Mice of either sex about 20-25 g

Group Size: n=3

Experimental design of the study: The experiment was set up as summarized in Table 7 hereinbelow.

TABLE 7

| Group # | Test Article | animals/ group/ time-point | Dose Solution Conc. (μg/mL) | Dose Volume (mL/kg) | Time-Points * (hours post-administration) |
|---|---|---|---|---|---|
| 1 | MOD-7010 | 3 | 1.5 | 10 | 0 (Pre-dose), 0.25, 0.5, 1, 2, 6, 24, 48, 96, 168, 216, 264 and 336 hr post-dose administration |
| 2 | MOD-7013 SEQ ID NO: 3 | 3 | 1.5 | 10 | 0.25, 0.5, 1, 2, 6, 24, 48, 96, 168, 216, 264 and 336 hr post-dose administration |
| 3 | Aranesp ® | 3 | 1.5 | 10 | 0.25, 0.5, 1, 2, 6, 24, 48, 96, 168, 216, 264 and 336 hr post-dose administration |

Animal treatment: All animals were administered with either control or the test EPO polypeptides of the present invention by bolus injection. The injection volume did not exceed 10 ml/kg. The length of the experiment was 14 days. A morbidity and mortality check was performed daily.

Reticulocyte count and hematocrit (hct) examination: Reticulocyte count and hematocrit examination were performed as described above.

Results

The results are illustrated in FIGS. 6-9. Following a single I.V. injection of 15 μg/kg of EPO 3, all three blood parameters associated with erythropoietin i.e. number of reticulocytes, hemoglobin level and hematocrit, were improved relative to those obtained with similar injected dose of rhEPO or Aranesp®.

Example 6

Comparison of the Pharmacokinetics of EPO-CTP Polypeptides of the Present Invention to Aranesp®

The following experiment was performed in order to compare the pharmacokinetics of EPO-CTP polypeptide of the present invention, commercial EPO and Aranesp®.

Materials and Methods

Serum samples were analyzed in order to determine specific concentration levels for each sample. Concentration and time-point data were processed using WinNonLin non-compartmental analysis. Parameters determined included: AUC, CL, Ke, $T_{1/2}$, Cmax, Tmax, and Vdz.

Serum concentrations were determined using two ELISA kits in parallel. EPO-3 serum concentration was measured using StemCell ELISA kit in comparison to EPO-0 and Aranesp® serum concentration which were determined using R&D system ELISA kit.

Results

The results of the pharmacokinetic analysis are summarized in Table 8, hereinbelow. These results show that EPO 3 exhibited favorable pharmacokinetic measures as indicated for example in AUC measures, t1/2, and Cmax. Tmax measures were equal to EPO-0, EPO-3, and Aranesp®.

TABLE 8

| Parameters | Units | EPO-0 | EPO-3 | Aranesp ® |
|---|---|---|---|---|
| AUClast | hr*mIU/mL | 31739 | 306072 | 178661 |
| CL^ | mL/hr/kg | 1.1152 | 0.2188 | 0.1207 |
| Ke | 1/hr | 0.157 | 0.0529 | 0.0639 |
| t½ | hr | 4.4139 | 13.1141 | 10.84 |
| Cmax | mIU/mL | 10766 | 16466 | 13266 |

TABLE 8-continued

| Parameters | Units | EPO-0 | EPO-3 | Aranesp ® |
|---|---|---|---|---|
| Tmax | Hr | 0.25 | 0.25 | 0.25 |
| Vdz | mL/kg | 7.1017 | 4.1394 | 1.8877 |

Figure 9:
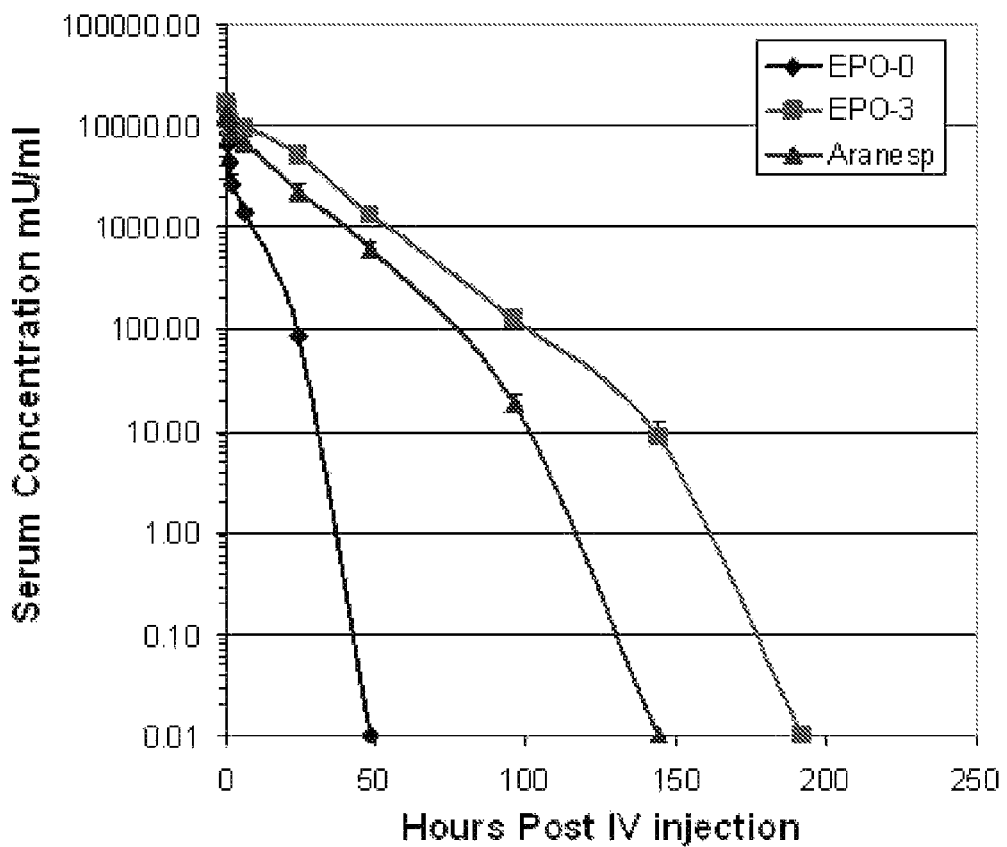
FIG. 9 is a graph illustrating the change in serum concentration of EPO-0 (SEQ ID NO: 16), EPO-3 (SEQ ID NO: 3) and Aranesp® post i.v. injection.

The results of the serum concentration analysis are illustrated in FIG. 9. These results show that EPO-3 was still detectable in the serum after about 190 hours. Both EPO-0 and Aranesp® were not detectable in the serum after about 140 hours and 50 hours, respectively.

Conclusion

Clearance of EPO-3 (MOD-7013) from the blood of CD-1 mice was significantly slower than that for rhEPO or Aranesp®. The corresponding calculated half-life times were: rhEPO—4.41 h; Aranesp®—0.84 h; and MOD-7013—13.11 h.

Example 7

Generation of hGH Constructs

Materials and Methods

Four hGH clones (variants of 20 kD protein) were synthesized. XbaI-Not I fragments containing hGH sequences from the four variants were ligated into the eukaryotic expression vector pCI-dhfr previously digested with XbaI-NotI. DNA from the 4 clones (401-0, 1, 2, 3 and 4) was prepared. Another partial hGH clone (1-242 bp) from 22 kD protein was also synthesized (0606114). Primers were ordered from Sigma-Genosys. The primer sequences used to generate the hGH-CTP polypeptides of the present invention are summarized in Table 9 hereinbelow.

TABLE 9

| Primer number | SEQ ID NO | sequence | Restriction site (underlined in sequence) |
|---|---|---|---|
| 25 | 27 | 5' CTCTAGAGGACATGGCCAC 3' | XbaI |
| 32^R | 28 | 5' ACAGGGAGGTCTGGGGGTTCTG CA 3' | |
| 33 | 29 | 5' TGCAGAACCCCCAGACCTCCCT GTGC 3' | |
| 4^R | 30 | 5' CCAAACTCATCAATGTATCTTA 3' | |
| 25 | 31 | 5' CTCTAGAGGACATGGCCAC 3' | XbaI |

TABLE 9-continued

| Primer number | SEQ ID NO | sequence | Restriction site (underlined in sequence) |
|---|---|---|---|
| 35$^R$ | 32 | 5' CGAACTCCTGGTAGGTGTCAAA GGC 3' | |
| 34 | 33 | 5' GCCTTTGACACCTACCAGGAGT TCG 3' | |
| 37$^R$ | 34 | 5' ACGCGGCCGCATCCAGACCTTC ATCACTGAGGC 3' | NotI |
| 39$^R$ | 35 | 5' GCGGCCGCGGACTCATCAGAAG CCGCAGCTGCCC 3' | |

Construction of 402-0-p69-1 (hGH) SEQ ID NO: 36: MOD-4020 is the wild type recombinant human growth hormone (without CTP) which was prepared for use as control in the below described experiments.

Three PCR reactions were performed. The first reaction was conducted with primer 25 and primer 32$^R$ and plasmid DNA of 0606114 (partial clone of hGH 1-242 bp) as a template; as a result of the PCR amplification, a 245 bp product was formed.

The second reaction was conducted with primer 33 and primer 4$^R$ and plasmid DNA of 401-0-p57-2 as a template; as a result of the PCR amplification, a 542 bp product was formed.

The last reaction was conducted with primers 25 and 4$^R$ and a mixture of the products of the previous two reactions as a template; as a result of the PCR amplification, a 705 bp product was formed and ligated into the TA cloning vector (Invitrogen, catalog K2000-01). The XbaI-NotI fragment containing hGH-0 sequence was ligated into the eukaryotic expression vector pCI-dhfr. The vector was transfected into DG-44 CHO cells. Cells were grown in protein-free medium.

Construction of 402-1-p83-5 (hGH-CTP)—SEQ ID NO: 37 and 402-2-p72-3 (hGH-CTPx2)—SEQ ID NO: 38: MOD-4021 is a recombinant human growth hormone which was fused to 1 copy of the C-terminal peptide of the beta chain of human Chorionic Gonadotropin (CTP). The CTP cassette of MOD-4021 was attached to the C-terminus (one cassette). MOD-4022 is a recombinant human growth hormone which was fused to 2 copies of the C-terminal peptide of the beta chain of human Chorionic Gonadotropin (CTP). The two CTP cassettes of MOD-4022 were attached to the C-terminus (two cassettes).

Construction of hGH-CTP and hGH-CTP-CTP was performed in the same way as the construction of hGH-0. pCI-dhfr-401-1-p20-1 (hGH*-ctp) and pCI-dhfr-401-2-p21-2 (hGH*-ctp x2) were used as templates in the second PCR reaction.

Figure 10:
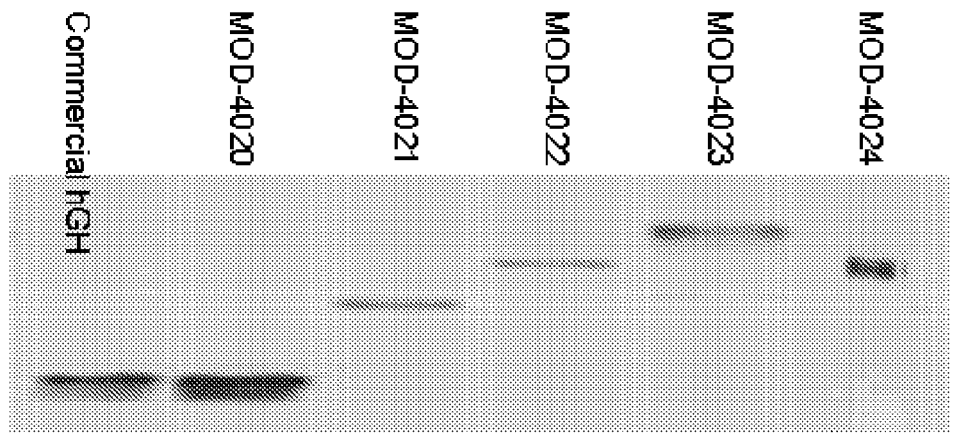
FIG. 10 is a Western blot illustrating the molecular weight & identity of MOD-4020 (SEQ ID NO: 36), MOD-4021 (SEQ ID NO: 37), MOD-4022 (SEQ ID NO: 38), MOD-4023 (SEQ ID NO: 39) and MOD-4024 (SEQ ID NO: 40). A pAGE SDS gel was blotted and stained using monoclonal anti-hGH antibodies. The photograph indicates that like commercial and wild type hGH, MOD-7020-4 variants are recognized by anti-hGH antibodies.

MOD-4021 and MOD-4022 were expressed in DG-44 CHO cells. Cells were grown in protein-free medium. The molecular weight of MOD-4021 is ~30.5 Kd since hGH has a MW of 22 Kd while each "CTP cassette" contributes 8.5 Kd to the overall molecular weight (see FIG. 10). The molecular weight of MOD-4022 is ~39 Kd (see FIG. 10).

Construction of 402-3-p81-4 (CTP-hGH-CTP-CTP)—SEQ ID NO: 39 and 402-4-p82-9 (CTP*hGH-CTP-CTP)—SEQ ID NO: 40: MOD-4023 is a recombinant human growth hormone which was fused to 3 copies of the C-terminal peptide of the beta chain of human Chorionic Gonadotropin (CTP). The three CTP cassettes of MOD-4023 were attached to both N-terminus (one cassette) and the C-terminus (two cassettes). MOD-4024 is a recombinant human growth hormone which is fused to 1 truncated and 2 complete copies of the C-terminal peptide of the beta chain of human Chorionic Gonadotropin (CTP). The truncated CTP cassette of MOD-4024 was attached to the N-terminus and two CTP cassettes were attached to the C-terminus (two cassettes).

Three PCR reactions were performed. The first reaction was conducted with primer 25 and primer 35$^R$ and plasmid DNA of p401-3-p12-5 or 401-4-p22-1 as a template; as a result of the PCR amplification, a 265 or 220 bp product was formed. The second reaction was conducted with primer 34 and primer 37$^R$ and plasmid DNA of TA-hGH-2-q65-1 as a template; as a result of the PCR amplification, a 695 bp product was formed. The last reaction was conducted with primers 25 and 37$^R$ and a mixture of the products of the previous two reactions as a template; as a result of the PCR amplification, a 938 or 891 bp product was formed and ligated into TA cloning vector (Invitrogen, catalog K2000-01). Xba I-Not I fragment containing hGH sequence was ligated into our eukaryotic expression vector pCI-dhfr.

MOD-4023 and MOD-4024 were expressed in DG-44 CHO cells. Cells were grown in protein-free medium. The molecular weight of MOD-4023 is ~47.5 Kd (see FIG. 10) and the molecular weight of MOD-4024 is ~43.25 Kd (see FIG. 10).

Construction of 402-6-p95a-8 (CTP-hGH-CTP)—SEQ ID NO: 41: Construction of hGH-6 was performed in the same way as the construction of hGH-3. pCI-dhfr-402-1-p83-5 (hGH-ctp) was used as a template in the second PCR reaction.

Construction of 402-5-p96-4 (CTP-hGH)—SEQ ID NO: 42: PCR reaction was performed using primer 25 and primer 39$^R$ and plasmid DNA of pCI-dhfr-ctp-EPO-ctp (402-6-p95a-8) as a template; as a result of the PCR amplification, a 763 bp product was formed and ligated into TA cloning vector (Invitrogen, catalog K2000-01). Xba I-Not I fragment containing ctp-hGH sequence was ligated into our eukaryotic expression vector pCI-dhfr to yield 402-5-p96-4 clone.

Example 8

In Vivo Bioactivity Tests of hGH-CTP Polypeptides of the Present Invention

The following experiment was performed in order to test the potential long acting biological activity of hGH-CTP polypeptides in comparison with commercial recombinant human GH and MOD-4020.

Materials and Methods

Female hypophysectomized rats (60-100 g) received a weekly S.C. injection of 21.7 µg hGH-CTP polypeptides or a once daily 5 µg S.C. injection of control commercial rhGH.

Weight was measured in all animals before treatment, 24 hours following first injection and then every other day until the end of the study on day 21. Each point represents the group's average weight gain percentage ((Weight day 0-weight last day)/Weight day 0). Average weight gain was normalized against once-daily injection of commercial hGH. The treatment schedule is summarized in Table 10.

TABLE 10

| No. | Drug | N | Route | Treatment Schedule | Equimolar Dose (μg/rat) | Accumulate Dosage (μg/rat) | Dose Vol. (ml) |
|---|---|---|---|---|---|---|---|
| 1 | Vehicle | 7 | s.c. | days 1, 7 and 13; 1/W | NA | NA | 0.25 |
| 2 | Mock | 7 | s.c | days 1, 7 and 13; 1/W | NA | NA | 0.25 |
| 3 | MOD-4020 SEQ ID NO: 36 | 7 | s.c | days 1, 7 and 13; 1/W | 21.7 | 65 | 0.25 |
| 4 | MOD-4021 SEQ ID NO: 37 | 7 | s.c. | days 1, 7 and 13; 1/W | 21.7 | 65 | 0.25 |
| 5 | MOD-4022 SEQ ID NO: 38 | 7 | s.c. | days 1, 7 and 13; 1/W | 21.7 | 65 | 0.25 |
| 6 | MOD-4023 SEQ ID NO: 39 | 7 | s.c. | days 1, 7 and 13; 1/W | 21.7 | 65 | 0.25 |
| 7 | MOD-4024 SEQ ID NO: 40 | 7 | s.c. | days 1, 7 and 13; 1/W | 21.7 | 65 | 0.25 |
| 8 | Commercial hGH v.1 | 7 | s.c. | days 1, 7 and 13; 1/W | 21.7 | 65 | 0.25 |
| 9 | Commercial hGH v.1 | 7 | s.c. | days 1-13; d/W | 5 | 65 | 0.25 |

Results

Results are summarized in FIG. 11. These results show that MOD-4023 (SEQ ID NO: 39) and MOD-4024 (SEQ ID NO: 40) induced over 120% weight gain compared to commercial rhGH which induced 100% weight gain.

Conclusion

Three weekly doses (Days of injections; 1, 7, and 13) of 21.7 μg of MOD-4023 (SEQ ID NO: 39) and MOD-4024 (SEQ ID NO: 40) induced a 30% greater weight increase in hypophysectomised rats compared to commercial rhGH injected at the same accumulated dose which was administered once per day at a dose of 5 μg for 13 days.

Example 9

Pharmacokinetic Studies of CTP-Modified GH

Single-dose pharmacokinetic studies were conducted in Sprague-Dawley rats. All animal experimentation was conducted in accordance with the Animal Welfare Act, the Guide for the Care and Use of Laboratory Animals, and under the supervision and approval of the Institutional Animal Care and Use Committees of Modigene, Biotechnology General Ltd. Rats were housed either individually or two per cage in rooms with a 12-h light/dark cycle. Access to water (municipal supply) and noncertified rodent chow was provided ad libitum.

To compare the pharmacokinetics of CTP-hGH-CTP-CTP and GH in rats, four groups of Sprague-Dawley rats (270-290 g), three to six male rats per group. The rats were randomly assigned to four treatment groups (see Table 11). Rats were administered a single s.c. or i.v. injection of GH (50 μg/kg i.v. or s.c.) or CTP-hGH-CTP-CTP (108 μg/kg i.v. or s.c.). With the exception of the predose sample, which was collected under isoflurane anesthesia, blood collection was performed in unanesthetized animals Blood samples (approximately 0.25 ml) were collected in EDTA-coated microtainers for ELISA analyses of CTP-hGH-CTP-CTP plasma concentration at the times outlined in Table 11. After each sampling, the blood volume was replaced with an equal volume of sterile 0.9% saline. Samples were stored on ice for up to 1 h prior to centrifugation and plasma harvest. Plasma samples were stored at approximately −20° C. prior to analysis.

TABLE 11

Experimental design of rat pharmacokinetic study

| Trt. Grp. | Test Article | No. of animals/ group/ timepoint | Dose Route | Gender | Dose Level (μg/kg) | Injected Vol. (μl) | Concentration (μg/ml)/Total vol. (ml) | Time-Points * (hours post-dose) |
|---|---|---|---|---|---|---|---|---|
| 1 | Biotropin | 6# | SC | Male | 50 | 500 | 20/5 | 0 (Pre-dose) 0.5, 2, 4, 8, 24, 48 |
| 2 | CTP-hGH-CTP-CTP | 6# | SC | Male | 108 | 500 | 43.2/5 | 0.5, 2, 4, 8, 24, 48, 72, 96 |
| 3 | Biotropin | 6# | IV | Male | 50 | 300 | 20/3 | 0, 0.12, 2, 4, 8, 24 |

TABLE 11-continued

Experimental design of rat pharmacokinetic study

| Trt. Grp. | Test Article | No. of animals/ group/ timepoint | Dose Route | Gender | Dose Level (µg/kg) | Injected Vol. (µl) | Concentration (µg/ml)/Total vol. (ml) | Time-Points * (hours post-dose) |
|---|---|---|---|---|---|---|---|---|
| 4 | CTP-hGH-CTP-CTP | 6# | IV | Male | 108 | 300 | 43.2/3 | 0.12, 2, 4, 8, 24, 48, 72 |
| | | Volume of blood sample/time point-500 µl | | | | | | Terminal blood samples |

3 rats per time point.

A commercial sandwich ELISA kit specific for detection of human growth hormone (Roche Diagnostics) was used for evaluation of the rat plasma samples. This kit detects human growth hormone in plasma by means of an antibody sandwich ELISA format. This kit was initially used to measure the concentration of CTP-hGH-CTP-CTP in rat plasma. For these plasma samples, an CTP-hGH-CTP-CTP standard curve (1.2-100 ng/ml) was used and the concentrations of CTP-hGH-CTP-CTP in rat plasma were interpolated from this curve.

Standard pharmacokinetic parameters, including clearance (CL or CL/F), volume of distribution (Vd or Vd/F), half-life ($t_{1/2}$), area under the plasma concentration versus time curve (AUC), maximal observed plasma concentration ($C_{max}$) and time to maximal observed plasma concentration ($T_{max}$), were obtained from plasma albutropin or GH concentration/time curves by noncompartmental analysis using the modeling program WinNonlin (Pharsight, version 3.1). Plasma CTP-hGH-CTP-CTP or GH concentration data were uniformly weighted for this analysis. The AUC was calculated using the log-linear trapezoidal analysis for the i.v. data and the linear-up/log-down trapezoidal method for the s.c. data. Plasma concentration profiles for each rat (with the exception of the s.c. albutropin data) or monkey were analyzed individually, and mean±standard error of the mean (S.E.M.) values for the pharmacokinetic parameters are reported in Table 12 and FIG. 12.

CTP-hGH-CTP-CTP is a single chain protein of 275 amino acids and up to twelve O-linked carbohydrates. The structure consists of modified human Growth Hormone (Somatropin) attached to three copies of the C-terminal peptide (CTP) of the beta chain of human Chorionic Gonadotropin (hCG); one copy at the N-terminus and two copies (in tandem) at the C terminus Human Growth Hormone is comprised of 191 amino acids. CTP is comprised of 28 amino acids and four O-linked sugar chains.

Example 10

Pharmacokinetics of CTP-Modified GH in SD Rats

The pharmacokinetics of CTP-hGH-CTP-CTP was evaluated and compared to that of commercial hGH (Biotropin).

TABLE 12

Mean pharmacokinetic parameters following single-dose i.v. and s.c. administration of CTP-hGH-CTP-CTP and GH (Biotropin) in Sprague-Dawley rats.
PK Statistics

| Parameters | Units | SC | | IV | |
|---|---|---|---|---|---|
| | | Biotropin | CTP-hGH-CTP-CTP | Biotropin | CTP-hGH-CTP-CTP |
| Dose | mg/Kg | 50 | 50 | 50 | 50 |
| AUClast | hr*ng/mL | 41 | 680 | 162.7 | 1568.3 |
| Cmax | ng/ml | 13 | 36.8 | 275.8 | 926 |
| Tmax | hr | 0.5 | 8 | 0 | 0 |
| MRT | hr | 2.5 | 12.9 | 0.5 | 9.9 |
| T½ alpha | hr | | 1.58 | | 0.74 |
| T½ beta | hr | 1.73 | 9 | 0.5 | 6.9 |

Data Statistical Analysis

Analysis of serum samples was performed in order to determine specific concentration levels for each sample. Concentration and time-point data were processed using WinNonLin noncompartmental analysis.

Figure 12:
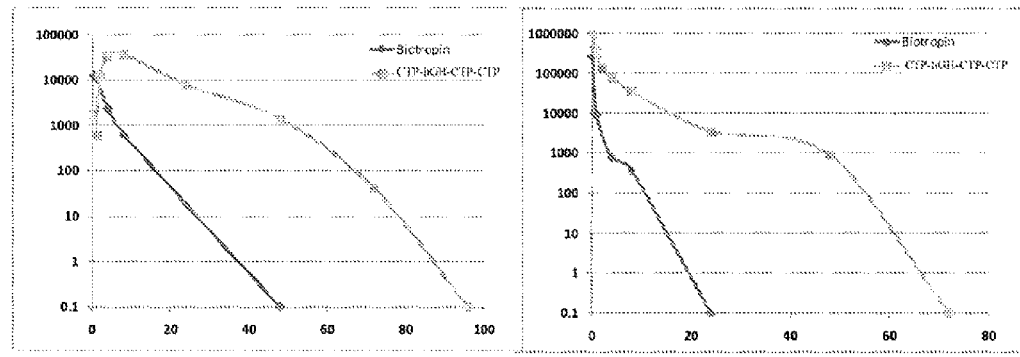
FIG. 12 are graphs showing the mean plasma CTP-hGH-CTP-CTP or GH concentrations (pg/ml) following a single i.v. or s.c. dose of CTP-hGH-CTP-CTP or GH in rats (n=3-6 per dose/route).

Parameters that were determined included: AUC, MRT, t1/2, Cmax, and Tmax. FIG. 12 demonstrates the superior pharmacokinetic profile of CTP-hGH-CTP-CTP plasma concentration compared to GH concentrations (pg/ml) following a single i.v. or s.c. dose of CTP-hGH-CTP-CTP or GH in rats (n=3-6 per dose/route).

Following a single S.C. injection of 50 µg/kg, clearance of CTP-hGH-CTP-CTP from SD rat's blood was significantly slower than that of CTP-hGH-CTP and of Biotropin. The corresponding calculated half-life times and AUCs were:

| Biotropin | T½ 1.7 h, AUC 41 hr*ng/mL |
| CTP-hGH-CTP | T½ 8.5 h, AUC 424 hr*ng/mL |
| CTP-hGH-CTP-CTP | T½ 9.0 h, AUC 680 hr*ng/mL |

Conclusion: CTP-hGH-CTP-CTP was chosen as the final candidate out of 6 other variants. CTP-hGH-CTP-CTP demonstrated superior performance in terms of biological activity and pharmacokinetics.

Example 11

Weight Gain Assay (WGA) for Single Dose/Repeated Dose of CTP-Modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized were 70-90 grams, at the time of the experiment. This is the standard USP and EP bioassay for hGH. Hypophysectomized rats (rats from which the pituitary gland was removed) lose their ability to gain weight. Injections of hGH (and of CTP-hGH-CTP-CTP) to these rats result in weight gain. Based on the measured weight gain along a defined period of time and the amount of hGH injected, the specific activity of hGH (and CTP-hGH-CTP-CTP) is determined. Rats were administered either a single s.c. doses of 0.4, 0.8 and 4 mg/Kg or repeated s.c. doses of 0.6 and 1.8 mg/Kg 4 days apart for 3 weeks. Individual body weights of all animals are determined at randomization, prior to the first dosing, thereafter every two days or in case of decedents at the time of death, and prior to sacrifice.

Single Dose and Repeated Dose Weight Gain Assay

Figure 13:
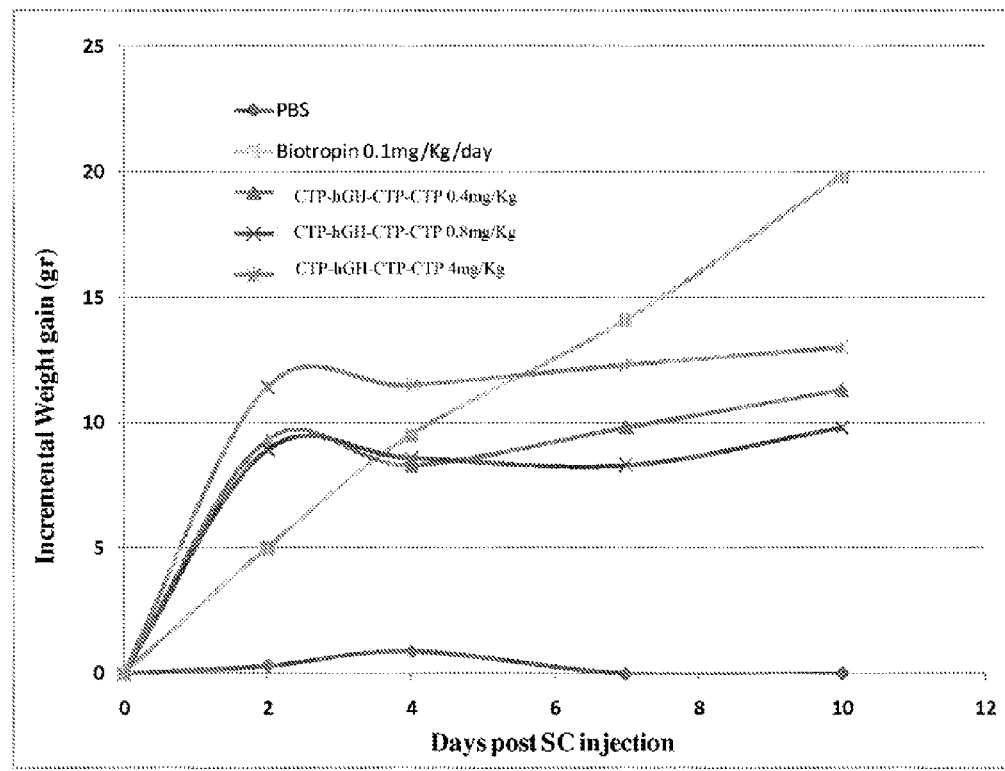
FIG. 13 are graphs showing the mean incremental weight gain following a single s.c. doses of CTP-hGH-CTP-CTP (0.4, 0.8 and 4 mg/Kg) in hypophysectomized rats in comparison to daily GH injections (0.1 mg/Kg/Day) (n=10 per dose).

The results comparing whole body growth response following different dosing patterns of CTP-hGH-CTP-CTP in hypophysectomized rats are demonstrated in FIG. 13. The results demonstrate that a single injection of 0.4 & 0.8 mg/Kg/day doses of hGH-CTP were equivalent to 4 daily injections of 0.1 mg/Kg/day of Biotropin. The peak of the hGH-CTP effect was after 2 days.

Figure 14:
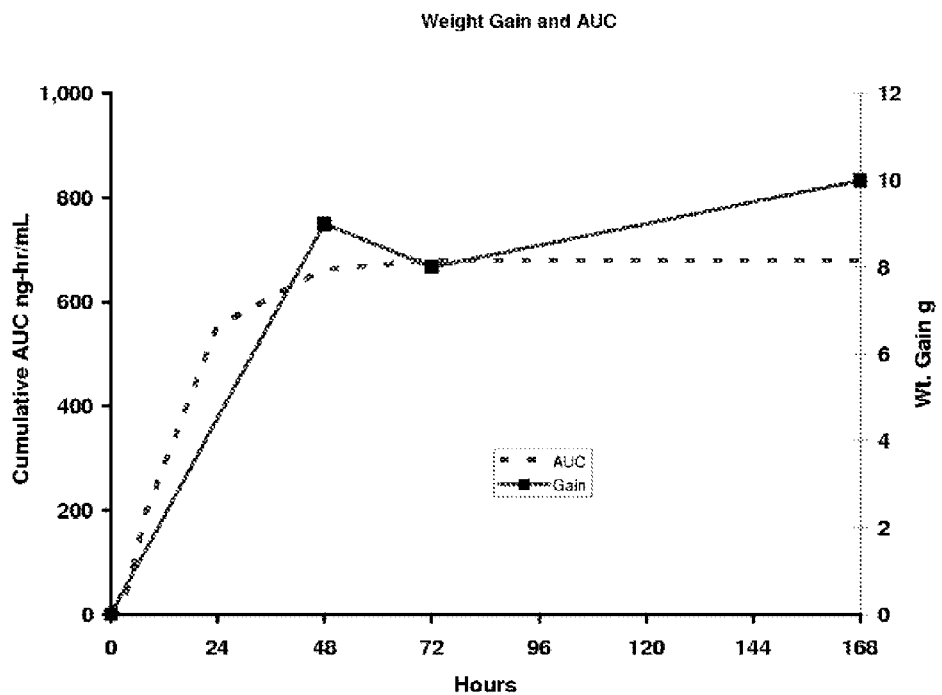
FIG. 14 is a graph showing the area Under the Curve following single injection of CTP-hGH-CTP-CTP correlates with Body Weight gain in Rats.

FIG. 14 further demonstrates that the area under the curve following single injection of CTP-hGH-CTP-CTP correlates with Body Weight gain in Rats. Thus, the collective data demonstrates that body weight gain is closely correlated with cumulative AUC.

Figure 15:
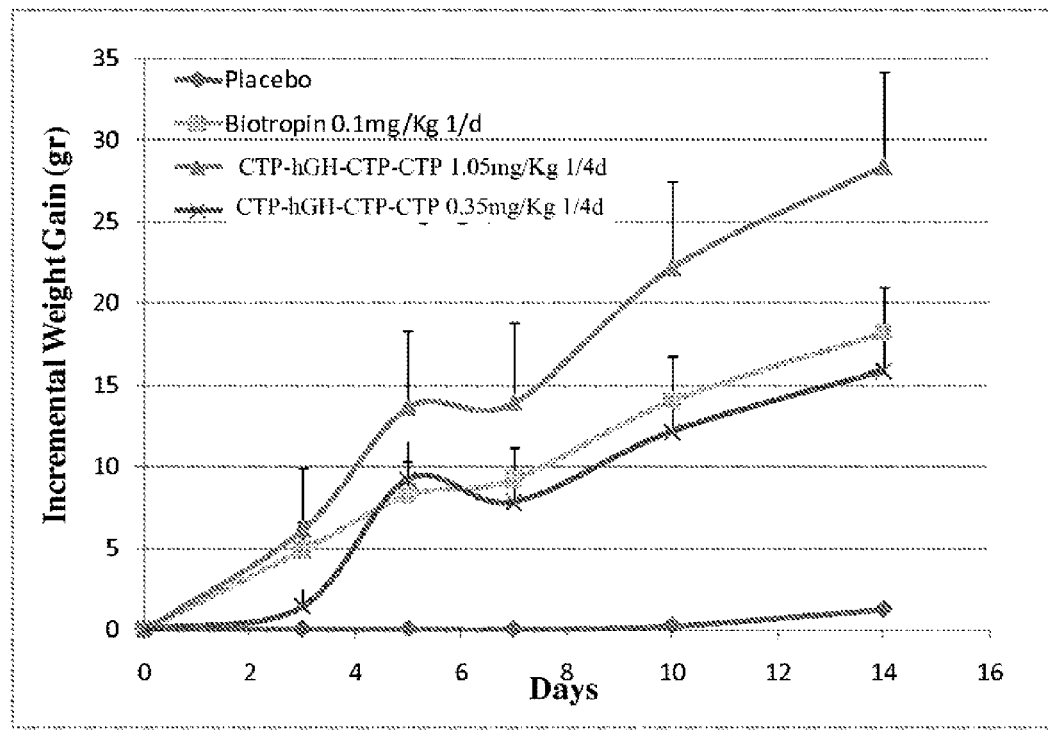
FIG. 15 is a graph showing the incremental weight gain following an s.c. doses of CTP-hGH-CTP-CTP (0.4, 0.8 and 4 mg/Kg) 4 days apart in hypophysectomized rats in comparison to daily GH injections (0.1 mg/Kg/Day) (n=10 per dose).

The hGH-CTP construct administered 4 days apart promotes the same weight gain as daily injections of Biotropin as demonstrated in FIG. 15. Half-life of hGH in humans is expected to be 5× better than in rats—indicating potential peak effect in humans after 10 days for one single injection. These results support administration of hGH-CTP construct, CTP-hGH-CTP-CTP, once weekly or biweekly in humans.

Example 12

Pharmacodynamics/Pharmacokinetics Studies of CTP-Modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized and sham rats were 70 and 150 g, respectively, at the time of the experiment.

Rats were administered a single s.c. with CTP-hGH-CTP-CTP, vehicle, human growth hormone CTP-hGH-CTP-CTP or human growth hormone (20 μg/rat) was administered s.c. in an injection volume of 0.2 ml/rat. The dose of GH was 0.35 and 1.05 μg/Kg, a dose of growth hormone that was equimolar with the amount of GH in a corresponding 0.6 and 1.8 μg/Kg dose of CTP-hGH-CTP-CTP. The treatment groups are summarized in Table 13. Following injection, plasma samples for IGF-1 analyses were obtained at the times described in Table 13. Samples were analyzed for IGF-1 concentration using a commercial ELISA (R&D systems).

TABLE 13

Treatment schedule for hypophysectomized rat study

| Trt. Grp. | Test Article | No. of animals/ group/ timepoint | Dose Route | Eq. Dose (mg/rat) | Eq. Dosage (mg/Kg) | CTP-hGH-CTP-CTP Conc. mg/ml | Dose Vol. (ml) | Time-Points * (hours post-dose) |
|---|---|---|---|---|---|---|---|---|
| M7 | Biotropin | 9 | SC | 0.032 | 0.35 | 0.16 | 0.2 | 0 (Pre-dose) 0.5, 2, 4, 8, 24, 48, 72, 96 |
| M8 | Biotropin | 9 | SC | 0.095 | 1.05 | 0.475 | 0.2 | 0 (Pre-dose) 0.5, 2, 4, 8, 24, 48, 72, 96 |
| M9 | EN648-01-08-005 | 12 | SC | 0.032 (0.055) | 0.35 (0.6) | 0.275 | 0.2 | 1, 2, 4, 8, 24, 48, 72, 96 |
| M10 | EN648-01-08-005 | 12 | SC | 0.095 (0.165) | 1.05 (1.8) | 0.825 | 0.2 | 1, 2, 4, 8, 24, 48, 72, 96 Terminal blood samples |

Volume of blood sample/time point-500 μl

Non-compartmental pharmacokinetic analysis was performed on the mean serum concentration versus time curves for each group. CTP-hGH-CTP-CTP Cmax was significantly higher than Biotropin Cmax. The terminal half-live of CTP-hGH-CTP-CTP was 6 times higher than Biotropin.

TABLE 14

Pharmacokinetic Parameter Estimates of CTP-hGH-CTP-CTP and Biotropin
Following a Single Subcutaneous Injection in hypophysectomized Rats

| Group | Dose mg/kg | Gender | Cmax ng/mL | Tmax hr | $AUC_{0-\infty}$ ng-hr/mL | $AUC_{0-t}$ ng-hr/mL | CL/F mL/hr/kg | $T_{1/2}$ hr |
|---|---|---|---|---|---|---|---|---|
| CTP-hGH-CTP-CTP | 1.8 | M | 2,150 | 8 | 37,713 | 37,695 | 0.928 | 6.86 |
| hGH | 0.6 | M | 681 | 8 | 11,505 | 11,489 | 3.042 | 6.8 |
|  | 1.05 | M | 1,078 | 0.5 | 3,541 | 3,540 | 9.884 | 1 |
|  | 0.35 | M | 439 | 0.5 | 1,279 | 1,279 | 27.36 | 1 |

Figure 16:
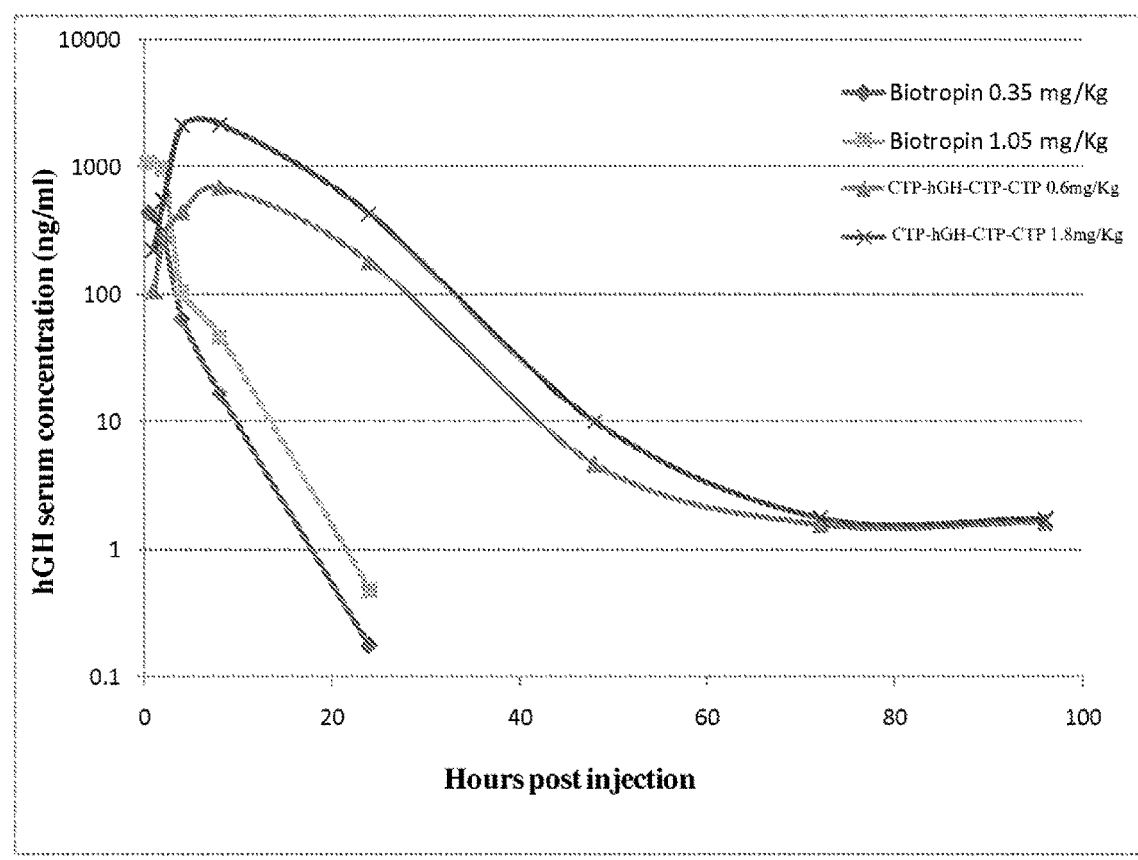
FIG. 16 is a graph showing hGH serum concentration in hypophysectomized rat following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum hGH post injection was measured using specific ELISA kits.

The $AUC_{0-t}$ and the $AUC_{0-\infty}$ were very similar suggesting the duration of sampling was adequate to characterize the pharmacokinetic profiles. AUC of CTP-hGH-CTP-CTP was 10 times higher than of Biotropin. Moreover, Cmax was generally proportional to dose and for CTP-hGH-CTP-CTP and it was twice higher than Cmax of Biotropin. However, as shown in FIG. 16, Tmax of CTP-hGH-CTP-CTP was 8 hr as compare to 0.5 hr of Biotropin, and the terminal half-lives did not appear to vary with dose level. T1/2 of CTP-hGH-CTP-CTP was 6.8 times longer than of Biotropin.

Figure 17:
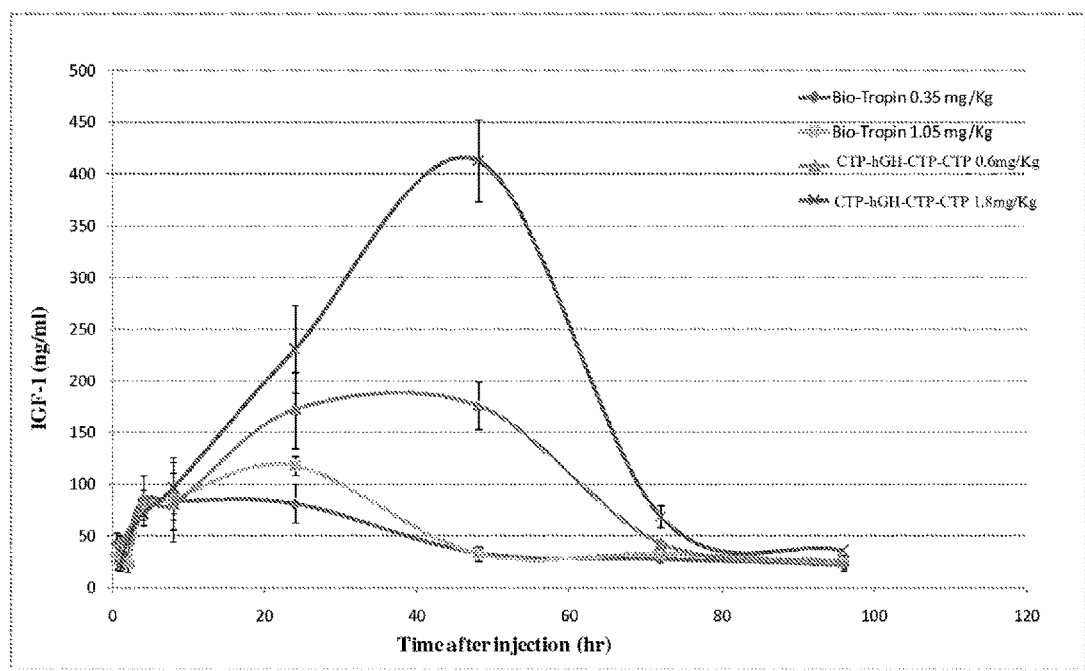
FIG. 17 is a graph showing IGF-1 serum levels in Hypophysectimized Rats Following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum IGF-I post injection was measured using specific ELISA kits (Roche Diagnostics).

Indirect effects of GH are mediated primarily by an insulin-like growth factor-I (IGF-I), a hormone that is secreted from the liver and other tissues in response to growth hormone. A majority of the growth promoting effects of growth hormone is actually due to IGF-I acting on its target cells. Accordingly, the effect of the CTP-hGH construct, CTP-hGH-CTP-CTP, on IGF-1 serum levels in Hypophysectimized Rats was measured. FIG. 17 presents results of IGF-1 serum levels in Hypophysectimized Rats Following SC injection of CTP-hGH-CTP-CTP and commercial hGH.

Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum IGF-I post injection was measured using specific ELISA kits (Roche Diagnostics).

The cumulative serum levels of IGF-I following injection of CTP-hGH-CTP-CTP was significantly higher than following injection of Biotropin. Cmax was generally proportional to dose and for CTP-hGH-CTP-CTP it was 3-4 times higher than Cmax of Biotropin. Tmax of CTP-hGH-CTP-CTP was 36-48 hr as compare to 20-24 hr of Biotropin. In conclusion, higher hGH levels and longer presence in serum result in significant increase in IGF-1 levels.

Example 13

Carbohydrate Content and Sialic Acid Content of CTP-Modified GH

Analysis of O-glycans is based on a Prozyme kit. O-glycans are chemically and enzymatically cleaved from the protein and separated from peptides using paper chromatography. Sequencing of the O-glycan pool is performed by sequential enzymatic digestions (exo-glycosidases) followed by HPLC analysis compared to standards.

Glycoprofiling with Sequence Analysis

Glycoprofiling was performed by Ludger Ltd. Two samples (EN648 and RS0708) were taken through triplicate releases and each release was also analyzed by HPLC in triplicate. Triplicate 300 µg samples of EN648 and RS0708 and a single 100 µl sample of citrate/sodium chloride buffer, plus a positive control fetuin (250 µg) and a 100 µl water negative control, were ultra-filtrated by centrifugation using a molecular weight cut off membrane of 10,000 Da to replace the buffer with water, then taken through hydrazinolysis under O-mode conditions (6 h at 60° C.). Released glycans were re-N-acetylated and cleaned up by LudgerClean CEX cartridges. An aliquot of the released glycans was then labeled with 2-aminobenzamide (2AB), cleaned up with Ludger Clean S cartridges and analyzed by LudgerSep-N2 HILIC-HPLC.

Monosaccharide Content

Analysis of neutral monosaccharides requires hydrolysis of glycans to their constituent monosaccharide components. The hydrolysis was performed by Ludger Ltd, on intact glycoprotein samples. Specifically, 50 µg of intact glycoprotein was acid hydrolyzed, 2-AB (2-aminobenzamide) labeled and run on a reverse phase HPLC column. This method hydrolyzes all glycans present on the glycoprotein inclusive of N and O linked types.

Sialic Acid Profiling

Two samples (EN648 and RS0708) and a buffer control were analyzed. Sialic acid analysis requires mild acid release of the monosaccharides followed by DMB fluorophore labeling and HPLC analysis on a LudgerSep-R1 column 50 µg of intact glycoprotein was acid hydrolyzed for each analysis.

Glyco Analysis of CTP-hGH-CTP-CTP

TABLE 15

Glycan analysis. Structural assignments and percentage areas of peaks are based upon HPLC and enzyme array digests.

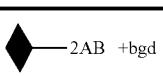

| | | | | Percent from total glycans[e] | | | |
|---|---|---|---|---|---|---|---|
| Peak ID[a] | GU[b] | Structure[c] | name | Und[d] | NAN1 | ABS | ABS BTG |
| 1[f] | 0.92 | ◆—2AB +bgd | GalNAc | 0.4 | 0.4 | 0.6 | 53.0 |

TABLE 15-continued

Glycan analysis. Structural assignments and percentage areas of peaks are based upon HPLC and enzyme array digests.

| Peak ID[a] | GU[b] | Structure[c] | name | Percent from total glycans[e] | | | |
|---|---|---|---|---|---|---|---|
| | | | | Und[d] | NAN1 | ABS | ABS BTG |
| 2[f] | 1.02 | | galactose | 1.9 | 9.7 | 23.8 | 26.5 |
| * | 1.72 | | | 4.3 | 4.6 | 2.3 | |
| 3 | 1.79 | | Galβ1-3GalNAc | 2.3 | 67.7 | 69.4 | 17.1[h] |
| 4[g] | 2.25 | | NeuNAcα2-3Gal | 19.8 | 13.0[h] | | |
| * | 2.57 | | | 1.5 | 1.9 | 1.1 | 1.1 |
| 5 | 2.90 | | NeuNAcα2-3Galβ1-3 GalNAc | 70.6 | | | |
| * | 3.58 | | | 0.6 | 0.7 | 0.6 | |
| 6 | 3.22 | | Galβ1-3[NeuNAcα2-6]GalNAc | 0.9 | 2.3 | | |
| 7 | 4.42 | | NeuNAcα2-3Galβ1-3[NeuNAcα2-6]GalNAc | 1.8 | | | |

The monosaccharide profiles indicate that the CTP-hGH-CTP-CTP glycoprotein samples contain predominantly O-link type glycans. The major O-glycan peak is sialylated core 1 (Neu5Acα2-3Galβ1-3GalNAc). The major sialic acid is Neu5Ac and there are some minor peaks suggesting the presence of 3-4% of di-acetylated sialic acid N-acetyl-9-O-acetylneuraminic acid (Neu5, 9Ac2) and less than 1% N-glycolylneuraminic acid. There are also small amounts of Neu5Acα2-6(Galβ1-3)GalNAc.

Example 14

Pharmacokinetic/Toxicokinetic Analysis of CTP-Modified GH in Rhesus Monkeys

Serum concentrations versus time curves were generated for each animal. Non-compartmental analysis was performed with WinNonlin professional version 5.2.1 (Pharsight Corporation, Mt View Calif.). The estimated pharmacokinetic parameters are shown in Table 16 below:

TABLE 16

Estimates of CTP-hGH-CTP-CTP Pharmacokinetic Parameters (Mean ± SD) from Non-compartmental Analysis Following A Single Subcutaneous Injection in Rhesus Monkeys

| Parameter | 1.8 mg/kg | 90 mg/kg |
|---|---|---|
| Cmax (µg/mL) | 2.073 ± 0.417 | 108.7 ± 46.0 |
| Tmax (hr) | 4 ± 0 | 11 ±7 |
| $AUC_{0-t}$ (µg-hr/mL) | 38.7 ± 7.4 | 2,444 ± 394 |
| $AUC_{0-\infty}$ (µg-hr/mL) | 39.0 ± 7.3 | 2,472 ± 388 |
| CL/F (mL/hr/kg) | 47.5 ± 9.0 | 37.04 ± 4.78 |
| $T_{1/2}$ (hr) | 10.00 ± 1.47 | 9.85 ± 1.07 |
| Vz/F (mL/kg) | 701 ± 236 | 529 ± 104 |

The $AUC_{0-t}$ and the $AUC_{0-\infty}$ were very similar suggesting the duration of sampling was adequate to characterize the pharmacokinetic profiles. Cmax was proportional to dose. Tmax was later at the higher dose. Tmax was at 4 hours for all animals in the low dose group and was at 8 or 24 hours in the high dose group. Terminal half-lives are similar for the two dose groups.

AUC was approximately proportional to dose with a slightly larger than proportional AUC at the higher dose producing a slightly lower estimate for CL/F and Vz/F compared to the lower dose. It is not possible to say if CL and Vz are lower at the higher dose or if F is lower at the lower dose. There was overlap between the groups so it is questionable that this represents a meaningful difference in CL/F and Vz/F.

Pharmacokinetic parameters estimated by the model were very similar to those from non-compartment analysis. Absorption and elimination half-lives are shown in Table 17 below:

TABLE 17

Estimates of CTP-hGH-CTP-CTP Absorption and Elimination Half-lives (Mean ± SD) Following Subcutaneous Injection Derived From Pharmacokinetic Modeling in Rhesus Monkeys

| Dose | $T_{1/2\ abs}$ (hr) | $T_{1/2\ el}$ (hr) |
|---|---|---|
| 1.8 mg/kg | 1.17 ± 0.40 | 10.41 ± 2.36 |
| 90 mg/kg | 6.49 ± 1.87 | 7.26 ± 1.85 |

The data indicate that the elimination rates are fairly similar between the groups with a slightly longer T1/2 el in the lower dose group. The absorption, however, is more than 5-fold slower following subcutaneous administration of 90 mg/kg compared to that following 1.8 mg/kg. As in the case of the non-compartmental analysis, modeling indicated a later Tmax at the high dose.

Although GH supplementation is effective in the treatment of GH deficiency in children and adults, the disadvantages of daily injections over extended periods of time limit its use by physicians in certain patient populations as well as increase the risk of dosing error, the number of care givers, the cost of treatment and/noncompliance. Especially important in certain populations, such as children of short stature who may not understand the implications of not following the prescribed GH dosing regimen, is the necessity of compliance to achieve the optimal benefit from GH therapy. The issue of finding a more suitable alternative to daily GH injections and subsequent compliance gains further importance as GH-deficient children transition into adults with a continuing need for GH treatment. The requirement of daily therapy is largely due to recombinant GH's short plasma half-life and has led to the development of a sustained release form of GH (Reiter E O. Attire K M., Mashing T J. Silverman B L. Kemp S F. Neolith R B. Ford K M. and Sanger P. A multimember study of the efficacy and safety of sustained release GH in the treatment of naive pediatric patients with GH deficiency. J. Clin. Endocrinol. Metab. 86 (2001), pp. 4700-4706).

GH-CTP, a recombinant human growth hormone-CTP fusion protein, as described herein, has a pharmacokinetic profile in the rat that is longer in duration than that of GH. This unique pharmacokinetic profile allows for intermittent administration of GH-CTP to achieve pharmacodynamic effects in growth-hormone-deficient rat as evidenced by growth and elevations in plasma IGF-1 levels, respectively.

GH-CTP offers a superior pharmacokinetic profile compared with that of GH when administered s.c. in the rat. There are substantial differences in plasma clearance of GH-CTP compared to GH. Specifically, plasma is cleared of GH-CTP at more than 6 times more slowly than GH following s.c. dosing. The terminal half-life and mean residence time of GH-CTP were approximately six times longer than that of GH in rats following s.c. administration. In addition, the Cl/F following s.c. dosing is 10 times lower for GH-CTP than for GH.

In an effort to examine whether the pharmacokinetic advantages in the rat translated to a pharmacodynamic benefit, the possibility that GH-CTP might stimulate growth in GH-deficient hypophysectomized rats with dosing regimens less frequent than daily was tested at equimolar CTP-hGH-CTP-CTP and GH dose levels. Single SC injection of GH-CTP promoted incremental weight gain which was equal to 4 daily consecutive injections of GH. In addition, the every fourth day administration schedule for GH-CTP shows enhanced body weight gain over GH.

Pharmacodynamically, the long circulation time of GH-CTP relative to GH in the hypophysectomized rats resulted in a prolonged IGF-1 response measured in blood plasma following a single s.c. injection. Subcutaneous administration of a single dose of GH-CTP increased circulating IGF-1 concentrations in a dose-dependent manner in the hypophysectomized rats. At the highest albutropin dose, IGF-1 concentrations were elevated above baseline for as long as 75 hours after a single administration. Thus, the enhanced circulation time of a single dose of GH-CTP resulted in substantial pharmacodynamic improvement over a single dose of GH, raising the possibility that GH-CTP could offer similar growth enhancement with reduced dosing frequency compared with standard GH treatment regimens.

Single CTPs modified hGH-dose of 90 mg/kg in Rhesus and 180 mg/kg in rats were well tolerated in both species. The allometric factor between rats and primates is approximately ×2 which is based on the anticipated clearance of proteins in these animals. In-line with industry-accepted extrapolation models for therapeutic proteins' half-life increase between species (FDA Guidance). 90 mg/kg in Primates has a PK profile slightly better than 180 mg/kg of CTPs modified hGH in Rat. Thus, allometric extrapolation to humans supports weekly or once/2 w injection.

The present concept utilizing a CTP-GH construct, reduced dosing frequency compared to the commercial GH recombinant product. Nutropin Depot® is a sustained release formulation of GH approved for use in pediatric populations; however, comparisons to historical controls have revealed that 1- and 2-year growth rates are significantly (p<0.001) lower in children given Nutropin Depot® (1-year growth rate 8.2±1.8 cm/year) than in children treated with GH (one-year growth rate 10.1±2.8 cm/year) (Silverman B L. Blethen S L. Reiter E O. Attie K M. Neuwirth R B. and Ford K M. A long-acting human growth hormone (Nutropin Depot®): efficacy and safety following two years of treatment in children with growth hormone deficiency. J. Pediatr. Endocrinol. Metab. 15 (2002), pp. 715-722). The local effects of subcutaneously administered Nutropin Depot® include nodules, erythema, pain at the injection site, headache and vomiting. Preclinical toxicology studies in both rat and monkey have shown that s.c. administration of CTP-hGH-CTP-CTP produces no local reactions compared to vehicle. Given the medical need for a less frequently administered form of GH, the pharmacologic properties of CTP-hGH-CTP-CTP in this study in rats suggest that this product is favorable also in terms of toxicology and patient compliance. The sustained activity of CTP-hGH-CTP-CTP in the rat support its potential utility as an agent that requires only intermittent administration to attain a therapeutic benefit that is currently achieved with daily dosing.

Example 15

Long-Acting CTP-Modified Version of Human Growth Hormone (hGH-CTP) was Highly Effective in Growth Hormone Deficient Adults—Phase II Clinical Trial A randomized, open-label, Phase II Clinical Trial was conducted to evaluate the safety, tolerability, pharmacokinetics and pharmacodynamic properties of hGH-CTP injected either weekly or twice-monthly in patients who currently receive daily injections of growth hormone. The trial was conducted at multiple sites in six countries. The three main cohorts in the trial received a single weekly dose of hGH-CTP, containing 30%, 45% or 100% of the equivalent cumulative commercial hGH dose that growth hormone-deficient adult patients receive over the course of seven days in the form of daily injections (referred to as the "30%", "45%" and "100%" cohorts, respectively). The data reflect results from 39 patients, 13 in each cohort. 2 females were included in each cohort.

In addition to the three main cohorts, growth hormone deficient adults were enrolled in an experimental fourth cohort, which is conducted outside of the formal Phase II trial. The patients in the experimental fourth cohort receive a single injection of hGH-CTP once every two weeks that contains 50% of the cumulative commercial dose of that growth hormone-deficient adult patients receive over a two-week period in the form of daily injections.

Efficacy for the three main cohorts receiving a single weekly injection of hGH-CTP is defined by measuring daily insulin-like growth factor 1 (IGF-1) levels within the desired therapeutic range over a period of seven days (during the last week of treatment in the study). The desired therapeutic range is defined as between +2 standard deviations through −2 standard deviations from the average IGF-1 levels expected in a normal population, stratified by age group and gender. In addition, the trial measured IGF-1 levels within a narrower range of +/−1.5 standard deviations for the purpose of observing the variance of the patients within the normal range.

Results:

Table 18 contains the average percent of days within the normal therapeutic range (+/−2 SD), average percent of days within a narrower normal therapeutic range (+/−1.5 SD), and average Cmax (highest concentration level) of IGF-1 for males, measured during the last treatment week, expressed in standard deviations from the normal population mean IGF-1 levels.

TABLE 18

Human Phase II Clinical Trial Results.

| Cohort | % Days Within Narrow Normal Range of IGF-1 (+/−1.5 SD) | % Days Within Normal Range of IGF-1 (+/−2 SD) | Avg. Cmax of IGF-1 (preferred below +2 SD) |
|---|---|---|---|
| 30% | 57% | 100% | −0.9 |
| 45% | 100% | 100% | 0.1 |
| 100% | 86% | 100% | 0.4 |

Two mg per week of hGH-CTP, containing 50% of the cumulative weekly hGH dose that an adult patient would usually be prescribed as the initial treatment dose, has a high likelihood of being defined as the starting dose for males and females in the adult Phase III.

There was no evidence of safety and/or tolerability issues, and no indication that hGH-CTP, when used in high doses, induced excessive levels of IGF-1 in patients or even levels above the normal range.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of treating a subject suffering from a fatigue syndrome following cancer chemotherapy or a chronic infection, wherein said subject is anemic, said method comprising administering to a subject a therapeutically effective amount of a polypeptide consisting of a chorionic gonadotropin carboxy terminal peptide (CTP) modified erythropoietin (EPO), said CTP-modified EPO consisting of one chorionic gonadotropin carboxy terminal peptide (CTP) attached to the amino terminus of said EPO, and two chorionic gonadotropin CTPs attached to the carboxy terminus of said EPO, wherein said polypeptide consists of a precursor or a mature polypeptide and optionally a signal peptide attached to the amino terminus of said one CTP, wherein said administration treats the anemic subject suffering from fatigue syndrome following cancer chemotherapy or a chronic infection, or any combination thereof.

2. The method of claim 1, wherein the sequence of at least one chorionic gonadotropin carboxy terminal peptide consists of an amino acid sequence selected from the group consisting of SEQ ID NO: 17 and SEQ ID NO: 18.

3. The method of claim 1, wherein at least one chorionic gonadotropin carboxy terminal peptide is truncated.

4. The method of claim 1, wherein said EPO is glycosylated.

5. The method of claim 1, wherein said EPO is non-glycosylated.

6. The method of claim 1, wherein at least one chorionic gonadotropin carbon terminal peptide is glycosylated.

7. The method of claim 1, wherein the amino acid sequence of said mature CTP-modified EPO polypeptide is set forth in SEQ ID NO: 51.

8. The method of claim 1, wherein the amino acid sequence of said precursor CTP-modified EPO polypeptide is set forth in SEQ ID NO: 3.

9. The method of claim 8, wherein said precursor CTP-modified EPO polypeptide comprises a signal peptide attached to the amino terminus of said one CTP, wherein the amino acid sequence of said signal peptide is set forth in SEQ ID NO: 19.

10. The method of claim 1, wherein said chronic infection comprises HIV, inflammatory bowel disease, or septic episodes, or any combination thereof.

* * * * *